(12) United States Patent
McKinney

(10) Patent No.: US 12,376,785 B2
(45) Date of Patent: Aug. 5, 2025

(54) CATHETER FOR MONITORING INTRA-ABDOMINAL PRESSURE FOR ASSESSING PREECLAMPSIA

(71) Applicant: Sentinel Medical Technologies, LLC, Boca Raton, FL (US)

(72) Inventor: Timothy McKinney, Boca Raton, FL (US)

(73) Assignee: Sentinel Medical Technologies, LLC, Boca Raton, FL (US)

( * ) Notice: Subject to any disclaimer, the term of this patent is extended or adjusted under 35 U.S.C. 154(b) by 0 days.

(21) Appl. No.: 18/242,584

(22) Filed: Sep. 6, 2023

(65) Prior Publication Data

US 2023/0414165 A1   Dec. 28, 2023

Related U.S. Application Data

(63) Continuation of application No. 16/752,578, filed on Jan. 24, 2020, now Pat. No. 11,779,263.
(Continued)

(51) Int. Cl.
*A61B 5/00* (2006.01)
*A61B 5/20* (2006.01)
(Continued)

(52) U.S. Cl.
CPC .......... *A61B 5/4343* (2013.01); *A61B 5/205* (2013.01); *A61B 5/6853* (2013.01); *A61B 5/0004* (2013.01);
(Continued)

(58) Field of Classification Search
CPC ......... A61B 5/0004; A61B 5/01; A61B 5/036; A61B 5/205; A61B 5/4343; A61B 5/4848;
(Continued)

(56) References Cited

U.S. PATENT DOCUMENTS

| | | |
|---|---|---|
| 3,721,229 A | 3/1973 | Panzer |
| 4,192,319 A | 3/1980 | Hargens et al. |

(Continued)

FOREIGN PATENT DOCUMENTS

| | | |
|---|---|---|
| CA | 2961757 | 3/2016 |
| CN | 201267504 | 7/2009 |

(Continued)

OTHER PUBLICATIONS

Sawchuck, Diane, et al. "Pre-Eclampsia renamed and reframed: Intra-abdominal hypertension in pregnancy" Nov. 2014, Medical Hypothese, 83, 619-632 (Year: 2014).*

(Continued)

*Primary Examiner* — Alex M Valvis
*Assistant Examiner* — Anna Roberts
(74) *Attorney, Agent, or Firm* — Neil D. Gershon

(57) ABSTRACT

A method and device for measuring intra-abdominal pressure in a pregnant woman to assess likelihood or occurrence of pre-eclampsia. The method includes providing a catheter having first and second lumens and a balloon, inserting the catheter into a bladder of the patient, injecting gas into the first lumen of the catheter to expand the balloon, obtaining a first pressure reading of the bladder based on deformation of the balloon to thereby monitor pressure within an abdomen of the mother to assess if pre-eclampsia is occurring or likely to occur and transmitting the first pressure reading to an external monitor connected to the catheter. The pressure reading is indicative of the presence and/or risk of pre-eclampsia to determine when intervention should occur to prevent morbidity and mortality of the woman and baby.

20 Claims, 81 Drawing Sheets

Related U.S. Application Data

(60) Provisional application No. 62/803,284, filed on Feb. 8, 2019.

(51) Int. Cl.
*A61M 25/00* (2006.01)
*A61M 25/10* (2013.01)

(52) U.S. Cl.
CPC ....... *A61M 25/0026* (2013.01); *A61M 25/007* (2013.01); *A61M 25/1011* (2013.01)

(58) Field of Classification Search
CPC ... A61B 5/6853; A61B 5/4878; A61B 5/6874; A61B 5/7275; A61B 2503/02; A61B 2562/168; A61M 25/0026; A61M 25/007; A61M 25/1011
See application file for complete search history.

(56) References Cited

U.S. PATENT DOCUMENTS

| | | | |
|---|---|---|---|
| 4,335,723 A | 6/1982 | Patel | |
| 4,739,769 A | 4/1988 | Mathews et al. | |
| 4,873,986 A | 10/1989 | Wallace | |
| 4,901,731 A | 2/1990 | Millar | |
| 4,976,692 A | 12/1990 | Atad | |
| 5,135,002 A | 8/1992 | Kirchner et al. | |
| 5,167,237 A | 12/1992 | Rabin et al. | |
| 5,398,692 A | 3/1995 | Hickey | |
| 5,447,497 A | 5/1995 | Sogard et al. | |
| 5,431,629 A | 7/1995 | Lampropoulos et al. | |
| 5,433,216 A | 7/1995 | Sugrue et al. | |
| 5,551,439 A | 9/1996 | Hickey | |
| 5,566,680 A | 10/1996 | Urion | |
| 5,570,671 A | 11/1996 | Hickey | |
| 5,573,007 A | 11/1996 | Bobo, Sr. | |
| 5,697,375 A | 12/1997 | Hickey | |
| 5,707,358 A | 1/1998 | Wright | |
| 5,951,497 A * | 9/1999 | Wallace ............. | A61B 5/035 |
| | | | 600/176 |
| 5,980,485 A | 11/1999 | Grantz et al. | |
| 5,984,879 A | 11/1999 | Wallace et al. | |
| 6,021,781 A | 2/2000 | Thompson et al. | |
| 6,115,624 A | 9/2000 | Lewis | |
| 6,167,886 B1 | 1/2001 | Engel | |
| 6,183,421 B1 | 2/2001 | Bobo | |
| 6,231,524 B1 | 5/2001 | Wallace et al. | |
| 6,248,083 B1 | 6/2001 | Smith | |
| 6,434,418 B1 | 8/2002 | Neal et al. | |
| 6,447,462 B1 | 8/2002 | Wallace et al. | |
| 6,450,971 B1 | 9/2002 | Andrus et al. | |
| 6,461,332 B1 | 10/2002 | Mosel et al. | |
| 6,585,660 B2 | 7/2003 | Dorando | |
| 6,648,879 B2 | 11/2003 | Joye et al. | |
| 6,673,022 B1 | 1/2004 | Bobo et al. | |
| 6,723,053 B2 | 4/2004 | Ackerman et al. | |
| 6,827,710 B1 | 12/2004 | Mooney et al. | |
| 6,890,307 B2 | 5/2005 | Kokate et al. | |
| 7,081,096 B2 | 7/2006 | Brister et al. | |
| 7,347,822 B2 | 3/2008 | Brockway et al. | |
| 7,381,190 B2 | 6/2008 | Sugrue et al. | |
| 7,654,967 B2 | 2/2010 | Bobo, Sr. | |
| 7,722,544 B2 | 5/2010 | Williams et al. | |
| 7,828,753 B2 | 11/2010 | Euliano, II et al. | |
| 7,959,579 B2 | 6/2011 | Dijkman | |
| 7,976,475 B2 | 7/2011 | Dijkman | |
| 8,007,444 B2 | 8/2011 | Kokate et al. | |
| 8,192,368 B2 | 6/2012 | Woodruff et al. | |
| 8,235,426 B2 | 8/2012 | Pisula, Jr. et al. | |
| 8,337,411 B2 | 12/2012 | Nishtala et al. | |
| 8,360,988 B2 | 1/2013 | Bobo, Sr. et al. | |
| 8,403,884 B2 | 3/2013 | Nishtala | |
| 8,491,503 B2 | 7/2013 | Zaiken et al. | |
| 8,535,237 B2 | 9/2013 | Nishtala | |
| 8,596,688 B2 | 12/2013 | Pisula, Jr. et al. | |
| 8,626,316 B2 | 1/2014 | Mohl | |
| 8,636,724 B2 | 1/2014 | Wiita et al. | |
| 8,636,728 B2 | 1/2014 | Watson | |
| 8,646,325 B2 | 2/2014 | Hoem et al. | |
| 8,708,927 B2 | 4/2014 | Dijkman | |
| 8,876,729 B2 | 11/2014 | Bobo, Sr. et al. | |
| 9,046,205 B2 | 6/2015 | Whitaker et al. | |
| 9,055,949 B2 | 6/2015 | Belfort | |
| 9,101,314 B2 | 8/2015 | Shi | |
| 9,107,695 B2 | 8/2015 | Horton et al. | |
| 9,108,000 B2 | 8/2015 | Kassab | |
| 9,126,008 B2 | 9/2015 | Kim | |
| 9,167,973 B2 | 10/2015 | Steiner et al. | |
| 9,393,353 B2 | 7/2016 | Alam et al. | |
| 9,439,600 B2 | 9/2016 | Mohl | |
| 9,440,043 B2 | 9/2016 | Arora et al. | |
| 9,510,766 B2 | 12/2016 | Weed et al. | |
| 9,511,209 B2 | 12/2016 | Drasler et al. | |
| 9,534,721 B2 | 1/2017 | Lombardi, III | |
| 9,597,140 B2 | 3/2017 | Mihalik | |
| 9,622,670 B2 | 4/2017 | Burnett et al. | |
| 9,623,201 B2 | 4/2017 | Gregory et al. | |
| 9,655,555 B2 | 5/2017 | Burnett et al. | |
| 9,662,058 B2 | 5/2017 | Burnett et al. | |
| 9,695,966 B2 | 7/2017 | Lombardi, III et al. | |
| 9,713,494 B2 | 7/2017 | Nabutovsky et al. | |
| 9,717,472 B2 | 8/2017 | Ahmed et al. | |
| 9,724,232 B2 | 8/2017 | Kassab et al. | |
| 9,734,706 B2 | 8/2017 | Moon et al. | |
| 9,757,545 B2 | 9/2017 | Kassab | |
| 9,782,115 B2 | 10/2017 | Shi | |
| 9,782,145 B2 | 10/2017 | Hart et al. | |
| 9,848,790 B2 | 12/2017 | Pintel | |
| 9,877,660 B2 | 1/2018 | O'Connell et al. | |
| 9,895,103 B2 | 2/2018 | Hyde et al. | |
| 9,913,585 B2 | 3/2018 | McCaffrey et al. | |
| 9,931,044 B2 | 4/2018 | Burnett et al. | |
| 9,931,122 B2 | 4/2018 | Burnett et al. | |
| 9,943,352 B2 | 4/2018 | Mihalik | |
| 10,004,551 B2 | 6/2018 | Burnett | |
| 10,194,813 B2 | 2/2019 | Bharucha et al. | |
| 10,206,575 B2 | 2/2019 | Al-Mayah | |
| 10,238,307 B2 | 3/2019 | Schlumpf et al. | |
| 10,314,488 B2 | 6/2019 | Samuelsson et al. | |
| 10,368,872 B2 | 8/2019 | Franklin et al. | |
| 10,376,679 B2 | 8/2019 | Cox et al. | |
| 10,391,275 B2 | 8/2019 | Burnett et al. | |
| 10,433,741 B2 | 10/2019 | Stimpson | |
| 10,478,113 B2 | 11/2019 | Damaser et al. | |
| 10,485,483 B1 | 11/2019 | Brody | |
| 10,517,538 B2 | 12/2019 | Burnett et al. | |
| 10,531,834 B1 | 1/2020 | Smith et al. | |
| 10,532,193 B2 | 1/2020 | Fischer, Jr. et al. | |
| 10,537,274 B2 | 1/2020 | Damaser et al. | |
| 10,537,308 B2 | 1/2020 | Zhadkevich | |
| 10,542,924 B2 | 1/2020 | Imran et al. | |
| 10,568,686 B2 | 2/2020 | Lee | |
| 10,617,313 B2 | 4/2020 | Smith | |
| 10,631,788 B2 | 4/2020 | Brody | |
| 10,743,780 B2 | 8/2020 | Hoem et al. | |
| 10,750,999 B2 | 8/2020 | Parks et al. | |
| 10,758,135 B2 | 9/2020 | Burnett et al. | |
| 10,772,998 B2 | 9/2020 | Luxon | |
| 10,773,059 B1 | 9/2020 | Sardesai | |
| 10,786,651 B2 | 9/2020 | Edminster et al. | |
| 11,065,418 B1 | 7/2021 | Brody | |
| 11,077,301 B2 | 8/2021 | Creasey | |
| 11,648,380 B2 | 5/2023 | McCloskey | |
| 2002/0143294 A1 | 10/2002 | Duchon et al. | |
| 2002/0183628 A1 | 12/2002 | Reich et al. | |
| 2003/0060800 A1 | 3/2003 | Ryan | |
| 2003/0114835 A1 | 6/2003 | Noda | |
| 2003/0163052 A1 | 8/2003 | Mott | |
| 2003/0181856 A1 | 9/2003 | Goldman | |
| 2004/0077976 A1 | 4/2004 | Wilson | |
| 2004/0127813 A1 | 7/2004 | Schwamm | |
| 2004/0171942 A1 | 9/2004 | Ackerman et al. | |
| 2005/0015047 A1 | 1/2005 | Shah | |
| 2005/0055043 A1 | 3/2005 | Foltz | |

(56) References Cited

U.S. PATENT DOCUMENTS

| | | |
|---|---|---|
| 2005/0065408 A1 | 3/2005 | Benderev |
| 2005/0187430 A1 | 8/2005 | Aundal et al. |
| 2005/0197585 A1 | 9/2005 | Brockway et al. |
| 2005/0215989 A1 | 9/2005 | Abboud |
| 2005/0240211 A1 | 10/2005 | Sporri |
| 2005/0283092 A1 | 12/2005 | Gedebov |
| 2006/0011820 A1 | 1/2006 | Chow-Shing et al. |
| 2006/0073728 A1 | 4/2006 | Zaiken |
| 2006/0085022 A1 | 4/2006 | Hayes |
| 2006/0085024 A1 | 4/2006 | Pepper |
| 2007/0083126 A1 | 4/2007 | Marko et al. |
| 2007/0191904 A1 | 8/2007 | Libbus et al. |
| 2007/0197963 A1 | 8/2007 | Griffiths et al. |
| 2007/0282219 A1 | 12/2007 | Holte |
| 2008/0027358 A1 | 1/2008 | Gregersen et al. |
| 2008/0077043 A1 | 3/2008 | Malbrain et al. |
| 2008/0103408 A1 | 5/2008 | Denton et al. |
| 2008/0139967 A1 | 6/2008 | Euliano |
| 2008/0146990 A1 | 6/2008 | Jenson et al. |
| 2009/0221993 A1 | 9/2009 | Sohi et al. |
| 2009/0240199 A1 | 9/2009 | Rahimsobhani |
| 2009/0306539 A1 | 12/2009 | Woodruff |
| 2010/0056952 A1 | 3/2010 | Liu |
| 2010/0069900 A1 | 3/2010 | Shirley |
| 2010/0094204 A1 | 4/2010 | Nishtala |
| 2010/0094328 A1 | 4/2010 | O'dea et al. |
| 2010/0113939 A1 | 5/2010 | Mashimo et al. |
| 2010/0113968 A1 | 5/2010 | Bobo |
| 2010/0168836 A1 | 7/2010 | Kassab |
| 2010/0249663 A1 | 9/2010 | Nishtala |
| 2011/0087109 A1 | 4/2011 | Swann |
| 2012/0010525 A1 | 1/2012 | Jacofsky et al. |
| 2012/0035595 A1 | 2/2012 | Goedje |
| 2012/0041334 A1 | 2/2012 | Goedje et al. |
| 2012/0053441 A1 | 3/2012 | Kassab |
| 2012/0179063 A1 | 7/2012 | Bharucha et al. |
| 2012/0316460 A1 | 12/2012 | Stout |
| 2012/0316461 A1 | 12/2012 | Liu |
| 2013/0030262 A1 | 1/2013 | Burnett et al. |
| 2013/0046217 A1 | 2/2013 | Mooney |
| 2013/0066166 A1 | 3/2013 | Burnett et al. |
| 2013/0079662 A1 | 3/2013 | Damaser et al. |
| 2013/0085519 A1 | 4/2013 | Kiminami |
| 2013/0211221 A1 | 8/2013 | Sunnarborg |
| 2013/0231584 A1 | 9/2013 | Burnett |
| 2013/0317367 A1 | 11/2013 | Shuler |
| 2014/0012305 A1 | 1/2014 | Horton et al. |
| 2014/0094716 A1 | 4/2014 | Zaiken et al. |
| 2014/0107550 A1 | 4/2014 | Paulson |
| 2014/0107573 A1 | 4/2014 | Wiita et al. |
| 2014/0128766 A1 | 5/2014 | Beran |
| 2014/0155745 A1 | 6/2014 | Duncan |
| 2014/0163415 A1 | 6/2014 | Zaiken |
| 2014/0200482 A1 | 7/2014 | Shi |
| 2014/0364835 A1 | 12/2014 | Allen |
| 2015/0042406 A1 | 2/2015 | Kovac et al. |
| 2015/0065807 A1 | 3/2015 | Greenberg et al. |
| 2015/0133799 A1 | 5/2015 | O'Connell et al. |
| 2015/0327836 A1 | 11/2015 | Stone et al. |
| 2015/0342512 A1 | 12/2015 | Shi |
| 2015/0351649 A1 | 12/2015 | Bobo, Sr. et al. |
| 2015/0366485 A1 | 12/2015 | Kassab |
| 2015/0366498 A1 | 12/2015 | Choi et al. |
| 2016/0029912 A1 | 2/2016 | Stimpson |
| 2016/0066831 A1 | 3/2016 | Hyde et al. |
| 2016/0074581 A1 | 3/2016 | Gerrans |
| 2016/0106323 A1 | 4/2016 | Ou et al. |
| 2016/0183819 A1 | 6/2016 | Burnett et al. |
| 2016/0220136 A1 | 8/2016 | Schultz |
| 2016/0249969 A1 | 9/2016 | Santoinanni |
| 2016/0256076 A1 | 9/2016 | Kassab |
| 2016/0310148 A1 | 10/2016 | Allen |
| 2016/0331294 A1 | 11/2016 | Imran et al. |
| 2016/0331451 A1 | 11/2016 | Nabutovsky et al. |
| 2016/0354028 A1 | 12/2016 | Damaser et al. |
| 2016/0354140 A1 | 12/2016 | Sharma |
| 2016/0374576 A1 | 12/2016 | Ziaie et al. |
| 2017/0055874 A1 | 3/2017 | Papirov et al. |
| 2017/0071566 A1 | 3/2017 | Hart et al. |
| 2017/0079868 A1 | 3/2017 | Reid, Jr. et al. |
| 2017/0100561 A1 | 4/2017 | Burnett |
| 2017/0128012 A1 | 5/2017 | Parks et al. |
| 2017/0136209 A1 * | 5/2017 | Burnett ................ A61M 1/84 |
| 2017/0156610 A1 | 6/2017 | Quackenbush et al. |
| 2017/0156611 A1 | 6/2017 | Burnett et al. |
| 2017/0160175 A1 | 6/2017 | Al-Mayah |
| 2017/0209048 A1 | 7/2017 | Wiita |
| 2017/0258345 A1 | 9/2017 | Smith |
| 2017/0259035 A1 | 9/2017 | Smith et al. |
| 2017/0273623 A1 | 9/2017 | Chen et al. |
| 2017/0273853 A1 | 9/2017 | Nagata et al. |
| 2017/0332955 A1 | 11/2017 | Burnett et al. |
| 2018/0049658 A1 | 2/2018 | Smith |
| 2018/0177458 A1 | 6/2018 | Burnett et al. |
| 2018/0184929 A1 | 7/2018 | Burnett et al. |
| 2018/0311469 A1 | 11/2018 | Wiita |
| 2018/0326190 A1 | 11/2018 | Nash |
| 2018/0344183 A1 | 12/2018 | McKinney et al. |
| 2018/0344184 A1 | 12/2018 | McKinney et al. |
| 2018/0344234 A1 | 12/2018 | McKinney et al. |
| 2018/0344249 A1 | 12/2018 | McKinney |
| 2018/0344250 A1 | 12/2018 | McKinney et al. |
| 2019/0133460 A1 | 5/2019 | Wine |
| 2019/0133532 A1 | 5/2019 | Zaiken |
| 2019/0150801 A1 | 5/2019 | Suehara |
| 2019/0282109 A1 | 9/2019 | Schlumpf et al. |
| 2019/0321588 A1 | 10/2019 | Burnett et al. |
| 2019/0343445 A1 | 11/2019 | Burnett et al. |
| 2019/0350634 A1 | 11/2019 | Jung |
| 2020/0029906 A1 | 1/2020 | Smith et al. |
| 2020/0046237 A1 | 2/2020 | Stimpson |
| 2020/0069332 A1 | 3/2020 | Callery |
| 2020/0085378 A1 | 3/2020 | Burnett et al. |
| 2020/0164184 A1 | 5/2020 | McKinney et al. |
| 2020/0197019 A1 * | 6/2020 | Harper ................ A61M 25/1011 |
| 2020/0237242 A1 | 7/2020 | Kaluzny et al. |
| 2020/0253536 A1 | 8/2020 | McKinney |
| 2020/0305742 A1 | 10/2020 | Ghodsain |
| 2020/0324037 A1 | 10/2020 | Bloomberg et al. |
| 2020/0383703 A1 | 12/2020 | Atad |
| 2020/0384241 A1 | 12/2020 | Herrera |
| 2021/0000422 A1 | 1/2021 | McKinney |
| 2021/0046277 A1 | 2/2021 | Samoocha |
| 2021/0052873 A1 | 2/2021 | Geva |
| 2021/0128413 A1 | 5/2021 | Elia |
| 2021/0177355 A1 | 6/2021 | Govari |
| 2021/0187240 A1 | 6/2021 | Waitkus |
| 2021/0244912 A1 | 8/2021 | Paz |
| 2021/0290243 A1 | 9/2021 | Franklin |
| 2021/0369185 A1 | 12/2021 | Janssen |
| 2022/0039751 A1 | 2/2022 | Chey |

FOREIGN PATENT DOCUMENTS

| | | | |
|---|---|---|---|
| CN | 204582261 | 8/2015 | |
| CN | 105073040 | 11/2015 | |
| CN | 205649494 | 10/2016 | |
| EP | 0097454 | 1/1984 | |
| EP | 3656297 | 5/2020 | |
| WO | WO 94/02195 | 2/1994 | |
| WO | WO 1995/012351 | 5/1995 | |
| WO | WO 2005/013834 | 2/2005 | |
| WO | WO-2005013834 A1 * | 2/2005 | ....... A61B 17/12099 |
| WO | WO 2006/060248 | 6/2006 | |
| WO | WO 2011/053500 | 5/2011 | |
| WO | WO 2012/006624 | 1/2012 | |
| WO | WO 2012/006625 | 1/2012 | |
| WO | WO 2012/122267 | 9/2012 | |
| WO | WO 2014/043650 | 3/2014 | |
| WO | WO 2014/160300 | 10/2014 | |
| WO | WO 2014/210453 | 12/2014 | |
| WO | WO 2015/191125 | 12/2015 | |
| WO | WO 2016/049654 | 3/2016 | |
| WO | WO 2016/204631 | 12/2016 | |

(56) References Cited

FOREIGN PATENT DOCUMENTS

| | | |
|---|---|---|
| WO | WO 2017/156451 | 9/2017 |
| WO | WO 2018/136306 | 7/2018 |
| WO | WO 2018/182913 | 10/2018 |

OTHER PUBLICATIONS

Rudra, Pallab, et al. "Recent Advances In Management of Pre-Eclampsia" Sep. 2011, British Journal of Medical Practitioners, vol. 4, No. 3 (Year: 2011).*
Extended European. Search Report mailed Mar. 2, 2020 for European Application No. EP 19210264.8.
A randomized comparison of microtip and air-charged catheter for the measurement of maximum urethral closure pressure, Ginekol Pol. 2012, 83: 586-589.
Abdominal pressure in the critically ill: measurement and clinical relevance, Intensive Care Med, 1999, 25: 1453-1458.
(Abstract only) "Caring for critically injured children: An analysis of 56 pediatric damage control laparotomies". J Trauma Acute Care Surg. May 2017; 82: 901-909.
(Abstract only) "Estimation of Intra-abdominal Pressure by Bladder Pressure Measurement: Validity and Methodology", The Journal of Trauma Injury, Infection, and Critical Care, Feb. 2001, 50: 297-302.
(Abstract only) "Intra-Abdominal Pressure Monitoring in Neonates", Pediatric Critical Car Med. Feb. 2016; 17: 172-173.
(Abstract only) "Saline volume in transvesical intra-abdominal pressure measurement: Enough is enough", Intensive Care Med., Mar. 2006; 32: 455-459.
De Waele J., et al., "Saline volume in transvesical intra-abdominal pressure measurement: Enough is enough", Intensive Care Med., Mar. 2006; 32: 455-459.
Determination of Intra-abdominal Pressure Using a Transurethral Bladder Catheter: Clinical Validation of the Technique, Anesthesiology, Jan. 1989, 70( 1 ), 47-50.
European Search Report EP 20850354.0 Dated Jul. 15, 2022.
European Search Report EP 20850354, Dated Oct. 6, 2022.
International search report and written opinion for international application PCT/US2018/028687 mailed Sep. 28, 2018.
International search report and written opinion for international application PCT/US2018/028693 mailed Sep. 28, 2018.
International search report for international application PCT/US2018/032467 mailed Sep. 5, 2018.
International search report for international application PCT/US2018/034781 mailed Sep. 5, 2018.
Is clinical examination an accurate indicator or raised intra-abdominal pressure in critically injured patents? CJS, Jun. 2000, 43, No. 3: 207-211.
Mark A. Fusco, et al., "Estimation of Intra-abdominal Pressure by Bladder Pressure Measurement: Validity and Methodology", The Journal of Trauma Injury, Infection, and Critical Care, Feb. 2001, 50: 297-302.
Measurement on intra-abdominal pressure in large incisional hernia repair to prevent abdominal compartmental syndrome, G Chir, Jan.-Feb. 2016; 37: 31-36.
Miguel A. Villalobos, et al., "Caring for critically injured children: An analysis of 56 pediatric damage control laparotomies". J Trauma Acute Care Surg. May 2017, 82: 901-909.
Mudit Mathur, MD, "Intra-Abdominal Pressure Monitoring in Neonates", Pediatric Critical Car Med. Feb. 2016; 17: 172-173.
Pressure Measurement Techniques for Abdominal Hypertension: Conclusions from an Experimental Model, Crit Care Res Pract., May 2015: 278139.
Product information for Intra Compartment Pressure Wick's / Slit Catheter Set up (Stryker).
Product information for Intra-Compartmental Pressure Monitor System (Stryker).
Product information for Your Continuous Pressure Monitoring System (Mammendorfer Institut für Physik und Medizin GMbH).
Prospective Study of Intra-Abdominal Hypertension and Renal Function after Laparotomy, British Journal of Surgery, 1999, 82, 235-238.
Study of the occurrence of intra-abdominal hypertension and abdominal compartment syndrome in patients of blunt abdominal trauma and its correlation with the clinical outcome in the above patents, World J Emerg Surg. Feb. 11, 2016; 11: 9.
The Measurement of Intra-Abdominal Pressure as a Criterion of Abdominal Re-exploration, 1984 Ann Surg., 199: 28-30.
"The neglected role of abdominal compliance in organ-organ interactions", Critical Care. Mar. 2016; 1-10.
User's Manual for Compartmental Pressure Monitoring System. For continuous measurement of intra compartment pressure (Synthes).
EP Search Report 18725349, Dated Dec. 10, 2023.
EP Exam Report EP18733733.2 Dated—Nov. 6, 2024.
Betty Shamaev & May Shoshan, Bones: Custom cushioning helps heal a bad break, May 14, 2015, Science New Explores, health & Medicine, https://www.snexplores.org/article/bones-custom-cushioning-helps-heal-bad-break#:~:text=Two%20teens%20designed%20this,an%2associated%20cast%20(left), 2015 (Year: 2015).
Millar Micro-Tip® Pressure Transducer, Apr. 15, 2005, Millar Micro-Tip® Pressure Transducer, https://www.harvardapparatus.com/media/Harvard/pdf/BS4_J_5.pdf, 2005 (Year: 2005).

* cited by examiner

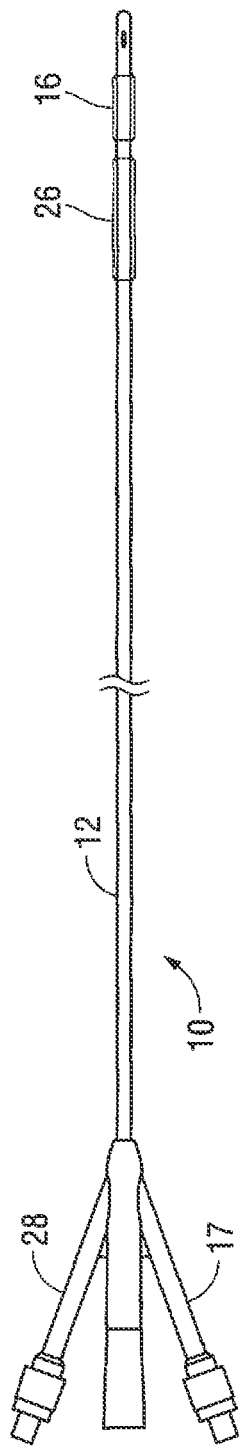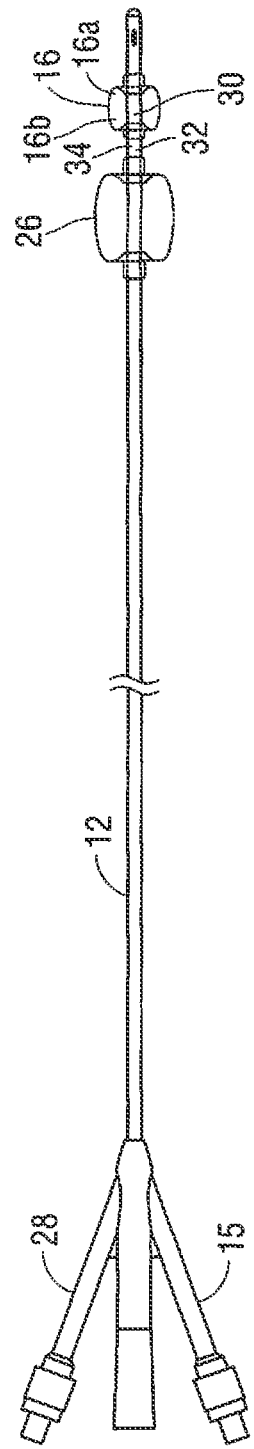

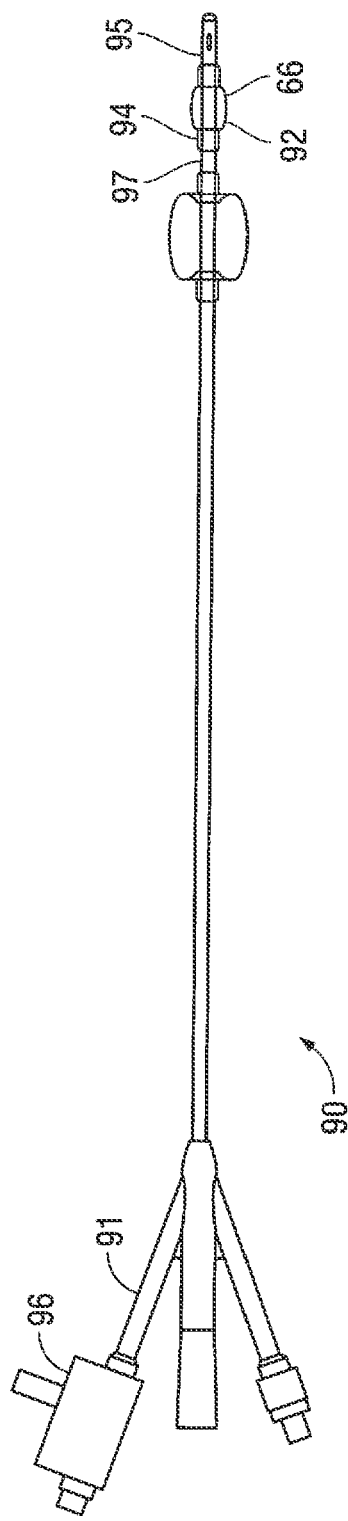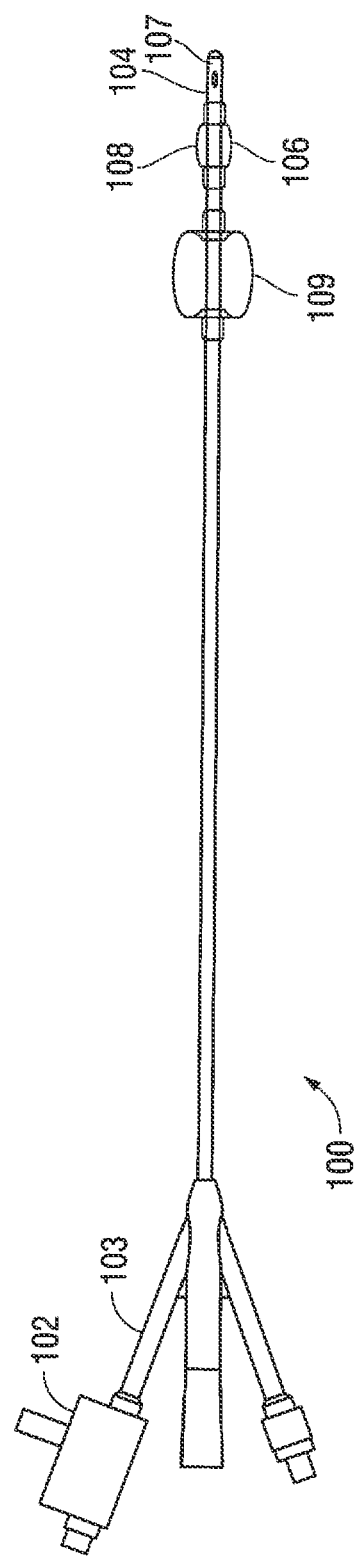

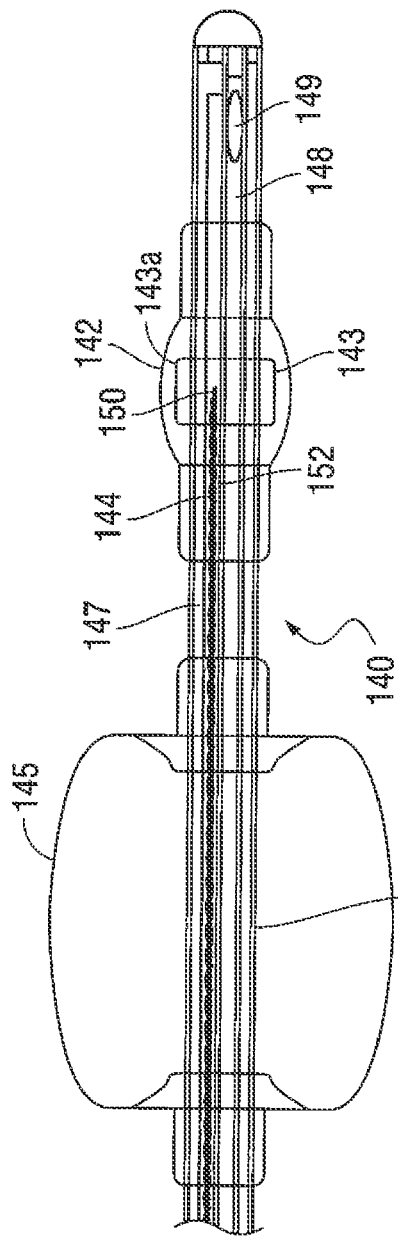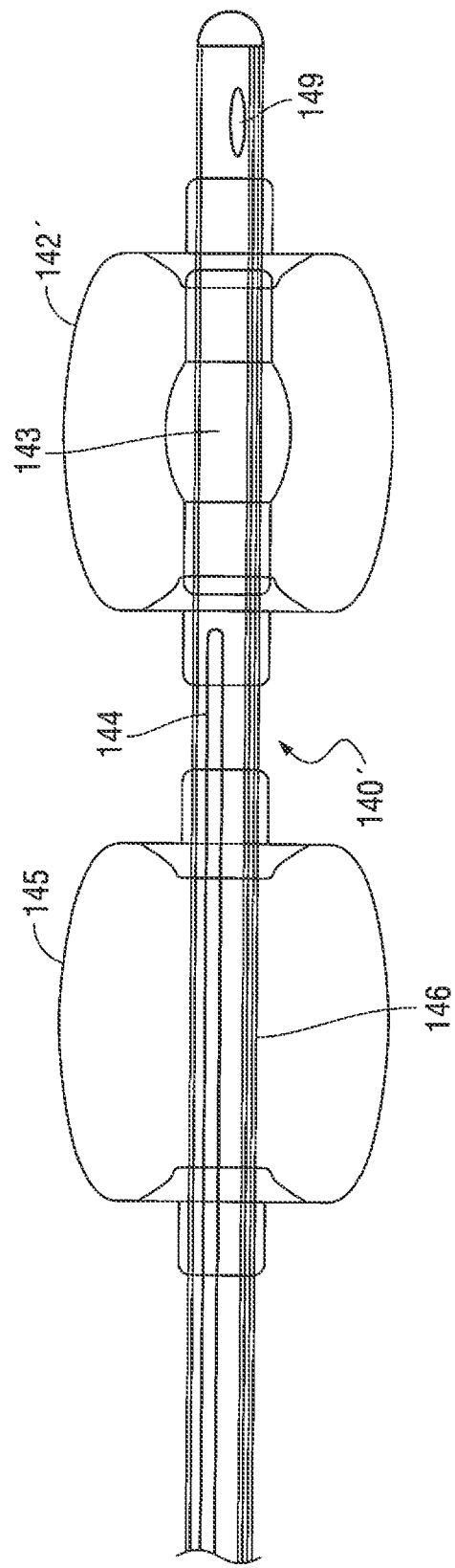
FIG. 15
FIG. 16

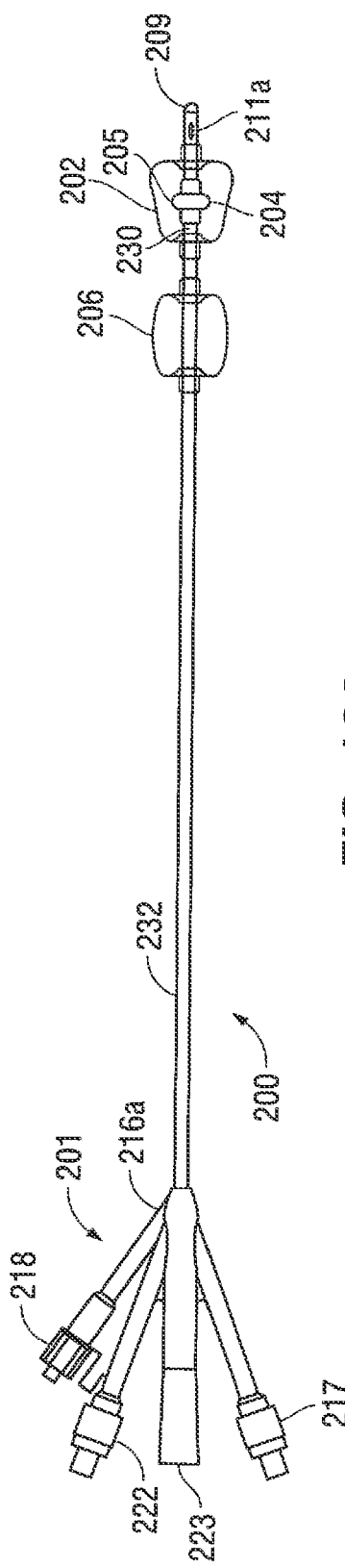
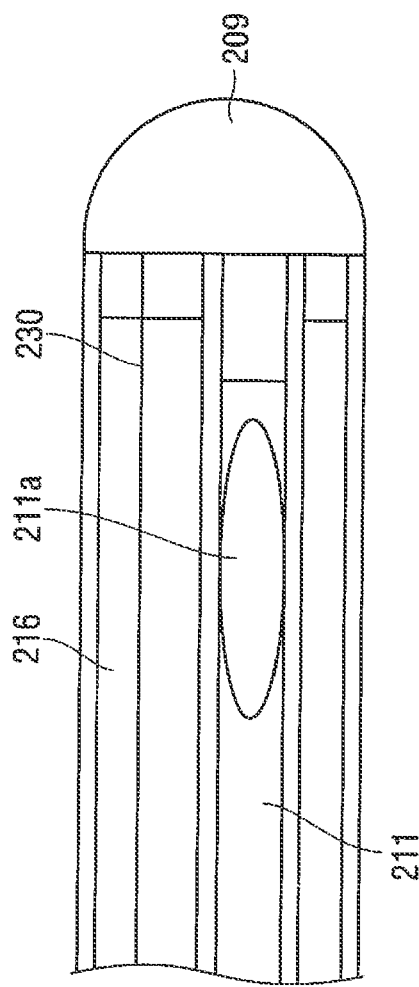
FIG. 18A
FIG. 18B

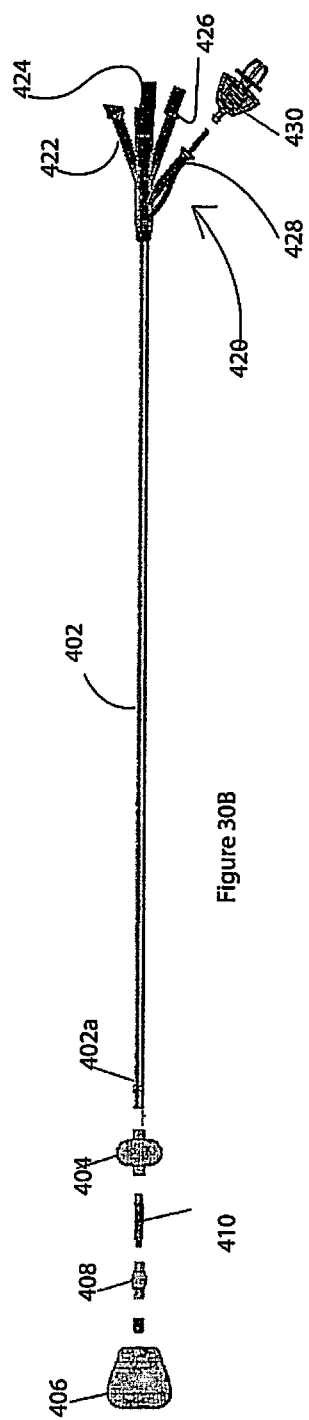

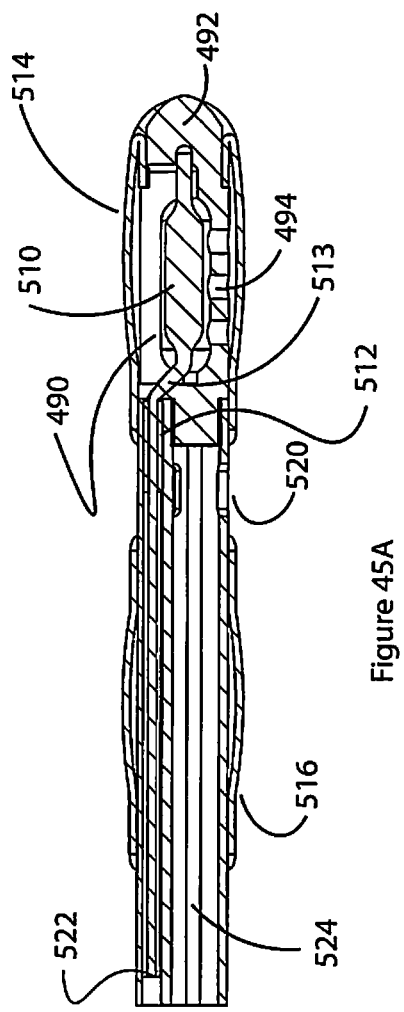
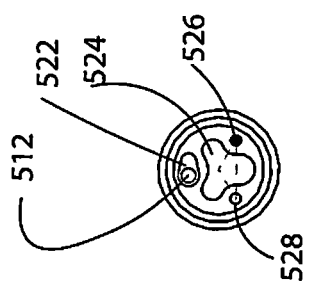
Figure 45A
Figure 45B

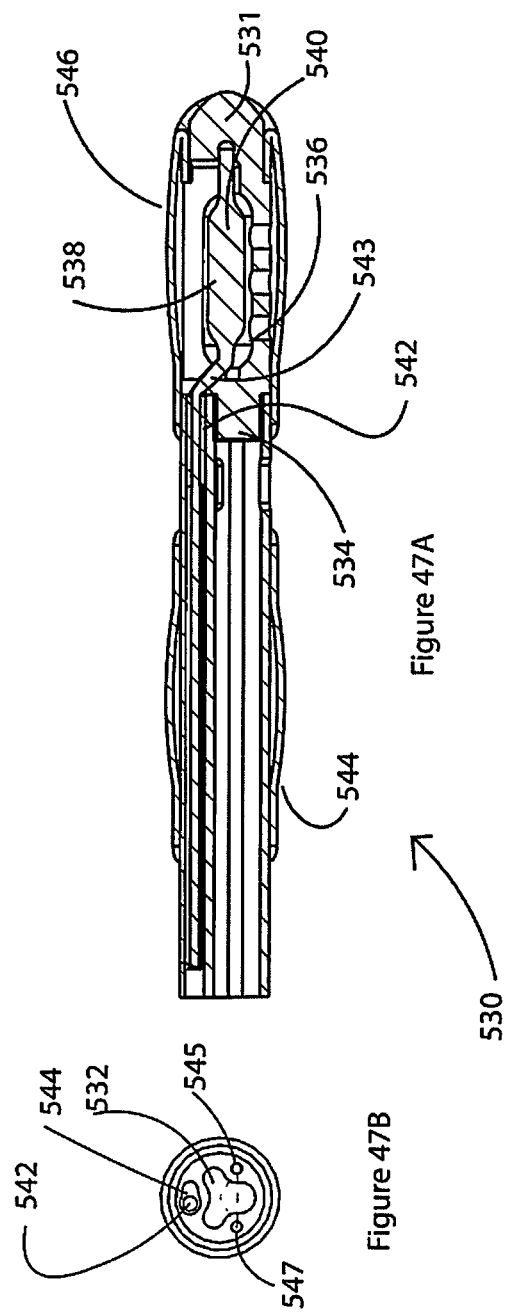

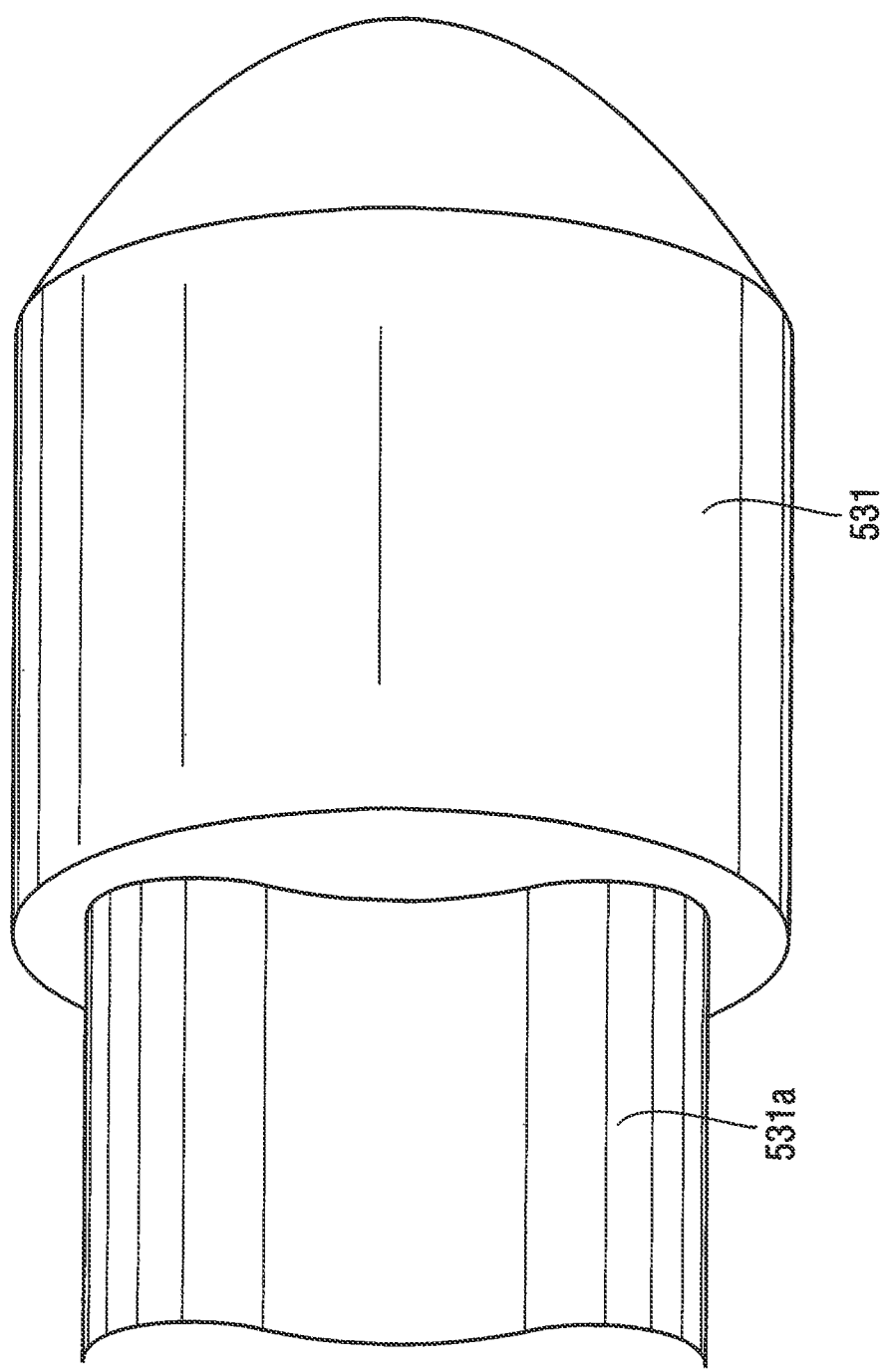

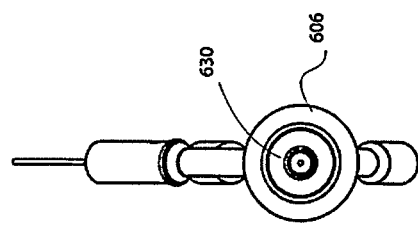
Figure 53
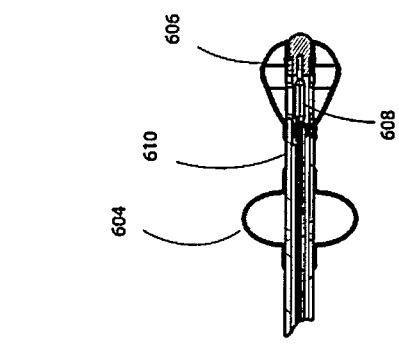
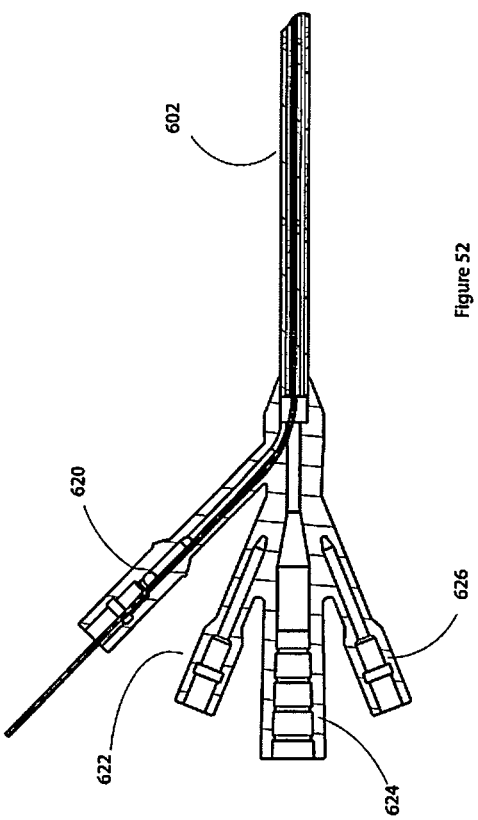
Figure 52

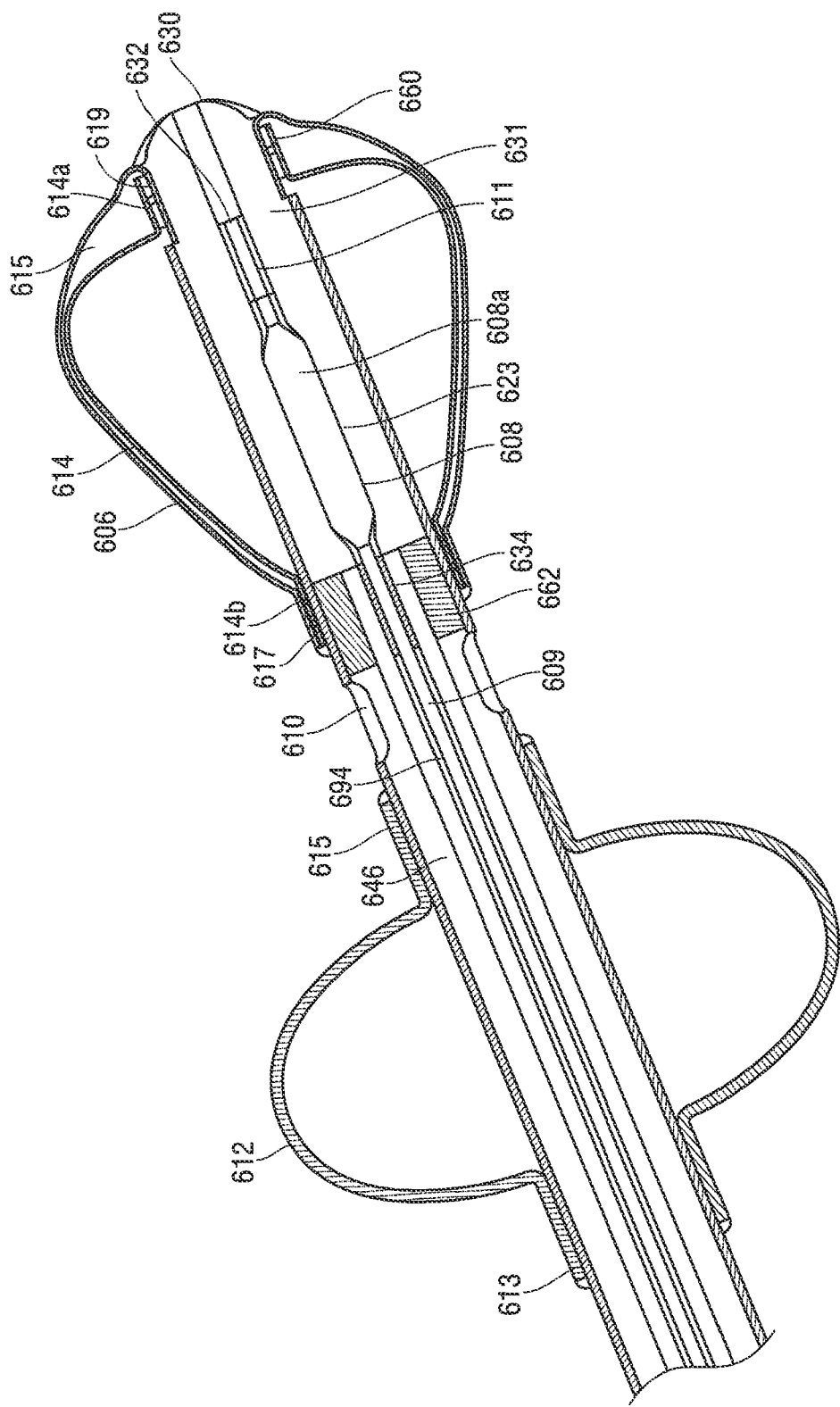

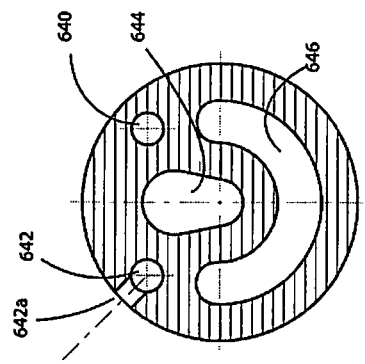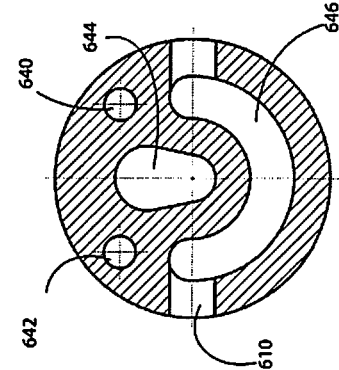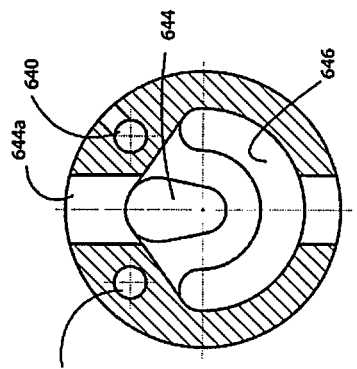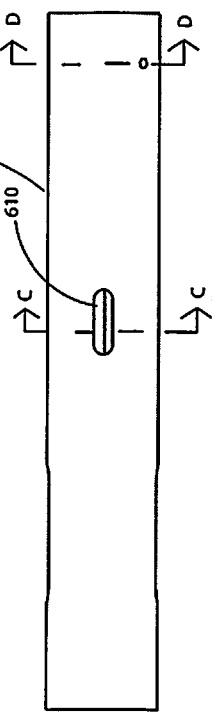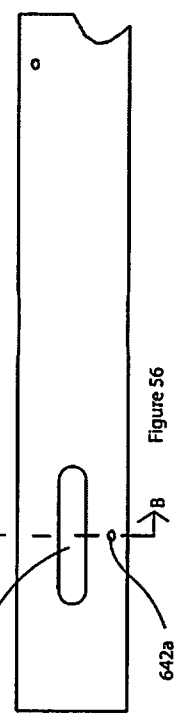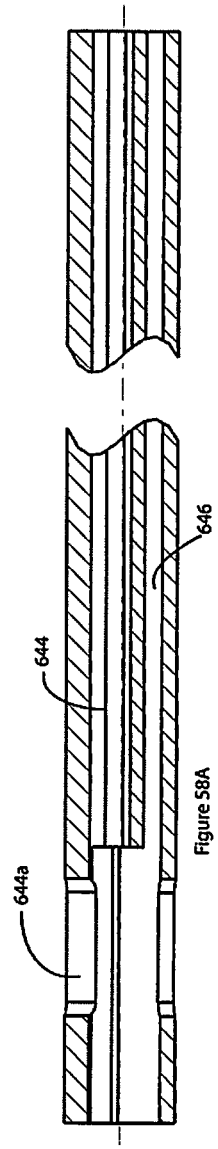

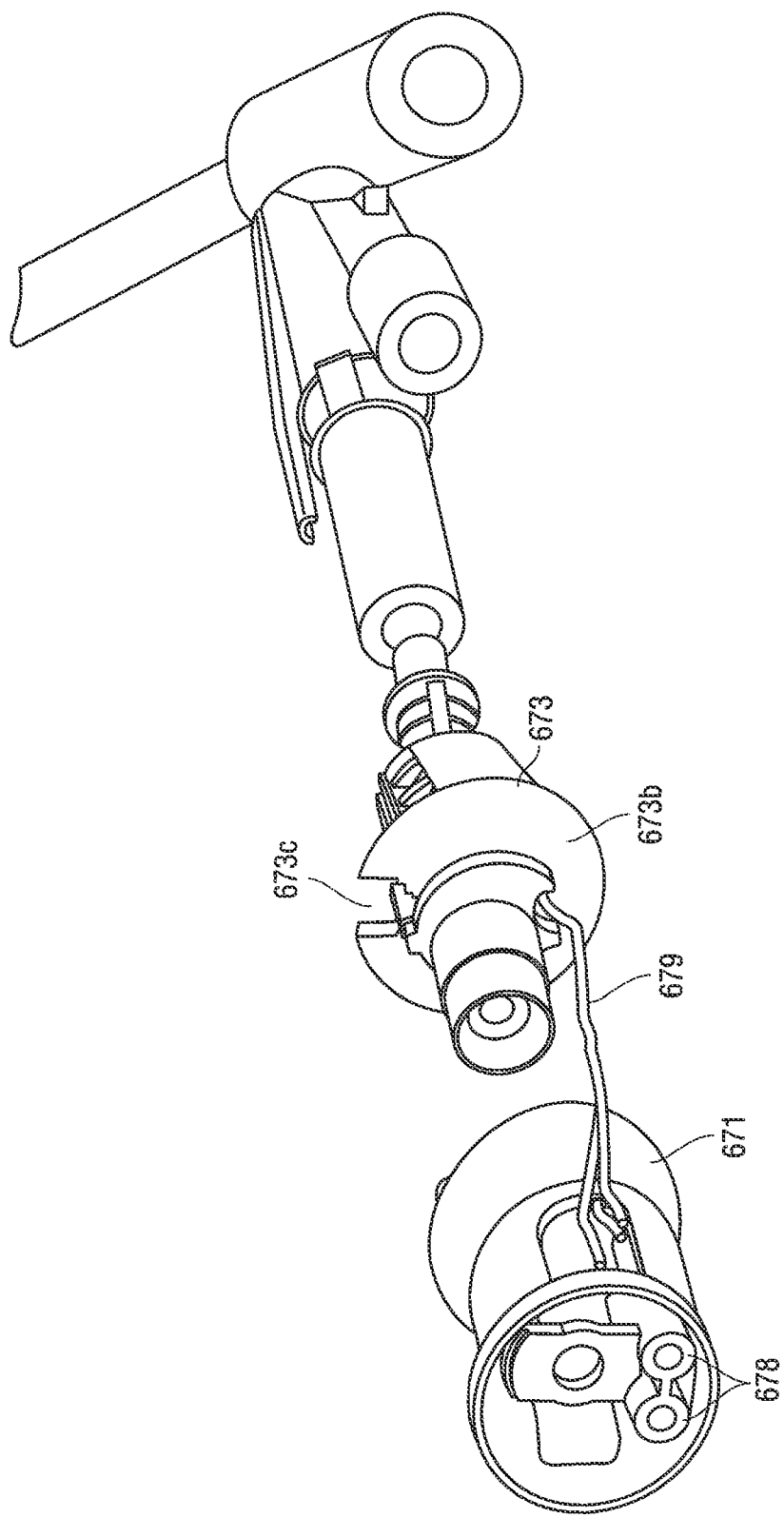

CATHETER FOR MONITORING INTRA-ABDOMINAL PRESSURE FOR ASSESSING PREECLAMPSIA

BACKGROUND OF THE INVENTION

This application is a continuation of U.S. application Ser. No. 16/752,578, filed on Jan. 24, 2020, which claims priority from provisional application 62/803,284, filed Feb. 8, 2019, the entire contents of which are incorporated herein by reference.

1. FIELD OF THE INVENTION

This application relates to a device and method for monitoring intra-abdominal pressure through the urinary bladder, and more specifically for monitoring intra-abdominal pressure in pregnant women to reduce adverse outcomes attributable to preeclampsia.

2. BACKGROUND

Traditionally, physicians relied on visual cues or physical examination to detect increase in intra-abdominal pressure (IAP). More recently Dr. Kirkpatrick and colleagues, in an article "Is Clinical Examination an Accurate Indicator of Raised Intra-Abdominal Pressure in Critically Injured Patients," CJS, June 2000, 43, No. 3, 207-211, showed that IAP measured through the patient's bladder was significantly more accurate than physical examination. That is, it was demonstrated that the clinical abdominal examination was insensitive and inaccurate when compared with urinary bladder pressure measurements.

Various tools for measuring IAP have been developed over the years. Many researchers have documented IAP measurements through almost every natural or manmade orifice in the body. Earlier crude forms of measuring IAP used bladder catheters, nasogastric tubes, and rectal tubes attached to a manometer. The nasogastric or the rectal route was better suited in rare cases of bladder rupture or situations where bladder catheters were contraindicated. However, due to local interferences, the nasogastric and the rectal tube measurements were neither reproducible nor logical as were the bladder catheters.

Thus, measuring of IAP through the bladder became more suitable. In 1989 Iberti and colleagues in an article entitled, "Determination of Intra-abdominal Pressure Using a Transurethral Bladder Catheter: Clinical Validation of the Technique," Anesthesiology, January 1989, 70(1), 47-50, validated the correlation of IAP using a catheter inserted in the bladder. Their study was key in using bladder pressure as the gold standard for measuring IAP. In 1995, Kron and colleagues published a study in "The Measurement of Intra-Abdominal Pressure as a Criterion for Abdominal Re-exploration, 1984 Ann Surg., 199, 28-30, comparing catheters in various body locations for measuring IAP. They measured IAP from the stomach using a nasogastric tube, from the rectum using a modified rectal tube, from the bladder using a modified bladder catheter, and direct abdominal pressure using a laparoscopic insufflator needle. They found that the bladder catheter had the best measurement of IAP and that the gastric and the rectal catheter measurements were less reliable due to dependence on the position of the catheter. Thus, clinicians generally agreed that the urinary bladder is the best-suited location for measurement of IAP.

The need for measuring IAP has become more important as physicians increasingly realized that organ failure and death were directly related to increase in IAP in certain high-risk patients. High abdominal pressure has been found to cause a decrease in function of the intestines, liver and blood vessels resulting in adverse consequences for the patients. Consequently, accurate measurement of IAP can help decrease patient morbidity and mortality. It has also been more recently discovered that pediatric and neonate population may also have need for IAP measurement to determine specific conditions.

Currently, there are few products available on the market to measure the IAP through the bladder. One device, the Bard IAP device, has a "valve clamp" which diverts urine from the main catheter drainage channel to measure IAP via converting hydrostatic pressure to a readable pressure gauge. This mechanism of IAP measurements is archaic and does not provide continuous pressure measurement when used with the standard 2-channel bladder drainage catheter. Two other manufacturers, Holtech and ConvaTec, also use a column of urine by connecting their kit to an existing bladder catheter. Their systems are cumbersome and the IAP readings are also not continuous. Biometrix has developed an IAP monitoring device which like other manufacturers relies on tapping into the main bladder drainage catheter, using a valve to measure the hydrostatic pressure. In 2008 Sugrue and colleagues, in an article "Prospective Study of Intra-Abdominal Hypertension and Renal Function after Laparotomy, British Journal of Surgery, 1999, 82, 235-238, suggested the use of 3-channel bladder drainage catheter so that the smaller channel, which was used for bladder irrigation, could be used to attach a pressure-monitoring device. The use of an extra channel made it possible to have continuous bladder drainage while measuring the bladder pressure. However, this bladder catheter did not provide a continuous pressure read because intermittently the operator needed to add 50 ml of water or saline to the bladder to record the IAP pressure. Thus, the pressure reading at best was intermittent since pressure readings were not performed when fluid was being added to the bladder. Consequently, although this was a step toward increasing the amount of pressure readings/recordings, it still was unable to conduct continuous pressure monitoring. Furthermore, it was still the same cumbersome IAP device set up which required a skilled person to add water before each IAP reading. Control of the amount of water added is critical since adding too much water to the bladder can falsely increase the pressure readings and also increase infection risk, thus further complicating the use.

It has also been recognized that most patients that have a need for measurement of IAP also need to have continuous drainage of the urinary bladder and thus devices need to account for this process.

Consequently, current devices placed in the bladder for measuring pressure require a continuous water column to maintain pressure readings. Thus, they fail to measure IAP continuously but only measure pressure intermittently. They also all rely on tapping into an existing bladder drainage catheter, which adds complications. Furthermore, they do not reduce the complexity of the procedure since they require constant retrograde insertion of a relatively large amount of fluid into the bladder, e.g., 50 cc, which increases the ICU workload. Still further, these devices increase the risk of complications and infections associated with fluid injection into the bladder. Fluid injection is also complicated since it needs to be closely monitored since too much fluid in the bladder can give false elevation of IAP readings, causing clinicians to take unnecessary steps in response to what is mistakenly believed is excess IAP.

It would therefore be advantageous to provide a device insertable into the bladder that accurately measures abdominal pressure without requiring adding water to the bladder to obtain such pressure readings. Such device would advantageously avoid the complications and risks associated with such fluid insertion. Furthermore, it would be advantageous if such device could continuously measure bladder pressure without interruption. This would advantageously enable a constant monitoring of IAP so critical time periods are not missed. It would further be advantageous to provide a device that improves the accuracy of the pressure reading in the bladder to more accurately determine IAP so necessary steps can be taken to address IAP only when warranted. Still further, it would be advantageous if such device could satisfy the foregoing needs and provide these enumerated advantages while being simple to use so that so that any of clinical staff with basic knowledge of bladder catheter insertion will be able to insert the device without relying on specially trained staff members.

Pre-eclampsia is a disorder that occurs during pregnancy that affects both the mother and unborn baby. It is a syndrome of cardio-vascular hypertension and maternal systemic inflammatory response that affects multiple organ systems (renal, hepatic, pulmonary, cerebral, placental). It is a rapidly progressive condition that is characterized by high blood pressure. Globally, pre-eclampsia and other hypertension disorders of pregnancy are a leading cause of maternal and infant illness and death. Being very common and very serious, it is estimated that about one woman dies from it every seven minutes somewhere in the world, and their baby often dies also. Pre-eclampsia is a major contributor to adverse maternal and fetal long-term and short-term outcomes, complicates approximately 2.7-8.2 percent of pregnancies worldwide, and affects hundreds of thousands of women and their families. Pre-eclampsia remains a leading cause of maternal, perinatal and infant morbidity and mortality, and contributes to an estimated 76,000 pre-eclampsia related maternal deaths and 500,000 perinatal deaths every year globally. In addition to being a leading global cause of maternal morbidity and mortality, pre-eclampsia is the second most common cause of preterm birth and infant mortality. Prior preterm delivery is in fact the only factor to surpass pre-eclampsia for cause of preterm births in any pregnancy. Not only is preterm birth associated with immediate neonatal morbidity, but it also has been linked to remote cardiovascular and metabolic disease in newborns.

Data from the National Center for Health Statistics and the National Hospital Discharge Survey show a consistent, approximate 25% increase in the diagnosis of pre-eclampsia over the last two decades with a worrisome trend toward more severe disease. Clinicians and researchers surmise that this increase mirrors the rising prevalence of obesity, diabetes, and chronic hypertension within the pregnant population—all known risk factors for pre-eclampsia. This trend is of concern for a sustained increase in pre-eclampsia rates. Therefore, there is a growing need to introduce new diagnostic testing in the care of pregnant women to reduce adverse outcomes specifically attributable to pre-eclampsia.

It is currently believed that the placenta mediates the systemic inflammatory response characteristic of pre-eclampsia but the etiology and exact pathways remain an enigma. Intra-abdominal hypertension (IAH) (pressure>12 mmHg) is well published in the areas of critical care and surgery, but not in pregnancy. IAH and pre-eclampsia culminate in death due to multiple organ failure if unattended, and definitive treatment for both involves the process of abdominal decompression (surgical and delivery, respectively). However, it is currently believed that delivery of the placenta is what cures pre-eclampsia, and abdominal decompression at birth has not been considered a potential mechanism.

Despite decades of research, the specific etiology of preeclampsia and its complete pathogenesis remain unknown. Poor identification of the progression of pre-eclampsia and the risks of adverse outcomes can lead to unnecessary intervention (e.g. preterm delivery). Moreover, the delay of diagnosis and management has the potential to negatively affect pregnancy outcomes.

Consequently, the need exists to improve diagnosis of pre-eclampsia so appropriate intervention can be taken to reduce the foregoing risks associated with pre-eclampsia which would lower health risks, reduce pre-term births and save lives of the mothers and babies.

SUMMARY

The present invention overcomes the deficiencies and disadvantages of the prior art. The present invention advantageously provides a multi-lumen catheter insertable into the bladder in the same manner as a regular bladder drainage catheter to determine intra-abdominal pressure without requiring insertion of water into the bladder. The catheters of the present invention utilize a gas-charged chamber to measure bladder pressure across a large surface area, and thus, accurately determine intra-abdominal pressure, and enable pressure to be measured continuously without interrupting urine flow and without interruptions to add water to the bladder.

Some embodiments of the catheter of the present invention utilize a stabilizing balloon to help retain the catheter in the bladder during the procedure.

In accordance with another aspect of the present invention, a method is provided for measuring intra-abdominal pressure in a pregnant woman to assess occurrence or likelihood of pre-eclampsia, the method comprising the steps of:

providing a catheter having first and second lumens and a balloon;

inserting the catheter into a bladder of the mother;

injecting gas into the first lumen of the catheter to expand the balloon from a deflated condition to a more inflated condition, an internal space of the balloon and the first lumen forming a closed gas chamber;

obtaining a first pressure reading of the bladder based on deformation of the balloon to thereby monitor pressure within an abdomen of the mother to assess if pre-eclampsia is occurring or likely to occur; and transmitting the first pressure reading to an external monitor connected to the catheter, the pressure reading indicative of the presence and/or risk of pre-eclampsia to determine when intervention should occur to prevent morbidity and mortality of the woman and baby.

In accordance with another aspect of the present invention, a method for measuring intra-abdominal pressure in a pregnant woman to assess occurrence or likelihood of pre-eclampsia is provided, the method comprising the steps of:

providing a catheter having first and second lumens and a pressure sensor;

inserting the catheter into a bladder of the woman;

obtaining a first pressure reading of the bladder based on the pressure sensor to thereby monitor pressure within an abdomen of the woman to assess if pre-eclampsia is occurring or likely to occur; and transmitting the first pressure reading to an external monitor connected to the catheter, the pressure reading indicative of the presence and/or risk of pre-eclampsia to determine when intervention should occur to prevent morbidity and mortality of the woman and baby.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIG. 1A is a side view of a first embodiment of the catheter of the present invention having a pressure balloon, a stabilizing balloon and a sensor positioned in the air lumen, both balloons shown in the deflated (collapsed) condition;

FIG. 1B is a side view similar to FIG. 1A showing the two balloons in the inflated (expanded) condition;

FIG. 11 is a side view of another alternate embodiment of the catheter of the present invention having two balloons, a sensor in the air lumen and an external transducer, the two balloons shown in the inflated condition;

FIG. 12 is a side view of another alternate embodiment of the catheter of the present invention having two balloons, a temperature sensor in the air lumen and the pressure sensor external of the catheter, the two balloons shown in the inflated condition;

FIG. 15 is a side view of another alternate embodiment of the catheter of the present invention having an outer and inner pressure balloon and a stabilizing balloon, the balloons shown in the inflated condition;

FIG. 16 is a side view similar to FIG. 15 illustrating an alternate embodiment having a larger outer balloon;

FIG. 18A is a side view of another alternate embodiment of the catheter of the present invention having a port for connection to an external pressure transducer and an outer and inner pressure balloon, the two balloons shown in the inflated condition;

FIG. 18B is close up view of the distal end of the catheter of FIG. 18A;

FIG. 30B is an exploded side view of the catheter of FIG. 30A;

FIGS. 32A, 32B, 32C and 32D illustrate the manufacturing steps of assembly of the catheter of FIG. 30A wherein FIG. 32A shows the connecting pin inserted into the catheter shaft; FIG. 32B shows the inner balloon attached to the connecting pin; FIG. 32C shows the distal tip connected to the pin; and FIG. 32D shows the outer balloon attached to the shaft and distal tip;

FIG. 45A is a longitudinal cross-sectional view of the distal region of a catheter containing the chamber of FIG. 42;

FIG. 45B is a transverse cross-sectional view taken along line A-A of FIG. 45A;

FIG. 47A is a longitudinal cross-sectional view of the distal region of an alternate embodiment of the catheter of the present invention;

FIG. 47B is a transverse cross-sectional view taken along line A-A of FIG. 47A;

FIG. 48B is a perspective view of the distal tip of the catheter of FIG. 48A;

FIG. 52 is a cross-sectional view of the catheter of FIG. 50A;

FIG. 53 is a front view of the catheter of FIG. 50A;

FIG. 54 is a cutaway side view illustrating the inside of a catheter similar to the catheter of FIG. 50A;

FIG. 56 is a side view of a portion of the shaft of the catheter of FIG. 50A showing the openings for communicating with the outer wall of the inner balloon;

FIG. 57 is a side view of a portion of the shaft of the catheter of FIG. 50A showing the drainage opening;

FIG. 58A is a longitudinal cross-sectional view of the catheter shaft of FIG. 56;

FIG. 58B is a transverse cross-sectional view taken along line B-B of FIG. 56;

FIG. 58C is a transverse cross-sectional view taken along line C-C of FIG. 57;

FIG. 58D is a transverse cross-sectional view taken along line D-D of FIG. 57;

FIG. 66C is an exploded perspective of the connector of FIG. 64 showing the thermistor wires;

DETAILED DESCRIPTION OF PREFERRED EMBODIMENTS

Figure 2:
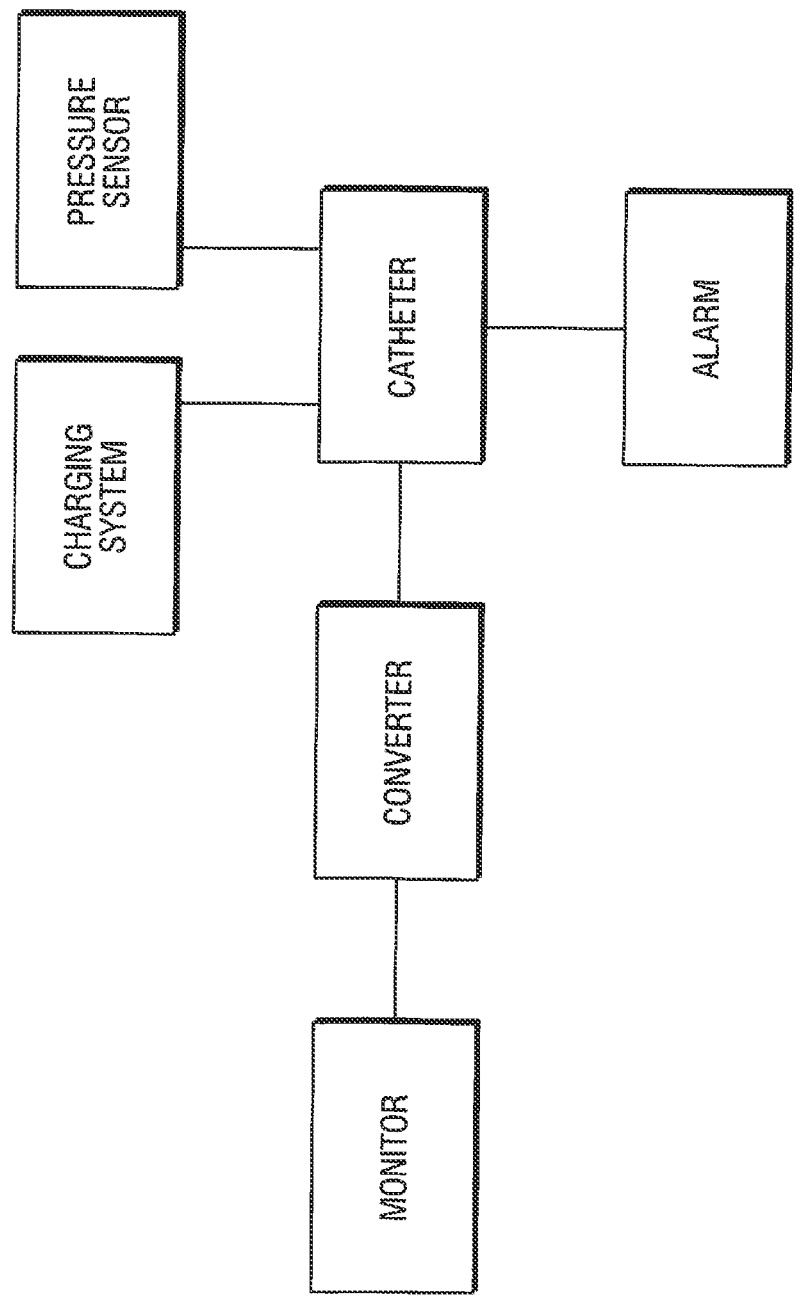
FIG. 2 is a schematic view of the system utilizing the catheter of FIG. 1A with an alarm system.

Increased abdominal pressure can cause many adverse conditions including diminishing the function of the intestines, liver, and blood vessels. Simply viewing or feeling the abdomen does not provide sufficient information or reading of health conditions.

It is recognized that urinary bladder pressure directly correlates to the intra-abdominal pressure. Although pressure readings can be determined by access to the esophagus or rectum, the bladder has been found to be the most accurate and the least invasive. In trauma or burn patients for example, time is critical and the less complicated the method for determining bladder pressure the better the clinical results.

The catheters of the present invention measure abdominal pressure via measurement of bladder pressure without filling the bladder with water. This avoids the risks associated with retrograde filling of the bladder with water as such retrograde filling not only increases the complications and workload for the intensive care (IC) staff and can create inaccuracies by providing false elevation of IAP readings, but can adversely affect the patient by increasing the risk of infection. Furthermore, by avoiding refilling of the bladder, bladder pressure can be measured continuously. This is because in devices requiring filling the bladder with water, water needs to be periodically added to the bladder to replace the water drained from the bladder and measurement readings are interrupted during water insertion. Due to these repeated interruptions, pressure cannot be read continuously. Note in some cases, as much as 50 cc of fluid needs to be repeatedly added to the bladder.

The catheters of the present invention efficiently and effectively measure bladder pressure without requiring filling the bladder with water. Also, as will become apparent from the discussion below, the catheters of the present invention provide a more accurate reading of pressure and enable continuous monitoring of the bladder pressure. This is all achieved in an easy to insert device.

It should be noted that the catheters of the present invention can be utilized for measuring other pressure in a patient and are not limited to intra-abdominal pressure.

Furthermore, in some embodiments, the catheter of the present invention provides a dual sensor to provide a backup pressure reading. In some embodiments, a dual pressure balloon arrangement is provided. These various embodiments are discussed in more detail below.

Referring now to the drawings and particular embodiments of the present invention wherein like reference numerals identify similar structural features of the devices disclosed herein, there is illustrated in FIGS. 1A-5 a catheter of a first embodiment of the present invention. The catheter (device) is designated generally by reference numeral 10 and is configured for insertion into and positioning within the bladder of the patient for measuring intra-abdominal pressure. This measurement is to check if the intra-abdominal pressure exceeds a specified threshold since if such threshold is exceeded, there is a risk to the patient as discussed above and steps need to be taken to reduce the pressure such as draining additional fluid from the abdomen, opening the abdomen, etc.

The catheter 10 of the present invention can in some embodiments include an alarm or indicator to alert the user if pressure within the bladder, which correlates to pressure within the abdomen, rises to an unacceptable level, i.e., beyond a threshold or predetermined value (pressure). The indicator or alarm can be on the catheter or alternatively on an external device such as the monitor as discussed in more detail below. The alarm can also be connected via wireless connection to a phone or remote device to alert the appropriate personnel. The indicator or alarm can alternatively or in addition be activated if a change in pressure measurement exceeds a specified rate over a specified period of time.

Turning now to details of the catheter 10, which is also referred to herein as the device 10, and with initial reference to Figures IA, 1B, 3 and 4 the catheter 10 of this embodiment has an elongated flexible shaft 12 having a lumen (channel) 14 extending within the shaft 12 and communicating at its distal region with balloon 16 to fluidly communicate with balloon 16 to inflate the balloon. Balloon 16 is utilized for monitoring pressure and is also referred to herein as the "pressure balloon." A fluid port 15 is positioned at a proximal region 17 of the catheter 10 for communication with an infusion source for infusion of gas, e.g., air, through the lumen 14 and into the balloon 16. The catheter 10 is shown in FIG. 1A with balloon 16 in the deflated condition (position) and in FIG. 1B with the balloon 16 in the inflated condition (position). The shaft 12 also includes a second lumen (channel) 20 and third lumen (channel) 24 extending therein (see also FIG. 5). In a preferred embodiment, the second lumen 20 is the largest lumen and is configured for continuous drainage of bodily contents from the bladder and can be connected to a drainage bag for collection of urine. Second lumen 20 has a side opening 22 at a distal portion, best shown in FIG. 3, communicating with the bladder. The third lumen 24 terminates at its distal end within balloon 26 to fluidly communicate with balloon 26 to inflate the balloon 26. The balloon 26 is inflatable to stabilize the catheter 10 to limit movement of the catheter 10 to keep it in place within the bladder and is also referred to herein as "the stabilizing balloon 26." A fluid port 28 is positioned at a proximal region 17 of the catheter 10 for communication with an infusion source for infusion of fluid through the lumen 24 and into the balloon 26. The balloon 26 can be filled with fluid, e.g., liquid such as water or saline, or a gas, e.g., air. In FIG. 1A, the balloon 26 is shown in the deflated condition and in FIG. 1B in the inflated condition.

Figure 5:
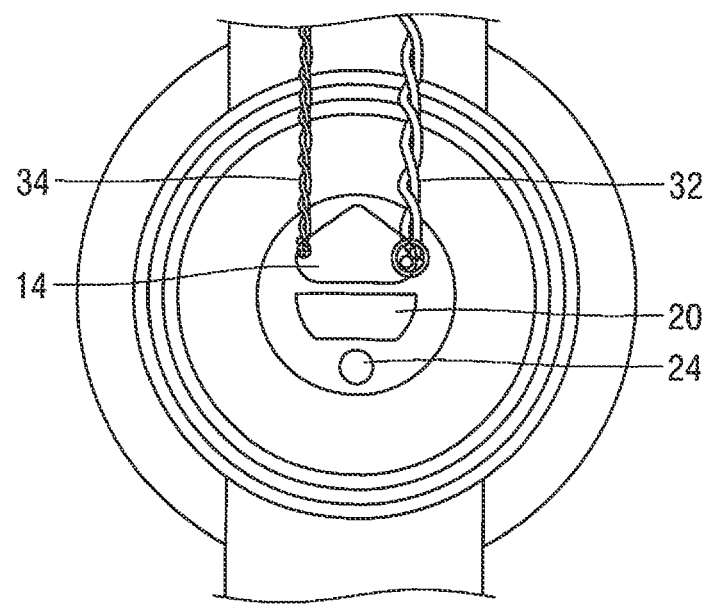
FIG. 5 is an enlarged transverse cross-sectional view of the catheter of FIG. 1.
Figure 6:
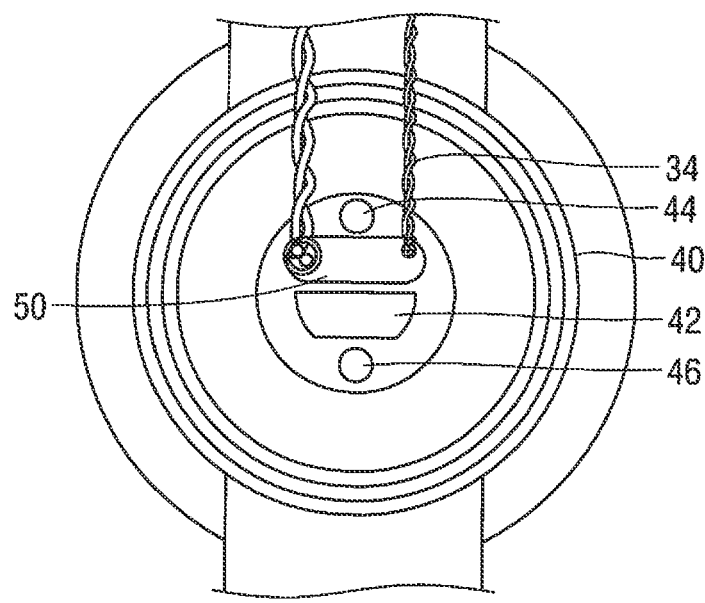
FIG. 6 is an enlarged transverse cross-sectional view of an alternate embodiment of a catheter of the present invention having four lumens.

Note FIG. 5 is a transverse cross-section of the catheter showing the three lumens of various shapes. These cross-sectional shapes of the lumens are provided by way of example as one or more of the lumens can be circular, oval or other symmetrical or asymmetrical shapes in transverse cross section. This also applies to the cross-sectional views of the other embodiments herein, e.g., FIGS. 6, 10B and 23, 30C, 45B, wherein the lumens can be shapes other than those shown. As noted above, preferably the drainage lumen is the largest lumen but in alternate embodiments one or more of the other lumens could be larger than the drainage lumen.

A sensor 30 is positioned within lumen 14 adjacent balloon 16. The wire(s) 32 are shown extending through lumen 14, the sensor 30 and wire(s) 32 being of sufficiently small size so as not to interfere with air flow though lumen 14. The sensor 30 measures pressure of the bladder. The sensor 30 is part of a transducer for converting the variation in pressure to an electrical signal for transmission to an external monitor. The pressure sensor also includes a temperature sensor to measure core temperature of the body as seen inside the bladder. Transmission wire(s) 34 of the temperature sensor extend adjacent wire 32 through lumen 14 and terminate external of the catheter 10 for connection to an external monitor. The transducer can be wired directly to the monitor or alternatively wired to a converter external of the catheter for converting the signal received by the transducer and transmitting a signal to the monitor, e.g., a bedside monitor, to display the pressure readings. This is shown schematically in FIG. 2. The readings can be displayed in quantitative form, graphical form or other displays to provide an indicator to the clinician of the bladder pressure. The monitor, or a separate monitor, will also display the temperature readings from sensor 30. Alternatively, the sensor/transducer can be connected to the monitor via a Bluetooth® wireless connection.

Wires 32 and 34 can extend though lumen 14 and exit side port 15 for connection to a converter or monitor or alternatively can be inserted through the lumen 14, piercing the wall to enter the lumen 14 distal of the side port.

An alarm system can also be provided wherein the system includes a comparator for comparing the measured pressure (and/or temperature) to a threshold (predetermined) value, and if such threshold is exceeded, an indicator, e.g., an alarm, is triggered to indicate to the hospital personnel the excessive pressure and/or temperature. An alarm system can alternatively or in addition be activated if a change in pressure measurement exceeds a specified rate over a specified period of time. This would alert the staff to an imminent risk of ACS prior to intra-abdominal pressure exceeding a certain value, e.g., 20 mm hg, since due to this link, the relationship between intra-abdominal pressure and abdominal cavity volume is believed to be linear up to an intra-abdominal pressure of 12-15 mm hg and increasing exponentially thereafter.

The alarm system can be part of the catheter (as shown in FIG. 2) or alternatively external to the catheter 10.

The lumen 14 and space 16*a* within balloon 16 together form a closed gas, e.g., air, chamber, i.e., the lumen 14 forming an air column. With the balloon 16 filled with air, pressure on the external wall of the balloon will force the balloon to deform inwardly, thereby compressing the air contained within the balloon space 16*a* and within the lumen 14. The pressure sensor 30 is located in a distal portion of the lumen 14 at the region of the balloon 16 and thus is positioned at the distal end of the air column. Therefore, the pressure is sensed at the distal region as the sensor 30 detects change in air pressure in lumen 14 due to balloon deformation. Placement of the sensor 30 at a distal location provides a pressure reading closer to the source which advantageously increases the accuracy because it reduces the risk of transmission issues by reducing the amount of interference which could occur due to water, air, clots, tissue, etc. if the transmission is down the air lumen (air column).

Additionally, the pressure measurement occurs about a more circumferential area of the balloon 16 providing a pressure reading of a region greater than a point pressure sensor reading. Also, average pressure over an area of the bladder wall can be computed. Thus, the area reading gleans information on pressure over more of the bladder wall. Stated another way, the balloon has a relatively large surface area with multiple reference points to contribute to average pressure readings of the surface around it by the sensor.

The air column is charged by insertion of air through the side port 15 which communicates with lumen 14. The side port 15 includes a valve to provide a seal to prevent escape of air from a proximal end. The balloon 16 can be composed of impermeable material, or in alternative embodiments, a permeable or semi-permeable material with an impermeable coating. This seals the air column at the distal end to prevent escape of air through the distal end, i.e., through the wall of the balloon 16. Thus, with the lumen sealed at the proximal and distal ends, a closed air system is provided, and without the requirement for repeated water insertion, a fully closed unit is provided.

In some embodiments, when the lumen 14 is air charged, the balloon 16 is not fully inflated. This improves the accuracy of the balloon 16 transmitting pressure from external the balloon to the interior of the balloon and into the lumen, i.e., air column, by ensuring the balloon has sufficient compliancy to prevent the balloon from introducing artifact into the pressure reading which would diminish its accuracy.

In some embodiments, the pressure balloon 16 is of a size to receive at least about 3 cc (3 ml) of fluid. However, other sizes/volumes are also contemplated such as about 2 cc or about 1 cc. Additionally, these volumes represent the maximum volume of fluid for the balloon, however, as noted above, in preferred embodiments, the pressure balloon 16 is not fully inflated so it would receive less than the maximum volume. Thus, with a balloon of X volume, the fluid would receive X-Y fluid, with Y representing the amount of desired extra space to achieved desired compliancy of the balloon while still enable sufficient inflation of the balloon to achieve its pressure induced deformation function.

Note in this embodiment, the stabilizing balloon 26 is positioned proximal of the pressure balloon 16. Also, in this embodiment, the stabilizing balloon 26 is larger than the pressure balloon 16. By way of example, the stabilizing balloon 26 can have a fully expanded diameter of about 23 mm and the pressure balloon 16 can have a fully expanded diameter of about 15 mm, although other dimensions or diameters for these balloons are also contemplated. By way of example, the stabilizing balloon 26 can have a capacity of about 10 cc (10 ml) of air, although other sizes/volumes are also contemplated. Note these sizes/volumes for both balloons are provided by way of example and other sizes are also contemplated. Alternatively, the stabilizing balloon can be the same size or smaller than the pressure balloon. Various shapes of the balloons are also contemplated.

Additionally, although the balloon 26 is positioned proximal of the balloon 16, it is also contemplated that the balloon 26 be positioned distal of balloon 16. The axial spacing of the balloons 16, 26 enable the stabilizing balloon 26 to engage the bladder wall to provide a sufficient radial force thereon for securing/mounting the catheter within the bladder without interfering with the function of balloon 16.

Figure 3:
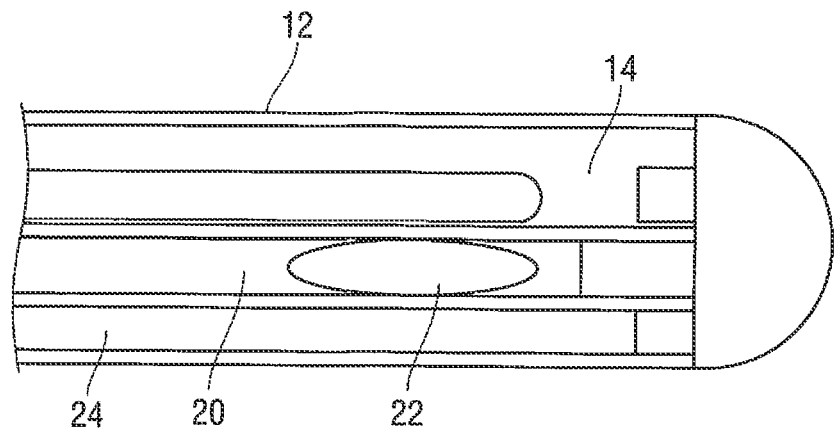
FIG. 3 is a close-up view of the tip of the catheter of FIG. 1A.
Figure 4:
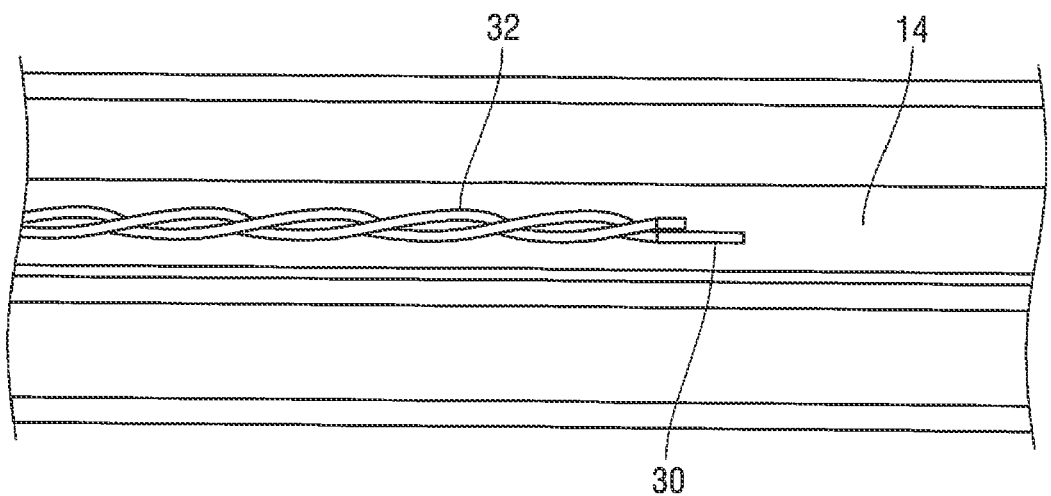
FIG. 4 is a close-up view of the sensor of FIG. 1A within the air lumen.
Figure 7:
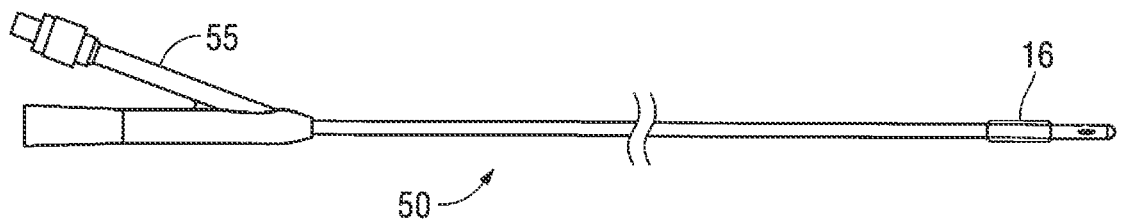
FIG. 7 is a side view of an alternate embodiment of the catheter of the present invention similar to FIG. 1A except having a single balloon, the balloon shown in the inflated condition.

It should be appreciated that although the stabilizing balloon is shown in the embodiment of FIG. 1, it is also contemplated as an alternative that the catheter and system of FIGS. 1 and 2 can be utilized without the stabilizing balloon 26 as shown for example in FIG. 7. Similarly, although the various embodiments (catheter) disclosed herein utilize a stabilizing balloon, it is also contemplated that alternatively the catheter of these various embodiments not include a stabilizing balloon. In the embodiment of FIG. 7, catheter 50 has two lumens: 1) a lumen for drainage of the bladder which has a side opening at a distal end to communicate with the bladder (similar to lumen 20 of FIG. 1A); and 2) an air lumen filling pressure balloon 16 via insertion of air through side port 55. The sensor 30 is positioned within the air lumen in the same manner as sensor 30 is in lumen 14 or in the alternative positions disclosed herein. Thus, the pressure and temperature sensing described in conjunction with FIG. 1 is fully applicable to the embodiment of FIG. 7. Besides the elimination of the stabilizing balloon and its lumen and side port, catheter 50 is the same as catheter 10, Note that although only one sensor is shown in FIG. 3, it is also contemplated that multiple sensors can be provided. Also, note that the sensor 30 is positioned in lumen 14 at a mid-portion of the balloon, i.e., just proximal where the opening in lumen 14 communicates with the interior 16*a* of the balloon 16. It is also contemplated that the sensor can be placed at another portion within the lumen 14, e.g., a more proximal portion, with respect to the lumen opening. Also, the lumen opening need not be at the mid portion of the balloon and can be at other regions of the balloon to communicate with the interior space 16*a*. Note if multiple sensors are provided, they can be positioned at various locations within the lumen 14.

As shown, the sensor 30 and its transmission wires are located in the same lumen 14 also used for initial inflation gas, e.g., air, for balloon 16 and for the air charged column. This minimizes the overall transverse cross-section (e.g., diameter) of the catheter 10 by minimizing the number of lumens since additional lumens require additional wall space of the catheter. However, it is also contemplated in an alternate embodiment that the sensor is in a dedicated lumen separate from the inflation lumen 14. This can be useful if a larger sensor or additional wires are utilized which would restrict the air lumen if provided therein. This is also useful if a specific sized lumen for the sensor and wires is desired to be different than the sized lumen for the air column. Provision of a separate lumen is shown in the cross-sectional view of FIG. 6 wherein in this alternate embodiment catheter 40 has four lumens: 1) lumen 42 for drainage of the bladder which has a side opening at a distal end to communicate with the bladder (similar to lumen 20 of FIG. 1); 2) lumen 44 for filling pressure balloon 16; 3) lumen 46 for filling stabilizing balloon 26; and 4) lumen 50 in which sensor 30 and its transmission wires 32 and temperature sensor wires 34 are contained. In all other respects catheter 40 is identical to catheter 10 and its balloons, air channel, sensor, etc. would perform the same function as catheter 10. Therefore, for brevity, further details of catheter 40 are not discussed herein as the discussion of catheter 10 and its components and function are fully applicable to the catheter 40 of the embodiment of FIG. 6. As noted above, the cross-sectional shapes of the lumens can be circular, oval, etc. or other shapes.

Turning now to the use of the catheter 10, the catheter 10 is inserted into the bladder. Note catheter 50 would be used in the same manner. The balloon 26 is inflated to secure the catheter 10 in place during the procedure by insertion of a fluid (liquid or gas) through side port 28 which is in fluid communication with lumen 24. The system is charged by inflation of the balloon 16, i.e., preferably partial inflation for the reasons discussed above, by insertion of air via a syringe through port 15 which is in fluid communication with lumen 14. As discussed above, the catheter 10 is a closed system with the balloon 16 sealed so that air inserted through lumen 14 and into balloon 16 cannot escape through balloon 16. Thus, a closed chamber is formed comprising the internal space 16*a* of the balloon 16 and the internal lumen 14 communicating with the internal space 16*a* of balloon 16. With the balloon 16 inflated, pressure monitoring can commence. When external pressure is applied to an outer surface 16*b* of the balloon 16, caused by outward abdominal pressure which applies pressure to the bladder wall and thus against the wall of balloon 16, the gas e.g., air, within the chamber is compressed. The sensor 30 at the distal end of lumen 14 provides continuous pressure readings, converted to an electrical signal by the transducer within the distal end of lumen 14, and then electrically communicates through wire(s) 32 extending through lumen 14, exiting through the proximal side port 15 and connected to an external monitor. Note the wire can terminate at the proximal end in a plug in connector which can be connected directly to the monitor or alternatively plugged into a converter to convert the signals from the transducer wherein in the embodiments wherein the converter is interposed between the wires and monitor (see e.g., the system of FIG. 2) to provide the aforedescribed graphic display. Although, the system is capable of continuous pressure and temperature monitoring, it can also be adapted if desired for periodic monitoring so the pressure and temperature readings can be taken at intervals or on demand by the clinician.

In the embodiments wherein an indicator is provided, if the measured pressure exceeds a threshold value, and/or a change in pressure measurement exceeds a specific rate over a specific time period, the indicator would alert the clinician, e.g., via a visual indication or an audible indication that the threshold is exceeded. The indicator in some embodiments can include an audible or visual alarm (shown schematically in FIG. 2). In the embodiments having an indicator, the indicator can be provided on a proximal end of the catheter which extends out of the patient or the indicator can be part of an external component such as the monitor or a separate alarm system. A visual, audible, or other indicator can likewise be provided in any of the other embodiments disclosed herein to indicate if the measured temperature exceeds a predetermined value, and such indicator can include an alarm and can be part of the catheter or a separate component.

Figure 8A:
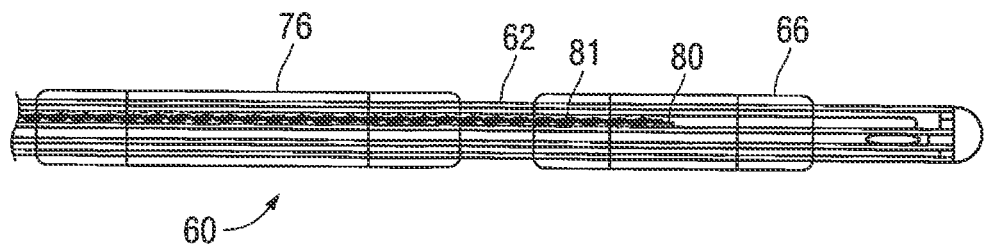
FIGS. 8A and 8B are side views of an alternate embodiment of the catheter of the present invention having two balloons and a pressure sensor and a separate temperature sensor in the air lumen, the two balloons shown in the deflated condition, with FIG. 8A showing the distal end and FIG. 8B showing the proximal end of the catheter.

In the embodiment of FIGS. 1-7, within the distal end of the air lumen 14 is a pressure transducer and pressure sensor 30 which also includes a temperature sensor. In the alternate embodiment of FIGS. 8A-10B, the temperature sensor is separate from the pressure sensor. More specifically, catheter 60 has an elongated flexible shaft 62 having a lumen (channel) 64 extending within the shaft 62 and fluidly communicating at a distal region with balloon 66 to inflate the balloon. Balloon 66 (also referred to as the pressure balloon) is utilized for monitoring pressure. A fluid side port 65 is positioned at a proximal region 67 of the catheter 60 for communication with an infusion source for infusion of gas e.g., air, through the lumen 64 and into the balloon 66. The catheter 60 is shown in FIG. 8A with balloon 66 in the deflated condition (position) and in FIG. 9 with the balloon 66 in the inflated condition (position). The shaft 62 also includes a second lumen (channel) 70 and third lumen (channel) 74 extending therein. The second lumen 70 is preferably the largest lumen and is configured for drainage of the bladder. Second lumen 70 has a side opening 72 at a distal portion communicating with the bladder. The third lumen 74 communicates at a distal region with stabilizing balloon 76 to fluidly communicate with balloon 76 to inflate the balloon. The stabilizing balloon 76 is inflatable to stabilize the catheter 60 to limit movement of the catheter 60 to keep it in place within the bladder. A side fluid port 75 is positioned at a proximal region 67 of the catheter 60 for communication with an infusion source for infusion of fluid through the lumen 74 and into the balloon 76.

Figure 9:
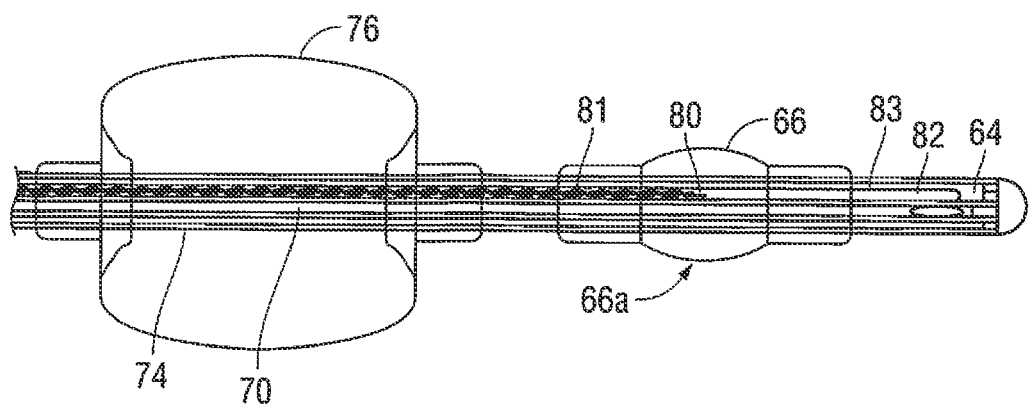
FIG. 9 is a side view similar to FIG. 8A showing the two balloons in the inflated condition.
Figure 10A:
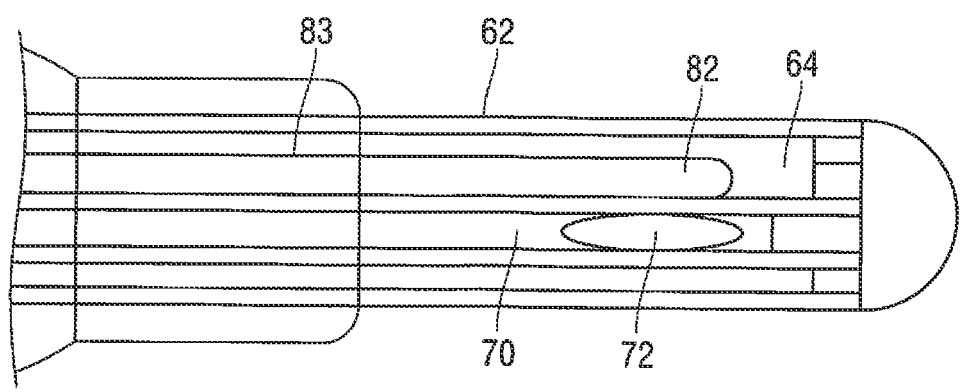
FIG. 10A is a close up view of the distal portion of the catheter of FIG. 8A.
Figure 10B:
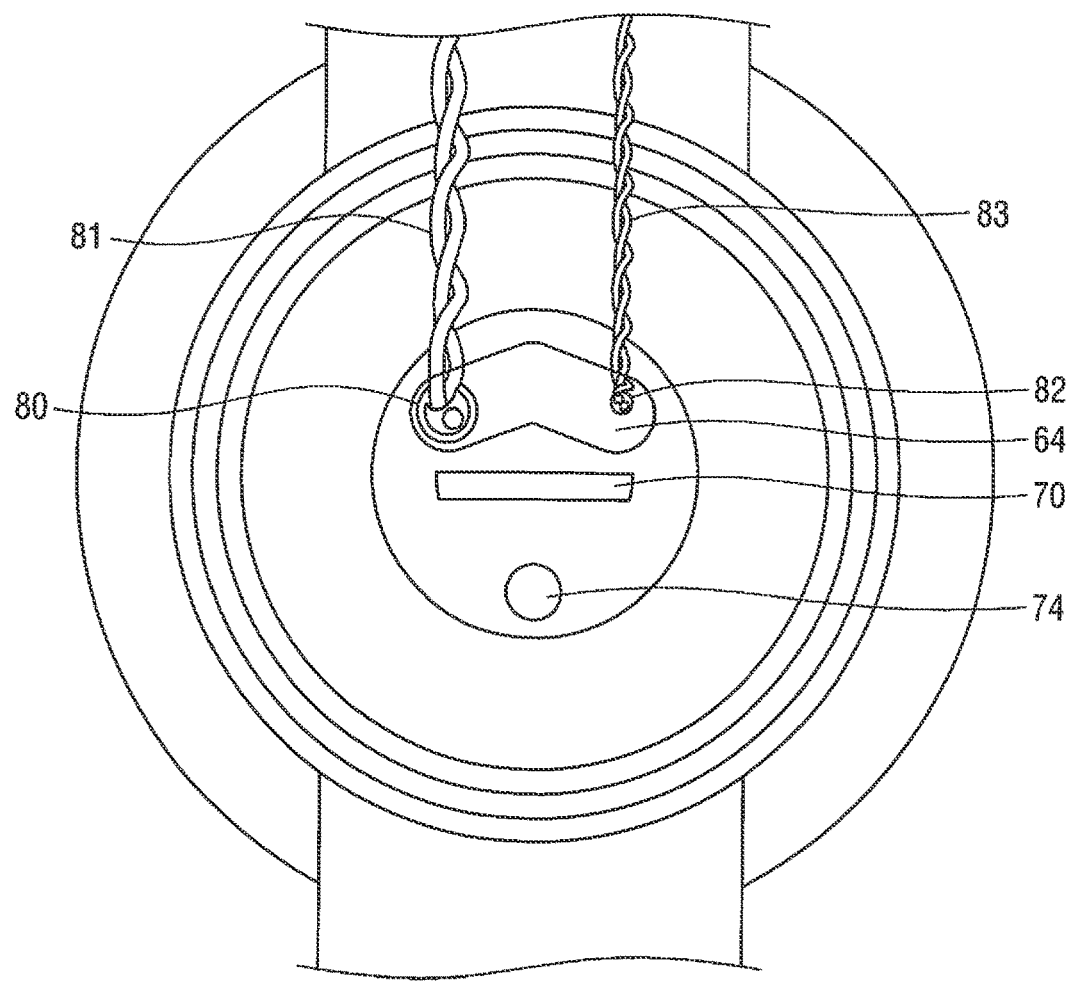
FIG. 10B is an enlarged transverse cross-sectional view of the catheter of FIG. 8A.

Sensor 80 is positioned in lumen 64 for sensing pressure in response to balloon deformation in the same manner as sensor 30. Sensor 82 is positioned in lumen 64 distal of sensor 80 for measuring core temperature. Temperature sensor 82 can be a thermocouple, a thermistor or other types of temperature sensors. As shown in FIG. 9, the temperature sensor is distal of the balloon 66 and its transmission wire(s) 83 extend proximally within lumen 64, exiting a proximal end (through side port 65) for communication with a monitor or alternatively a converter which communicates with the monitor. Wire(s) 81 of sensor 80 also extends through lumen 64, alongside wire 83, exiting through the side port 65 or a proximal end wall or a side wall of the lumen. It is also contemplated that alternatively one or both of sensors 80 and 82, and their associated wires 81, 83, can be positioned in a separate "fourth" lumen such as in the embodiment of FIG. 6 so that the "inflation lumen" and the "sensor lumen" are independent.

In use, catheter 60 is inserted into the bladder and stabilizing balloon 76 is inflated to secure the catheter 60 in place. The system is charged by inflation of the balloon 66, i.e., preferably partially inflated for the reasons discussed above, by insertion of gas, e.g., air, through port 65 which is in fluid communication with lumen 64 in a closed system formed by the internal space 66a of the balloon 66 and the internal lumen 64 communicating with the internal space 66a of balloon 66. With the balloon 66 inflated, pressure monitoring can commence as external pressure applied to an outer surface of the balloon 66 compresses the gas within the chamber. The sensor 80 at the distal end of lumen 64 provides continuous pressure readings, converted to an electrical signal by the transducer within the distal end of lumen, and then electrically communicates through wires 82 extending through lumen 64 to an external monitor either directly or via a converter. The sensor 82 at the distal end of lumen 64 provides continuous temperature readings via wires 83 communicating directly or indirectly with the monitor, Although, the system is capable of continuous pressure and continuous temperature monitoring, as with the other systems disclosed herein, it can also be adapted if desired for periodic monitoring so the pressure and/or temperature readings can be taken at intervals or on demand by the clinician.

Figure 8B:
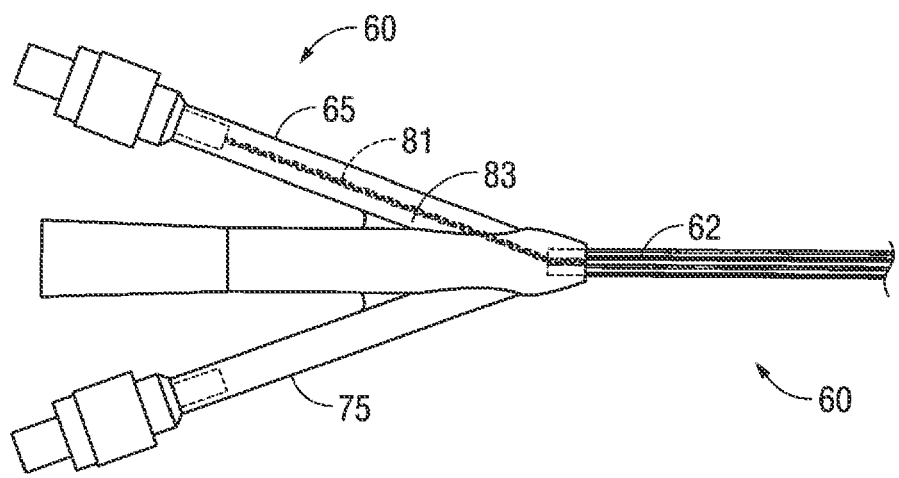

In the alternative embodiment of FIG. 11, catheter 90 is identical to the catheter 60 of FIG. 8 except that the pressure transducer is positioned external of the catheter rather than in the air (or other gas) lumen. That is, instead of the pressure transducer including the sensor being positioned within the distal end of the air lumen, the pressure sensor 92 is positioned within lumen 94 at the distal end of the lumen and transmission wire(s) 93 connect the sensor 92 to the pressure transducer 96 positioned outside of the patient at a proximal region of catheter 90. As shown, the pressure transducer 96 can be positioned in a side port of catheter 90. In alternate embodiments, it is positioned outside the catheter. The temperature sensor 95 is positioned within lumen 94 along with transmission wire 97 in the same manner as temperature 82 and wires 83 are positioned in catheter 60 described above. The temperature sensor 95 can be a separate sensor positioned distal of the pressure sensor 92 as shown or alternatively it can be part of sensor 92 as in the embodiment of FIG. 1. In all other respects, catheter 90 is identical to catheter 60 and therefore for brevity further discussion is not provided since the structure and function of the balloons, the lumens, the positioning of the sensors in the lumens, the continuous pressure monitoring, etc., as well as the aforedescribed alternative arrangements of catheter 60, are fully applicable to the catheter 90.

In the alternative embodiment of FIG. 12, catheter 100 is identical to catheter 60 of FIG. 8 except that the pressure transducer and pressure sensor are positioned external of the patient at a proximal region of the catheter rather than in the air lumen. That is, instead of the pressure transducer sensor being positioned within and at the distal end of the air lumen, the transducer and pressure sensor 102 are positioned at a side port 103 of the catheter 100. In alternative embodiments, they are positioned outside the catheter. In yet other embodiments, the pressure sensor and/or pressure transducer can be positioned within the air (or other gas) lumen at a proximal end of the air lumen. The temperature sensor 107 is positioned within lumen 104 along with transmission wire(s) 108 in the same manner as temperature sensor 82 and wire 83 are positioned in catheter 60 described above. The system is charged by inflation of the balloon 106, i.e., preferably partially inflated for the reasons discussed above, by insertion of air via a syringe or other injection device through the side port 103 which is in fluid communication with lumen 104. The catheter 100 is a closed system with the balloon 106 sealed so that air inserted through lumen 104 and into balloon 106 cannot escape through balloon 106. Thus, a closed chamber is formed comprising the internal space of the balloon 106 and the internal lumen 104 communicating with the internal space of balloon 106. With the balloon 106 inflated, pressure monitoring can commence. When external pressure is applied to an outer surface of the balloon 106, caused by outward abdominal pressure which applies pressure to the bladder wall and thus against the wall of balloon 16, the gas (e.g., air) within the chamber of the balloon 106 is compressed. This compresses the air within the lumen 104 creating an air charged column along the lumen 104. The sensor 102 at the proximal end of catheter 100 measures pressure of the air column at its proximal end and can provide continuous pressure readings, converted to an electrical signal by the transducer at the proximal end or external of the catheter 100, and then electrically communicates through wire(s) to an external monitor. The balloon 106, like balloon 16, balloon 66 and the other pressure balloons described herein, is of sufficiently large size to provide a sufficient circumferential area for detection of pressure changes along several parts of the bladder wall, thereby providing an average pressure and enabling more accurate pressure readings. Balloon 109 is a stabilizing balloon like balloon 76 inflated through a separate lumen.

Note the wire(s) of the sensor 102 can terminate at the proximal end in a plug in connector which can be connected directly to the monitor or alternatively plugged into a converter to convert the signals from the transducer in the embodiments where the converter is interposed between the wires and monitor (see e.g. the system of FIG. 2) to provide the aforedescribed graphic display. Although, the system is capable of continuous pressure and temperature monitoring, it can also be adapted if desired for periodic monitoring so the pressure and/or temperature readings can be taken at intervals or on demand by the clinician. In all other respects, catheter 100 is identical to catheter 60 and therefore for brevity further discussion is not provided since the structure and function of the balloons, the continuous pressure monitoring, etc., as well as the aforedescribed alternative arrangements of catheter 60, are fully applicable to the catheter 100.

Figure 13A:
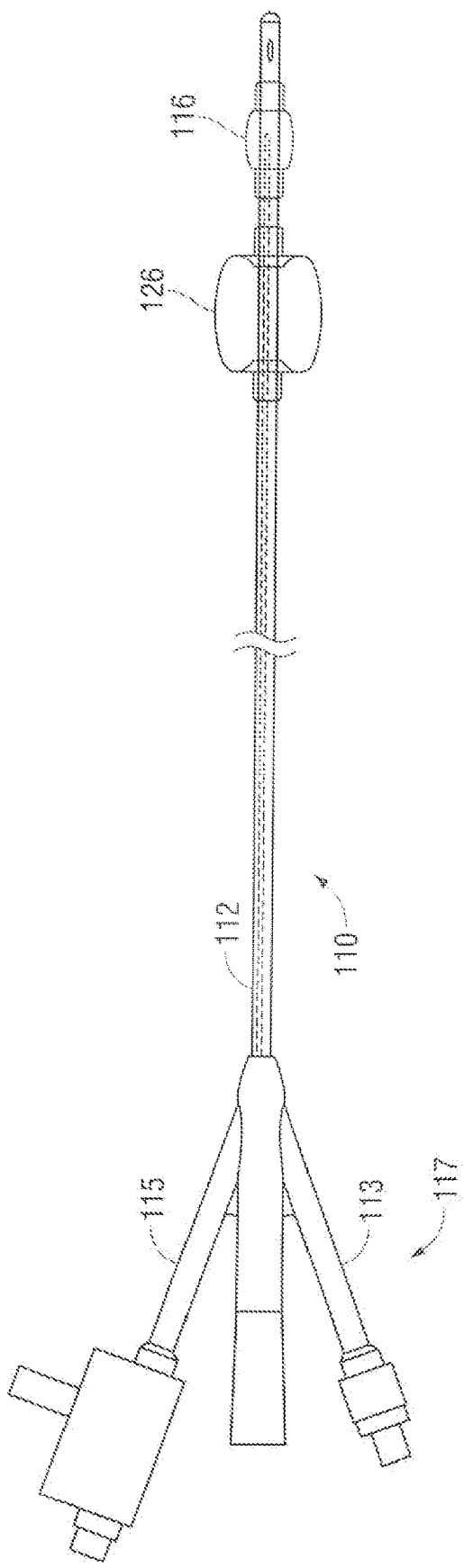
FIG. 13A is a side view of another alternate embodiment of the catheter of the present invention having two balloons and a pressure sensor positioned within the pressure balloon, the two balloons shown in the inflated condition.
Figure 13B:
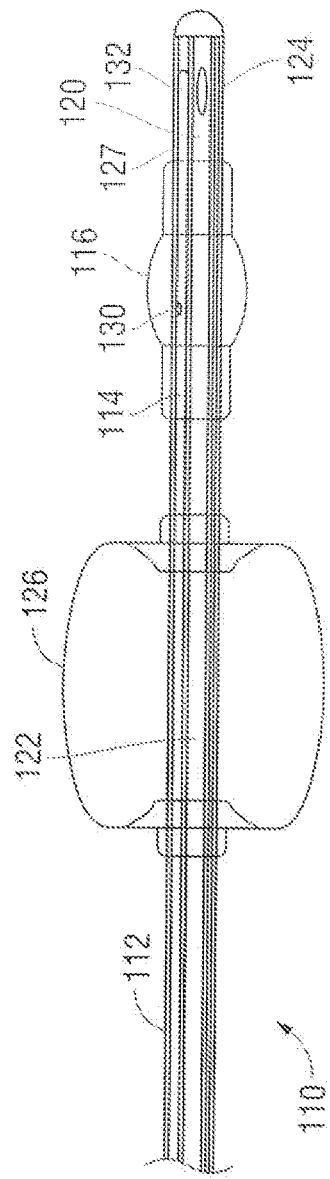
FIG. 13B is an enlarged view of the distal portion of the catheter of FIG. 13A.

FIGS. 13A and 13B illustrate an alternate embodiment wherein catheter 110 includes a pressure sensor within the balloon. More specifically, catheter 110 has an elongated flexible shaft 112 having a lumen (channel) 114 extending within the shaft 112 and communicating at its distal region with balloon 116 to fluidly communicate with balloon 116 to inflate the balloon. Balloon 116 (also referred to as the pressure balloon) is utilized for monitoring pressure. A fluid side port 115 is positioned at a proximal region 117 of the catheter 110 for communication with an infusion source for infusion of gas through the lumen 114 and into the balloon 116. The shaft 112 also includes a second lumen (channel) 120 and third lumen (channel) 122 extending therein. Second lumen 120 has a side opening 124 at a distal portion communicating with the bladder. The third lumen 122 communicates at a distal region with stabilizing balloon 126 to fluidly communicate with balloon 126 to inflate the balloon to limit movement of the catheter 110 to keep it in place within the bladder for drainage. A fluid port 113 is positioned at a proximal region 117 of the catheter 110 for communication with an infusion source for infusion of fluid through the lumen 122 and into the balloon 126.

The pressure sensor 130 is carried by catheter 110 and positioned within the balloon 116 to measure pressure in response to deformation of the balloon in response to pressure exerted on an outer wall of balloon 116. The pressure transducer can include the sensor 130 or can be a separate component positioned at a proximal end of the catheter external of the catheter 110. The temperature sensor 132 can be positioned within the balloon 116, can be part of sensor 130, or alternatively positioned within lumen 114 (as shown in FIG. 13B), with its transmission wire(s) 127 extending within the gas, e.g., air, lumen 114 along with the wires of sensor 130 in the same manner as in catheter 60 described above.

In all other respects, catheter 110 is identical to catheter 60 and therefore for brevity further discussion is not provided since the structure and function of the balloons, lumens, continuous pressure monitoring, etc. as well as the aforedescribed alternative arrangements of catheter 60, are fully applicable to the catheter 110.

As discussed above, the pressure balloons disclosed herein have a large circumferential area (and large volume) to provide multiple reference points for pressure readings and to provide an average pressure to enable more accurate readings. Thus, the pressure balloon provides for gross measurement. In an alternate embodiment shown in FIG. 15, the pressure balloon for detecting pressure, designated by reference numeral 142, forms an outer balloon of catheter 140. Contained within the outer balloon 142 is an inner balloon 143. The inner balloon 143 provides a smaller diameter balloon and a smaller circumference (and volume) than the outer balloon 14. The inner balloon 143 together with the lumen 144 forms a smaller gas, e.g., air, column than in the embodiments discussed above where the larger balloon internal space communicates directly with the air lumen. This provides finer measurements. Thus, the compliant outer balloon 142 compresses the compliant inner balloon 143 which compresses the air within air lumen 144. The closed system is thereby formed by the internal space of the inner balloon 143 and the lumen 144. In certain instances, the smaller balloon air column can provide a more accurate reading from the average pressure determined by the larger outer balloon 142.

The inner balloon 143 and outer balloon 142 can be separately/independently inflated and closed with respect to each other so there is no communication, e.g. passage of gas or liquid, between the inner and outer balloons 143, 142.

In the embodiments disclosed herein having inner and outer balloons, the outer balloon acts a medium of transmission to the inner pressure balloon. That is, as the outer balloon is deformed, the fluid within the outer balloon acts against the outer wall of the inner balloon to deform the inner balloon and pressurize the gas, e.g., air, within the chamber of the inner balloon for pressure measurement. With the outer balloon functioning as a transmission medium, the bladder (or other body cavity in which the catheter is inserted) does not need to be filled with fluid. Thus, the catheter can be used in a voided cavity, e.g., without interstitial fluid. The radial spacing between the wall of the outer balloon and wall of the inner balloon provides space for transmission of the fluid within the outer balloon to deform the inner balloon. The spacing can be achieved in various ways which are described below and include for example, radial separation, a chamber interposed between the inner and outer balloons, a wall of the catheter interposed between the inner and outer balloons, etc. The advantages of not requiring insertion of fluid during pressure measurement are discussed below.

The pressure transducer and pressure sensor 150 can be positioned within the lumen 144 in the same manner as sensor 30 of FIG. 1 and can function in the same manner. Alternatively, the pressure transducer can be at a proximal end of the catheter 140 as in the embodiment of FIG. 12 or external of the catheter. A temperature sensor can be part of sensor 150 as in the embodiment of FIG. 1 or alternatively it can be a separate component which can be positioned for example distal of the pressure sensor within the gas, i.e., air, lumen as in the embodiment of FIG. 8A. The transmission wires of the pressure sensor 150 and the temperature sensor extend through lumen 144.

The catheter 140 can optionally include a stabilizing balloon 145 similar to balloon 76 of FIG. 8. The catheter 140 would have a lumen, e.g., lumen 146, to inflate the stabilizing balloon 145. Lumen 148 with side opening 149 provides for drainage of the bladder. Lumen 144 which is used to inflate the inner balloon 143 and create the gas column has an opening at a distal region to communicate with inner balloon 143. A separate lumen 147 has an opening at a distal region to communicate with the outer balloon 142 to fill the outer balloon 142.

In use, catheter 140 is inserted into the bladder and stabilizing balloon 145 is inflated to secure the catheter 140 in place. The system is charged by inflation of the inner balloon 143, i.e., preferably partially inflated for the reasons discussed above, by insertion of air through a side port which is in fluid communication with lumen 144 in a closed system formed by the internal space 143a of the inner balloon 143 and the internal lumen 144 communicating with the internal space of inner balloon 143. Outer balloon 142 is filled, i.e., preferably partially inflated for the reasons discussed above, via injection of air through a separate lumen. With the outer balloon 142 inflated, pressure monitoring can commence as external pressure applied to the larger circumferential outer surface of the outer balloon 142 compresses and deforms the outer balloon 142 which compresses the inner balloon 143. As the inner balloon 143 is compressed and deformed in response to compression/deformation of the outer balloon 142 based on changes to bladder pressure, the sensor 150 at the distal end of lumen 144 provides continuous pressure readings, converted to an electrical signal by the transducer within the distal end of lumen 144, and then electrically communicates through wires 152 extending through lumen 144 to an external monitor either directly or via a converter. Although, the system is capable of continuous pressure and continuous temperature monitoring, as in the other embodiments disclosed herein it can also be adapted if desired for periodic monitoring so the pressure and/or temperature readings can be taken at intervals or on demand by the clinician. Note fluid does not need to be present in the cavity to achieve the pressure readings.

Note that although separate lumens are provided for the inflation of inner balloon 143 and outer balloon 142, in an alternate embodiment, a single lumen can be utilized to inflate both balloons 143 and 142.

FIG. 16 illustrates an alternate embodiment of catheter 140, designated by reference numeral 140'. Catheter 140' is identical to catheter 140 except a larger outer balloon 142' is provided to cover more surface area for pressure readings. In all other respects, catheter 140' is identical to catheter 140 and for brevity further discussion is not provided since the features and functions of catheter 140, and its alternatives such as single or two lumens for inner and outer balloon inflation, are fully applicable to catheter 140'. For ease of understanding, the components of catheter 140' which are identical to catheter 140 are given the same reference numerals as catheter 140.

Note that the larger balloon 142' can be used with the catheters of any of the embodiments described herein. Thus, a pressure balloon of the larger size balloon 142' can be used instead of the smaller pressure balloons illustrated in the drawings. Note the size of the balloons is provided by way of example and are not necessarily drawn to scale comparatively to the other components.

Figure 17A:
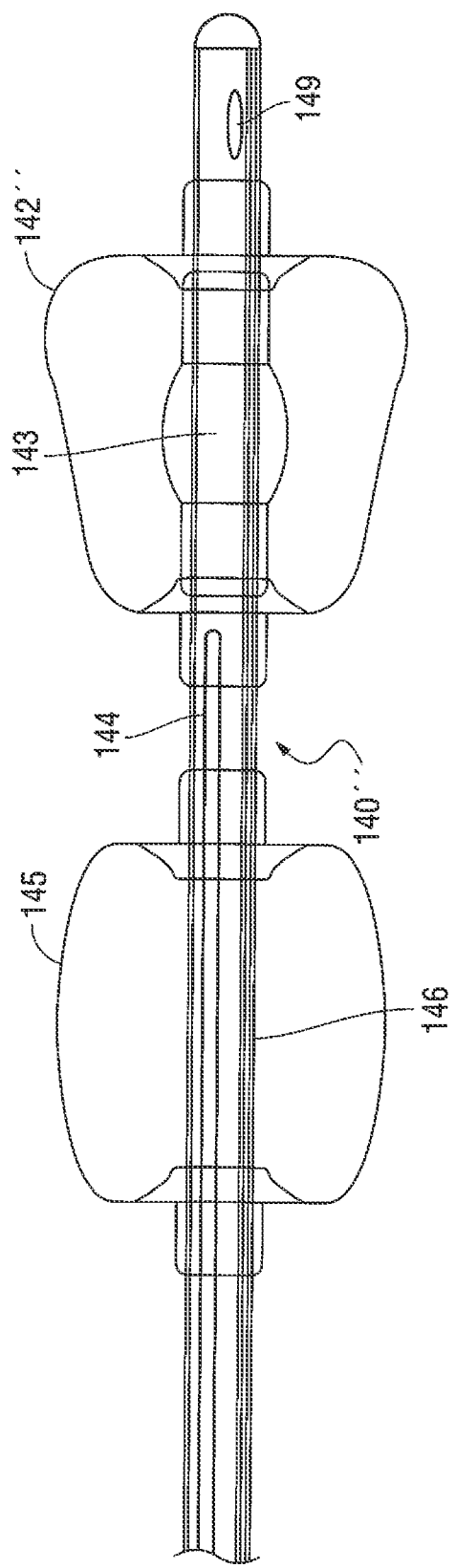
FIG. 17A is a side view similar to FIG. 15 illustrating an alternate embodiment having a pear-shaped outer balloon.
Figure 17B:
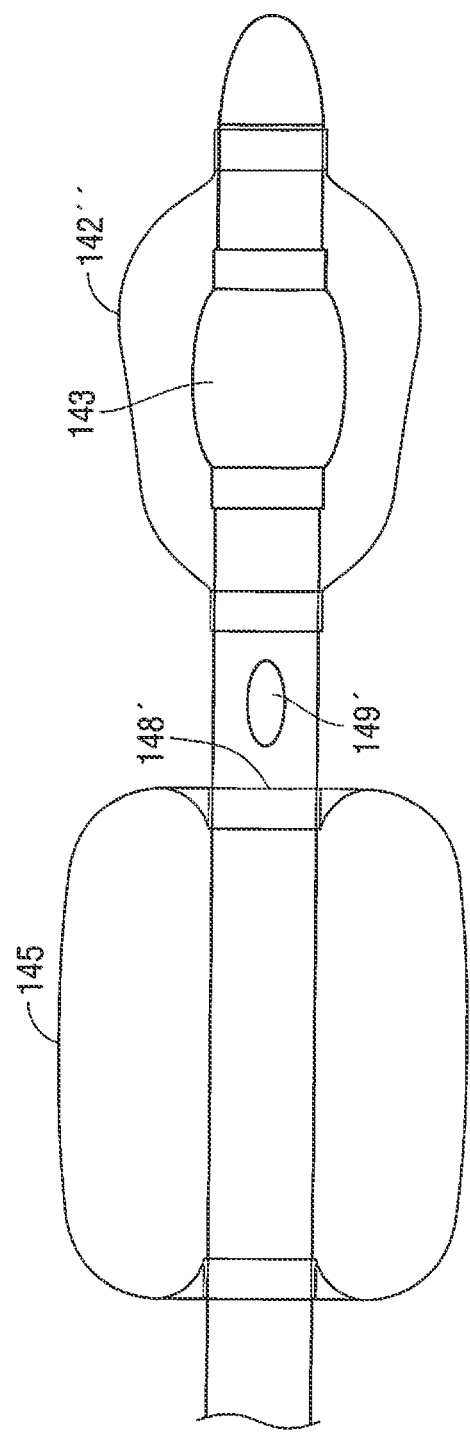
FIG. 17B is a side view similar to FIG. 17A showing an alternate embodiment wherein the drainage opening is between the two balloons.
Figure 19:
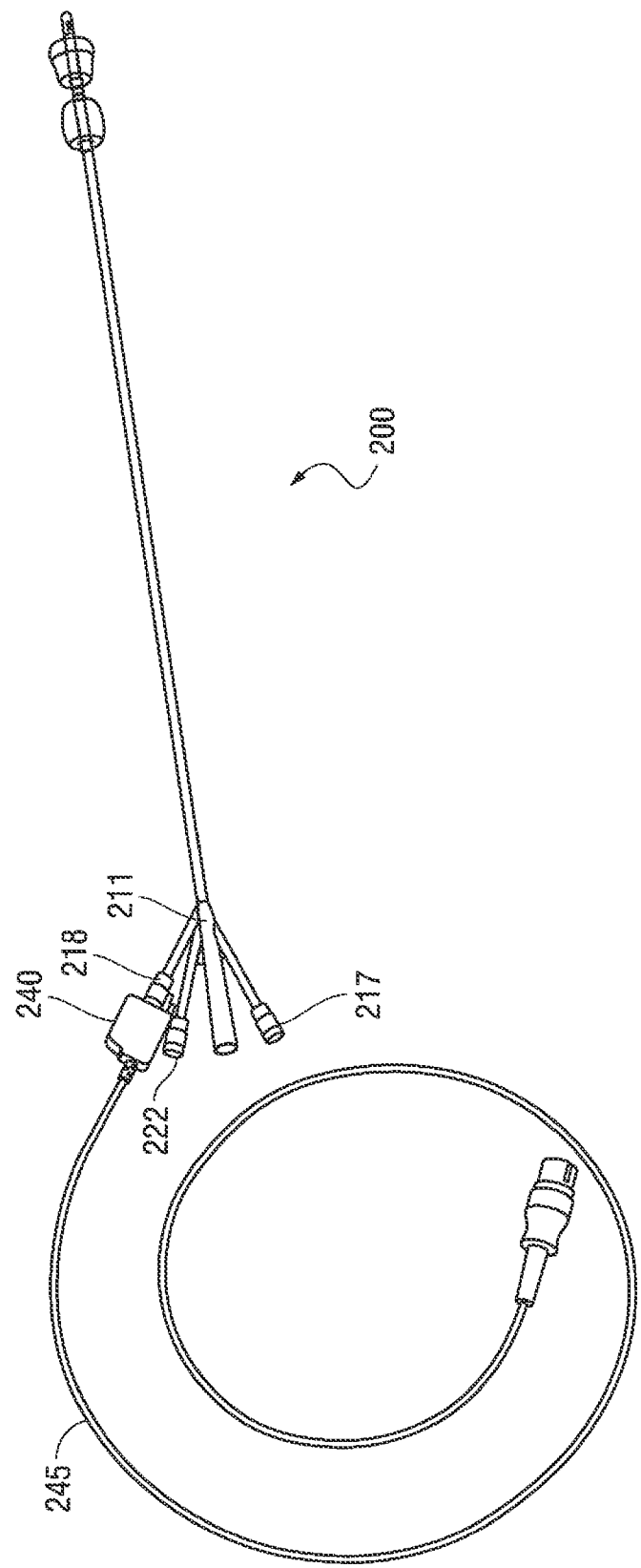
FIG. 19 is a perspective view of the catheter of FIG. 18A with a pressure transducer hub attached to the catheter.

FIG. 17A illustrates an alternate embodiment of catheter 140, designated by reference numeral 140". Catheter 140" is identical to catheter 140 except a pear shaped larger outer balloon 142" is provided. The larger balloon 142" covers more surface area for pressure readings. The pear shape could in certain applications decrease the risk of obstructing the ureter and provide more tactile continuity of the balloon to the bladder wall giving a better transmission of abdominal pressure to the internal sensor. In all other respects, catheter 140" is identical to catheter 140 and for brevity further discussion is not provided since the features and functions of catheter 140, and its alternatives such as single or two lumens for inner and outer balloon inflation, are fully applicable to catheter 140". For ease of understanding, the components of catheter 140" which are identical to catheter 140 are given the same reference numerals as catheter 140. FIG. 17B illustrates a catheter identical to catheter 140" with identical balloons, the only difference being that the side opening 149' is positioned proximal of the balloon 143 rather than distal of the balloon as in FIG. 17A. That is, opening 149', in communication with the catheter lumen 148' for drainage of the bladder, is positioned between the stabilizing balloon 145 and the inner and outer pressure (and inner) pressure balloon 142" (and 143). Thus, it is distal of the stabilizing balloon 145 and proximal of the outer balloon 142".

Note that the positioning of the side opening for drainage of FIG. 17B, which communicates with the drainage lumen of the catheter, can be utilized with any of the catheters disclosed herein. Thus, in the catheters disclosed in the various embodiments herein, instead of the drainage opening positioned distal of the pressure balloon(s), it can be proximal of the pressure balloon and distal of the stabilizing balloon so it is between the two balloons.

Note that the pear shaped balloon 142" can be used with the catheters of any of the embodiments described herein. Thus, a pressure balloon of the pear shape of balloon 142", and of larger size if desirable, can be used instead of the pressure balloons illustrated in the drawings.

FIGS. 18-25B illustrate an alternate embodiment of the catheter of the present invention. The pressure balloon for detecting pressure, designated by reference numeral 202, forms an outer balloon of catheter 200. Contained within the outer balloon 202 is an inner balloon 204. The inner balloon 204 provides a smaller diameter balloon and a smaller circumference (and volume) than the outer balloon 202. The inner balloon 204 together with the lumen 214, which communicates with the inner balloon 204 for inflation thereof, forms a smaller gas, e.g., air, column as in the embodiments of FIGS. 15-17. This provides finer measurements. Thus, the compliant outer balloon 202 fluid or wall compresses the outer wall 205 of the compliant inner balloon 204 which compresses the air (or other gas) within air lumen 214. The closed system is thereby formed by the internal space 204a of the inner balloon 204 and the lumen 214. The smaller balloon air column can in certain instances provide a more accurate reading from the average pressure determined by the larger outer balloon 202.

The pressure transducer and pressure sensor are external to catheter 200 and mounted to port 218 at the proximal end 201 of catheter 200. More specifically, a transducer hub or housing, designated generally by reference numeral 240, contains the pressure transducer and sensor and is mounted to the angled side port 218. In the embodiment of FIG. 18A, the hub 240 is mounted over the port 218 and can be locked or secured thereto such as by a friction fit, snap fit, threaded attachment, a latch, etc., maintaining an airtight seal so the air is contained within the lumen 214 and balloon 204. The hub 240 has an elongated (rod-like) member or nose 242 extending distally therefrom (FIG. 24A) dimensioned to be inserted through the proximal opening in port 218 and into air lumen 214. (Note the air lumen 214 as in the other lumens extend into their respective angled side ports). The elongated member 242 also has a channel 244 extending therethrough to allow the pressure wave to travel through to the pressure sensor. Although in preferred embodiments no additional air needs to be injected into inner balloon 204 via lumen 214 after attachment of hub 240, it is also contemplated that a port or opening can be provided in hub 240 to receive an injection device for injection of additional air. Such additional air can communicate with and flow through channel 244 of elongated member 242, into lumen 214 and into inner balloon 204 for inflation, or alternatively, a side port or opening in angled port downstream of the elongated member 242 could be provided.

To charge the system, when the hub 240 is mounted to the side port 218, the elongated member 242 extends into lumen 214 to advance air through the air lumen 214 into inner balloon 204 to expand inner balloon 204. In some embodiments, 0.2 cc of air can be displaced/advanced by the member 242, although other volumes are also contemplated. Thus, as can be appreciated, mounting of the hub 240 to the catheter 200 automatically pressurizes the air lumen/chamber and expands the inner balloon 204. Note the inner balloon 204 can be partially or fully inflated (expanded), dependent on the amount of air advanced into the inner balloon 204. Further note that the lumen 214 is not vented to atmosphere when the transducer hub 240 is attached and air is advanced through the air lumen. The port 218 can include a closable seal through which the elongated member 242 is inserted but maintains the seal when the elongated member 242 remains in the lumen 214.

Lumen 214 which is used to inflate the inner balloon 204 and create the air column has an opening at a distal region to communicate with the interior of inner balloon 204. Lumen 212 of catheter has an opening at a distal region to communicate with the outer balloon 202 to fill the outer balloon 202. Angled port (extension) 222 at the proximal end of catheter 200 receives an inflation device to inflate, either fully or partially, the outer balloon 202.

Note as in the other embodiments disclosed herein, air is described as the preferred gas for creating the column and expanding the balloon, however, other gasses are also contemplated, for each of the embodiments disclosed herein.

Figure 20A:
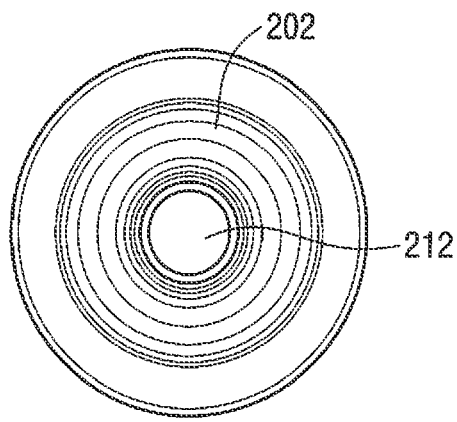
FIGS. 20A, 20B and 20C are enlarged front, side and perspective views of the outer balloon of FIG. 18A in the expanded condition.
Figure 20B:
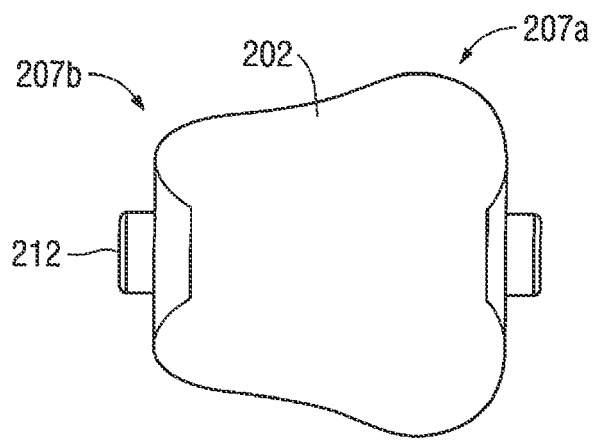
Figure 20C:
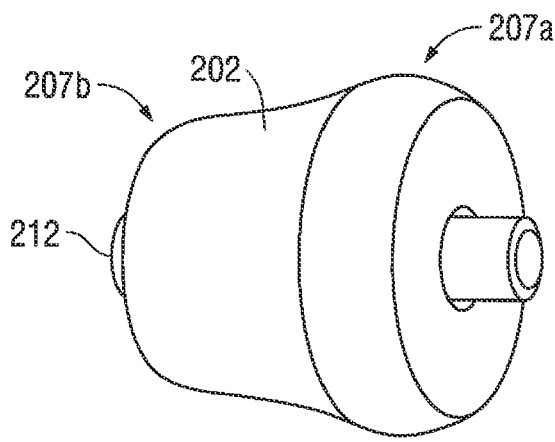
Figure 21A:
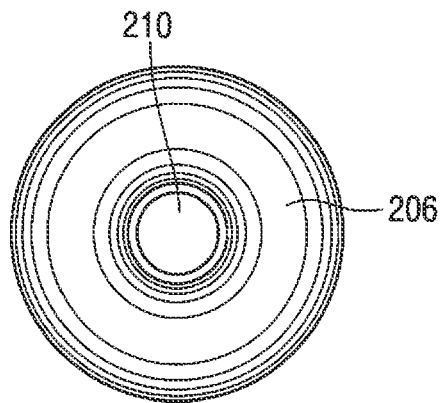
FIGS. 21A, 21B and 21C are enlarged front, side and perspective views of the stabilizing balloon of FIG. 18A in the expanded condition.
Figure 21B:
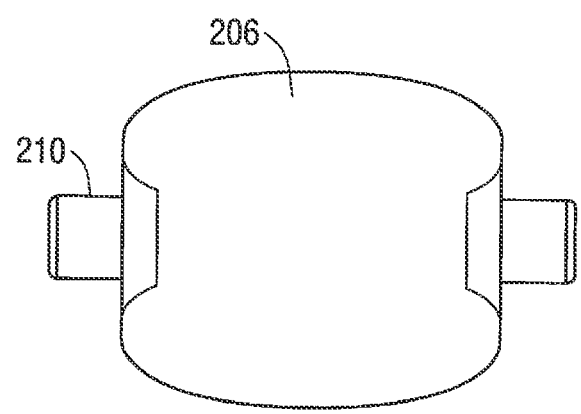
Figure 21C:
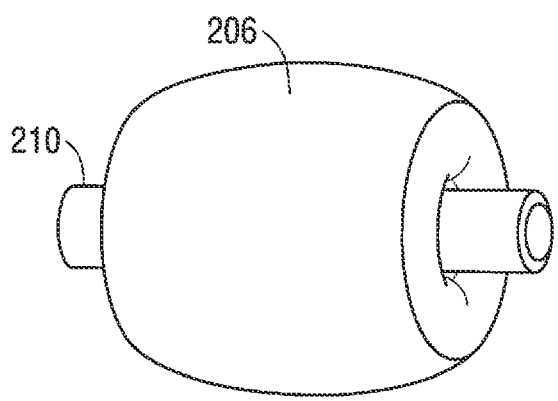
Figure 22A:
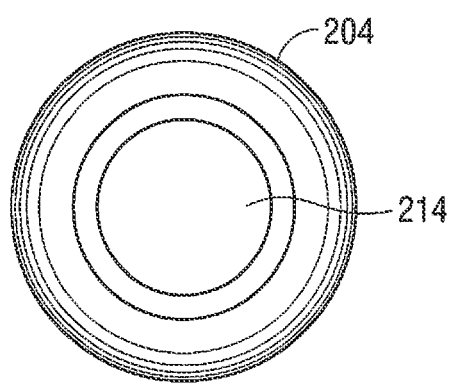
FIGS. 22A, 22B and 22C are enlarged front, side and perspective views of the inner balloon of FIG. 18A in the expanded condition.
Figure 22B:
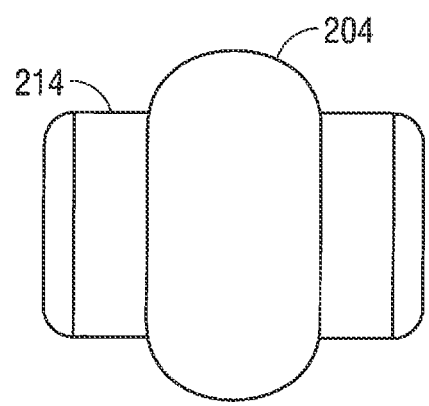
Figure 22C:
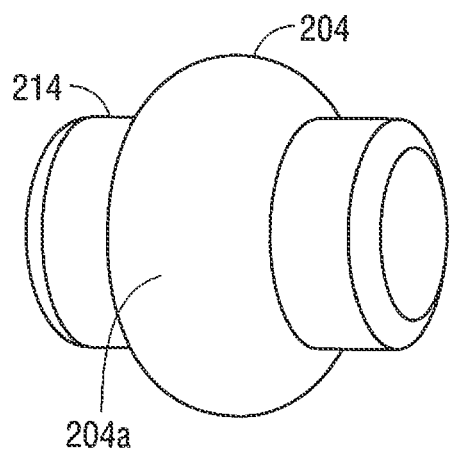

The outer balloon 202 can be shaped such that a distal region 207a (FIGS. 20A-20C) has an outer transverse cross-sectional dimension, e.g., diameter, greater than an outer transverse cross-sectional dimension, e.g., diameter, of the proximal region 207b. A smooth transition (taper) can be provided between the distal region 207a and proximal region 207b. Note the balloon 202 can be pear shaped as shown in FIGS. 20B and 20C although other configurations are also contemplated. This pear shape in some applications is designed to conform to the shape of the bladder.

The inner and outer balloons 204, 202 can by way of example be made of urethane, although other materials are also contemplated such as silicone or EVA.

Figure 25A:
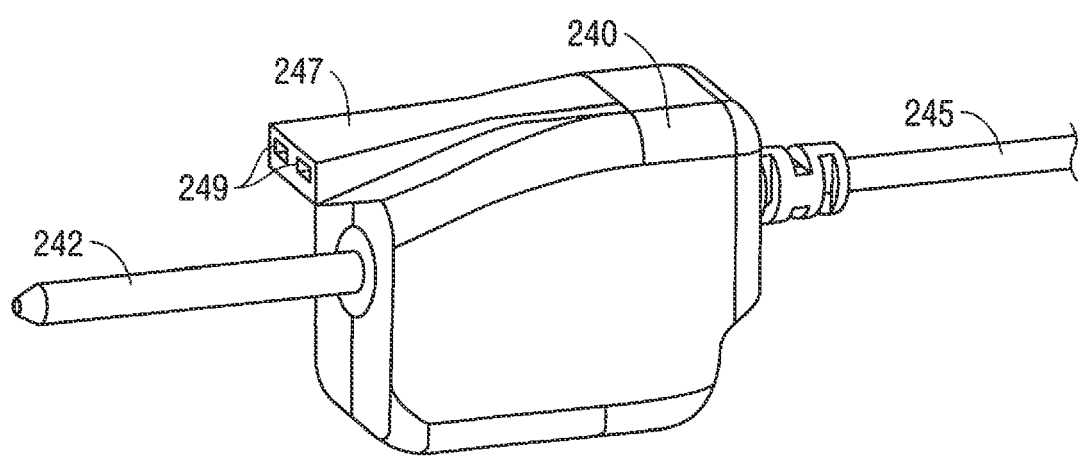
FIG. 25A is a perspective view of the transducer hub of FIG. 24A.
Figure 25B:
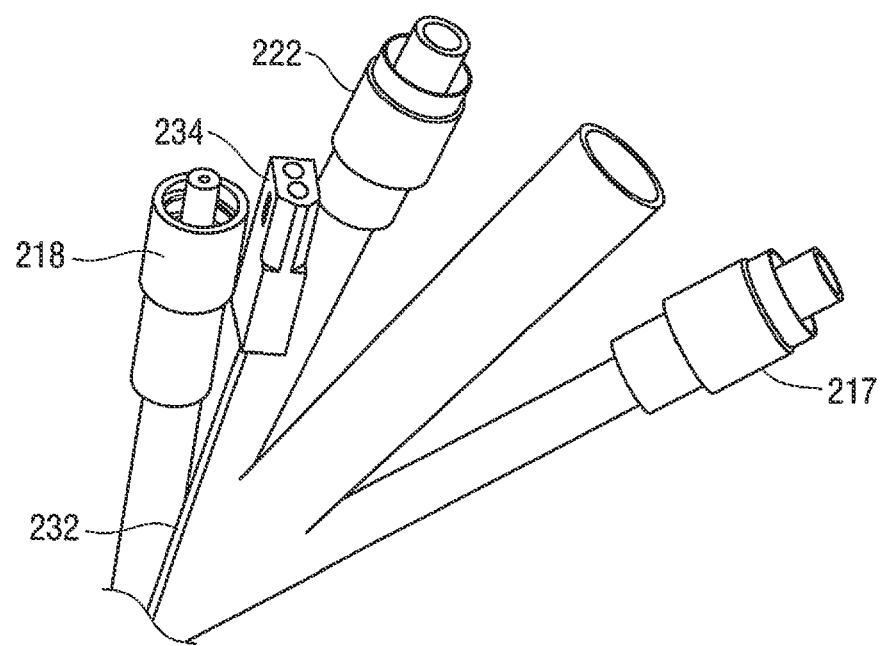
FIG. 25B is a perspective view of the proximal end of the catheter showing a connector for the thermocouple wire.

A temperature sensor 230 (FIG. 18B), such as a thermocouple, is positioned within the catheter 200 at a distal end to measure core body temperature. The sensor 230 is shown positioned in a lumen 216 separate from the lumens 214 and 212. One or more wires 232 extend from the sensor 230 through the lumen 216, exiting the lumen 216 and catheter 200 at a proximal end between the angled extensions/ports of the catheter 200, e.g., between the port 218 for the inner balloon 204 and the port 222 for the outer balloon 202. A connector 234, e.g., a male connector, is at the proximal terminal end of the wire 232 as shown in FIG. 25B. The transducer hub 240 includes a connector 247 with openings 249 (FIG. 25A) which receive the connector 234 of the wire 232. When the hub 240 is mounted to port 218 of catheter 200, the connector 234 of the wire is automatically connected to a connector carried by or within the hub 240 which is in communication with a temperature monitor. Note the connector, e.g., female connector, within or carried by the hub 240 can already be mounted to an external temperature monitor via a cable when the hub 240 is mounted to catheter 218 or alternatively the hub 240 can first be mounted to port 218 of the catheter 200 and then a cable is connected between the temperature monitor and catheter 200. In the illustrated embodiment of FIG. 25A, the wire connector 234 can plug into the openings 249 of connector 247 positioned on the hub 240. Note the connector 247 can also be internal of the hub 240 with an opening in the wall of the hub to enable access for the wire connector. Also note that alternatively the wire can include a female connector and the hub can have a male connector. Other types of connectors/connections are also contemplated.

As can be appreciated, connection of the transducer hub 240 to the catheter 200 (port 218) a) automatically connects the temperature sensor 230 to a connector for communication with a temperature monitor cable; and b) automatically advances air through the first lumen 214 to expand the inner balloon 204.

The catheter 200 can optionally include a stabilizing balloon 206 similar to balloon 76 of FIG. 8A. The stabilizing balloon 206 can be made of silicone, although other materials are also contemplated. If provided, the catheter 200 would have a lumen, e.g., lumen 210, to inflate the stabilizing balloon 206. Angled side port 217 can be provided in communication with lumen 210 for injection of a liquid or gas to expand the stabilizing balloon 206. The foregoing description of the stabilizing balloons in connection with other embodiments is fully applicable to balloon 206. Catheter 200 also includes a lumen 211 with a distal side opening 211a (FIG. 18B) to provide for drainage of the bladder as in the aforedescribed embodiments. In the illustrated embodiment, the side opening 211a is distal of outer balloon 202 and inner balloon 204 and distal of the stabilizing balloon 210 which as shown is proximal of outer balloon 202 and inner balloon 204. In alternate embodiments, the stabilizing balloon 206 can be distal of the outer balloon 202.

Figure 23:
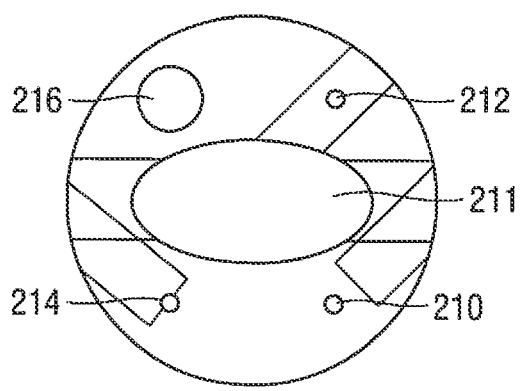
FIG. 23 is a transverse cross-sectional view of the catheter of FIG. 18 illustrating the five lumens of the catheter.
Figure 24A:
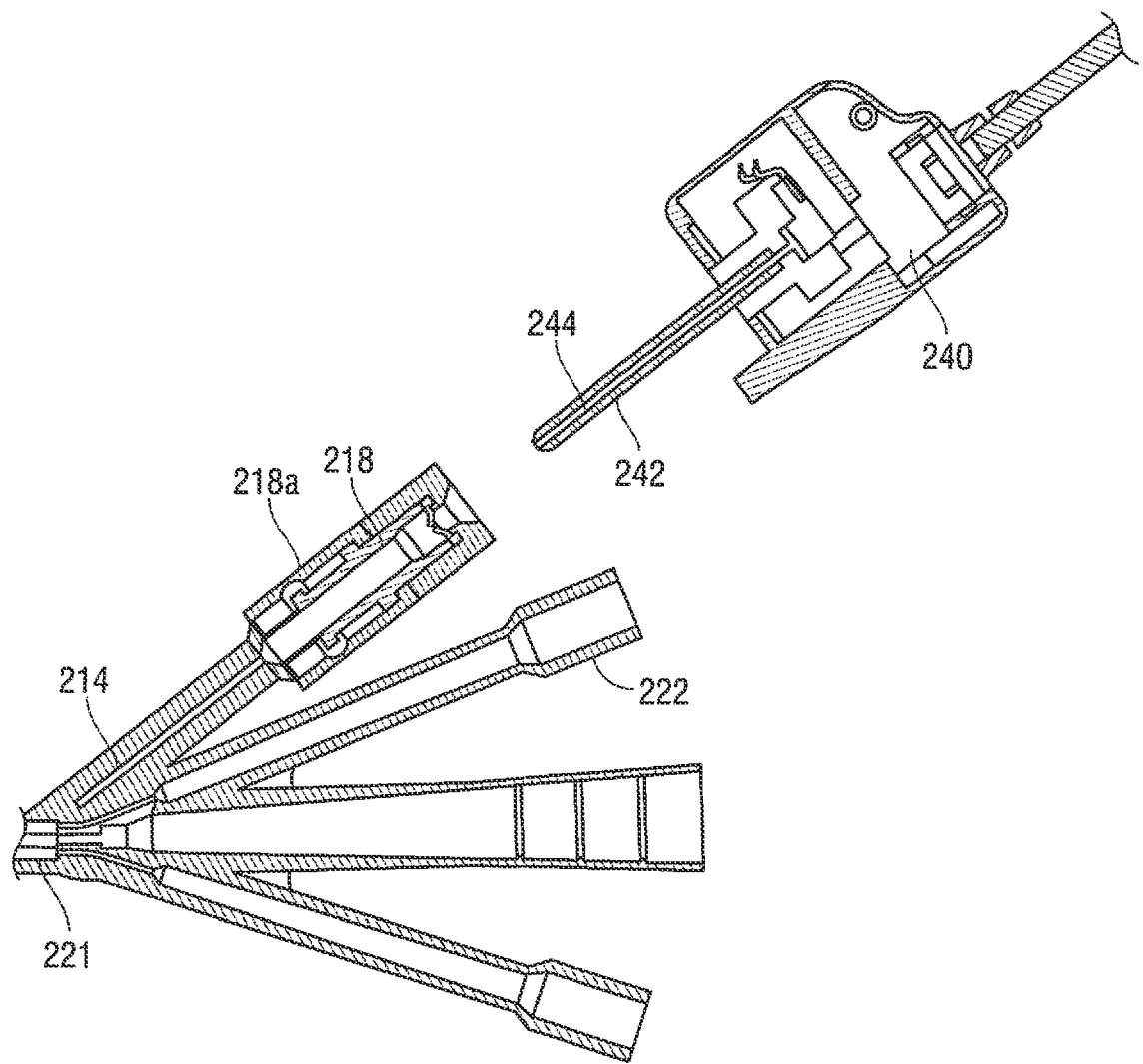
FIG. 24A is a cutaway side view showing the pressure transducer hub prior to connection to the catheter of FIG. 18A, a portion of the hub wall and catheter connector removed to show internal components.
Figure 24B:
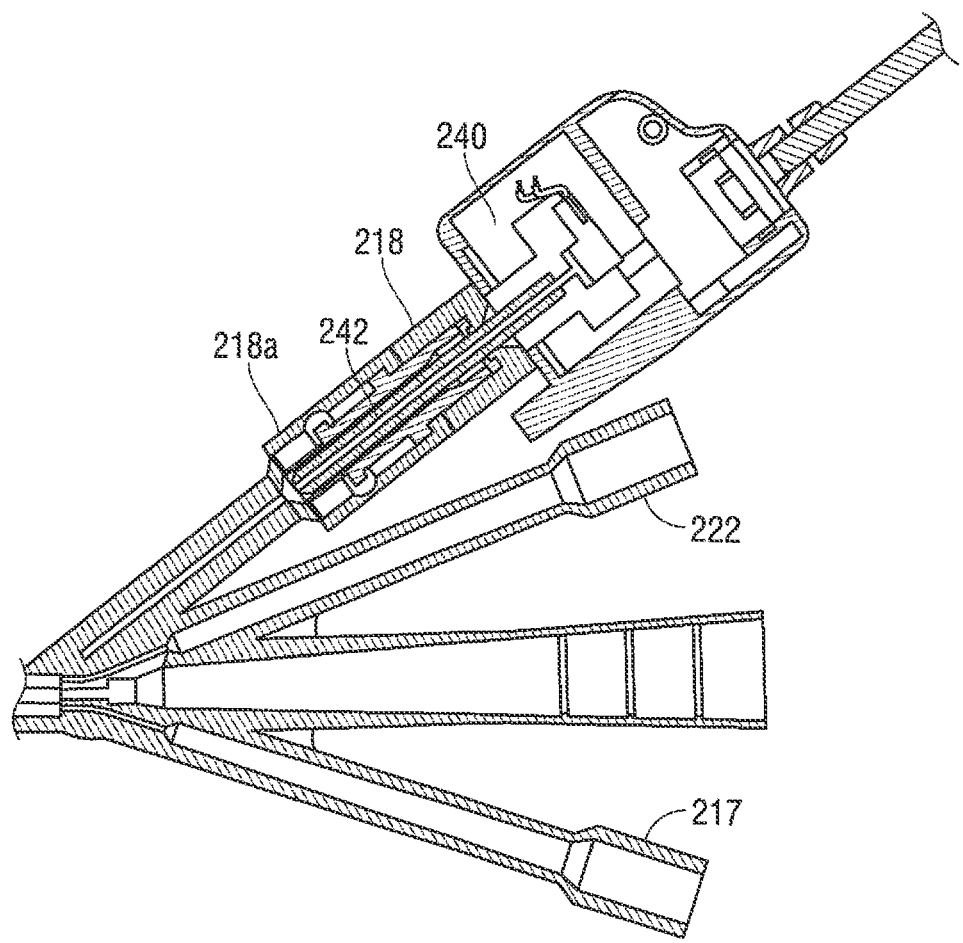
FIG. 24B is a side view similar to FIG. 24A showing the hub attached to the catheter.

Thus, in the embodiment of FIG. 18A, catheter 200 has five lumens: 1) lumen 214 communicating with inner balloon 204 to inflate the inner balloon 204 and forming the air filled chamber; 2) lumen 212 communicating with outer balloon 202 for inflating outer balloon 202; 3) lumen 210 communicating with the stabilizing balloon 206 to inflate stabilizing balloon 206; 4) drainage lumen 211 having a side opening 211a at a distal end for drainage of the bladder; and 5) lumen 216 for the temperature sensor wire(s) 232. Catheter 200 also has three angled extensions/ports at its proximal end 201: 1) port 218 for access to lumen 214 to inflate the inner balloon 204; 2) port 222 for access to lumen 212 to inflate outer balloon 202; and 3) port 217 for access to lumen 210 to inflate stabilizing balloon 206. Drainage lumen 211 extends linearly terminating at region 223. Lumen 216 terminates proximally at the region of the angled ports 218, 222 through which wire 232 can exit from the catheter 200 for connection to a temperature monitor via hub 240. Note the location of the ports can vary from that illustrated in FIG. 18. Also, location of the lumens and the cross-sectional dimension and size of the lumen can vary from that shown in FIG. 23 as FIG. 23 provides just one example of the location and size, e.g., diameter, of the lumens as well as the shape/cross-sectional configuration and location. The catheter 200, as in the foregoing embodiments, can have an atraumatic tip 209.

In use, catheter 200 is inserted into the bladder and stabilizing balloon 206 is inflated to secure the catheter 200 in place. The system is charged by inflation of the inner balloon 204, i.e., preferably partially inflated for the reasons discussed above, by advancement of air through lumen 214 upon attachment of the pressure transducer 240 to the port 218 of catheter 200. Such attachment moves elongated member 242 into lumen 214 to displace the air (or other gas) already in the lumen 214 to expand the inner balloon 204. A closed system is formed by the internal space 204a of the inner balloon 204 and the internal lumen 214 communicating with the internal space 204a of inner balloon 204. In a preferred embodiment, additional air does not need to be added to the balloon 204/lumen 214. Outer balloon 202 is filled, i.e., preferably partially inflated for the reasons discussed above, via injection of air through the separate port 222 which communicates with lumen 212 of catheter 200. With the outer balloon 202 inflated, pressure monitoring can commence as external pressure applied to the larger circumferential outer surface of the outer balloon 202 compresses and deforms the outer balloon 202 which exerts a force on the outer wall of inner balloon 204 and compresses the inner balloon 204. As the inner balloon 204 is compressed and deformed in response to compression/deformation of the outer balloon 202 based on changes to bladder pressure, the pressure sensor within the external hub 240 attached at the proximal end of the catheter 200 provides continuous pressure readings, converted to an electrical signal by the transducer within the hub 240, and then electrically communicates through a connector, e.g. cable 245, to an external monitor either directly or via a converter to display pressure readings. Although, the system is capable of continuous pressure and continuous temperature monitoring, it can also be adapted if desired for periodic monitoring so the pressure and/or temperature readings can be taken at intervals or on demand by the clinician. Temperature readings are also taken during the procedure as temperature sensor 230 is connected to a temperature monitor via wire 232 connected to a connector of hub 240 which is connected to the temperature monitor to display temperatures. The temperature monitor can be separate from the pressure display monitor or alternatively integrated into one monitor. Cable 245 can connect to the temperature monitor as well (directly or via a converter) or a separate cable extending from the hub 240 could be provided for connection to the temperature monitor.

Note that although separate lumens are provided for the inflation of inner balloon 202 and outer balloon 204, in an alternate embodiment, a single lumen can be utilized to inflate both balloons 202 and 204. In such embodiment, catheter 200 can have one less angled port and one less lumen since inflation of the outer balloon 202 would be through port 218 and lumen 214.

The proximal and distal end of the inner balloon 204 in the illustrated embodiment are within the confines of the outer balloon 202, i.e., the proximal end of the inner balloon 204 is distal of the proximal end of the outer balloon 202 and the distal end of the inner balloon 204 is proximal of the distal end of the outer balloon 202. Thus, in this illustrated embodiment, the inner balloon 204 is fully encapsulated within the outer balloon 202.

With the inner/outer balloon arrangement, the larger outer surface of the outer balloon 202 takes gross measurements and then the forces are concentrated on the smaller inner balloon 204 to amplify/concentrate pressure on the small area of the inner balloon so small changes can be detected and waves transmitted to the pressure transducer (via the length of the lumen to a proximal transducer, e.g. an external pressure transducer).

As noted above, preferably no additional air needs to be added after mounting of hub 240. However, it is also contemplated that in alternate embodiments a port can be provided in communication with hub 240 to enable subsequent injection of air though lumen 214 and into inner balloon 204. Additionally, outer balloon 202 can in some embodiments receive additional fluid injection via port 222 during the procedure.

FIGS. 30A-34 illustrate an alternate embodiment of the catheter, designated generally by reference numeral 400. The catheter 400 differs from catheter 200 of FIG. 18A in the attachment of the inner and outer balloons to the catheter shaft. The catheter 400 also differs catheter 200 described above in the location of the drainage hole(s). In all other respects catheter 400 is the same as catheter 200 and thus the features and functions of catheter 200, and its alternatives disclosed herein, are fully applicable to catheter 400.

Catheter 400 has a shaft 402 having a distal region (portion) 402a terminating in a distal opening 402b. Distal opening 402b receives core pin 410 therein. Core pin 410, also referred to as a bonding pin or a connecting pin, has a proximal end 414a dimensioned for insertion in a press fit through opening 402b and into the lumen in distal region 402a of shaft 402. In the illustrated embodiment, the proximal end 414a has a non-circular shape, e.g., a triple lobe or Y shape, corresponding to the shape of the opening 402b. The distal end of the pin 410 has a reduced diameter cylindrical portion 414b which receives thereover a distal tip 412 (also referred to herein as a distal plug).

Catheter 400 further has a retention (stabilizing) balloon 404, an inner balloon 406 and an outer balloon 406. The retention balloon 404 is spaced proximally of the outer balloon 406 and inner balloon 408. The outer balloon 406 encapsulates the inner balloon 408 such that the inner wall 408c of the inner balloon 408 is contained within the outer balloon 406. The outer wall 408c of outer balloon 408 is exposed to the patient, e.g., the bladder. The retention balloon 404 functions in the same way as the retention (stabilizing) balloons described above and can of varying shapes as described herein. The inner and outer balloons 408, 406 function in the same way as the inner and outer balloons 204, 202 of catheter 200.

Figure 30A:
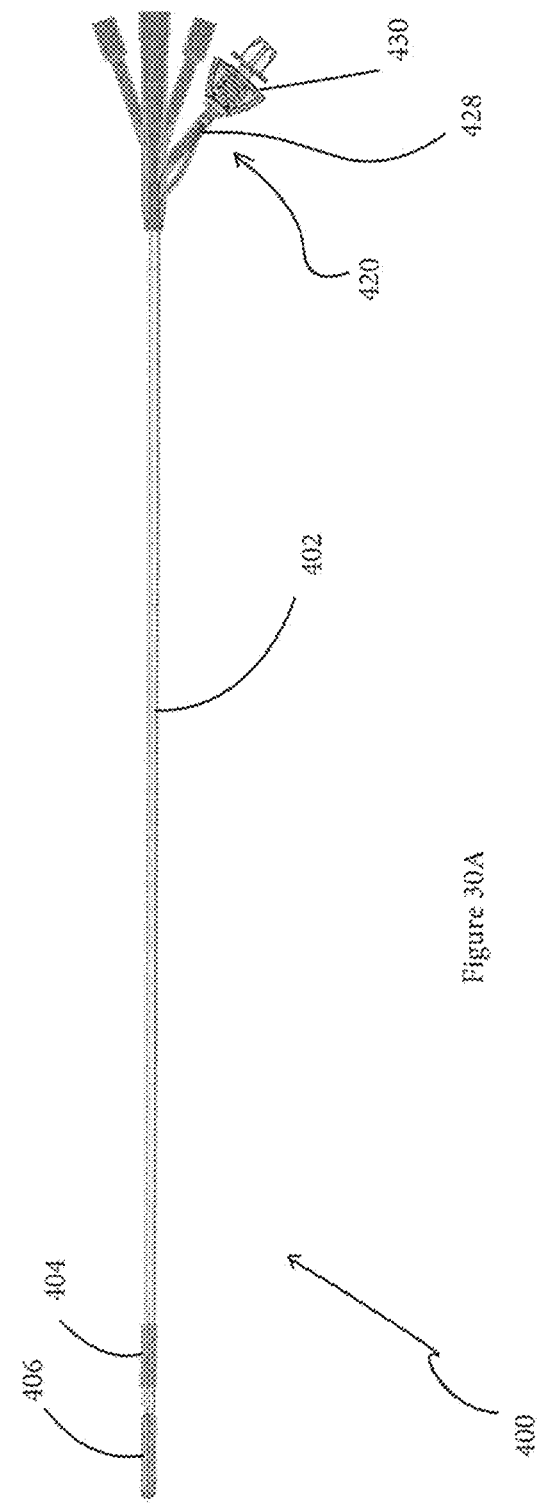
FIG. 30A is a side view of an alternate embodiment of the catheter of the present invention.
Figure 30C:
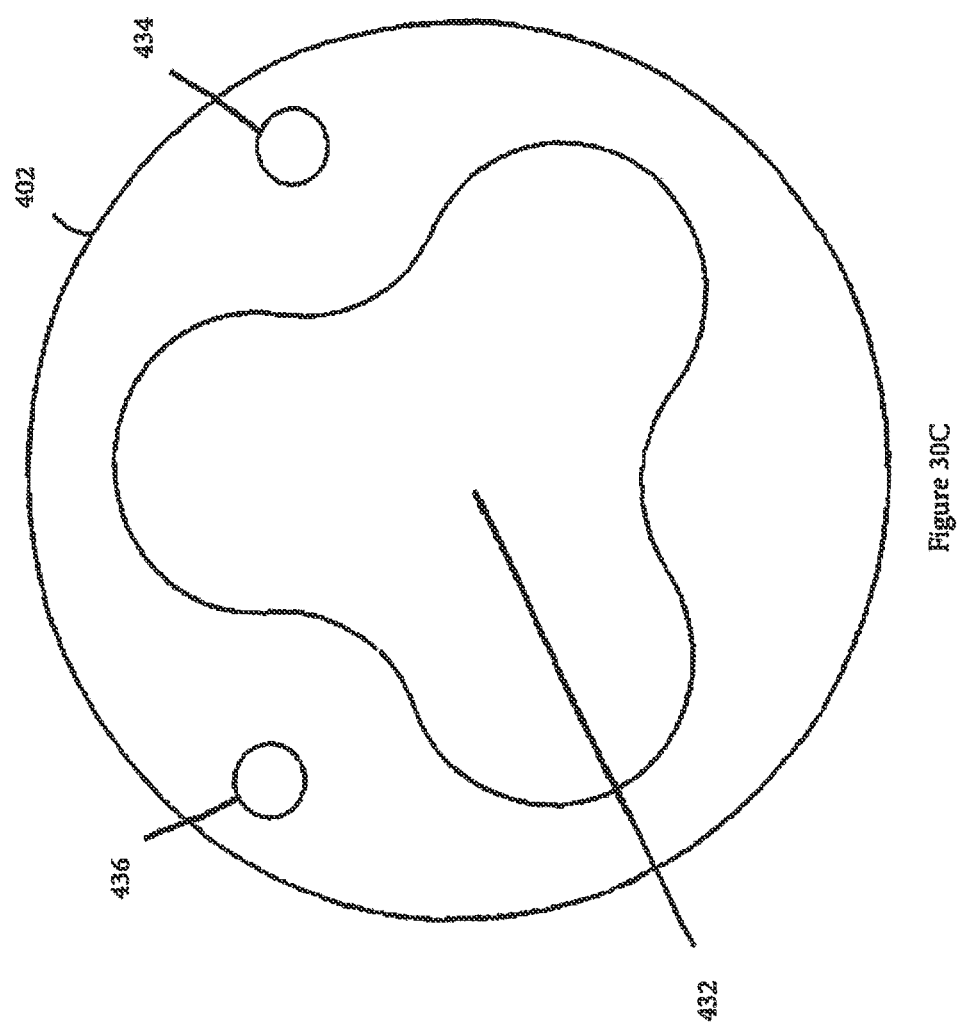
FIG. 30C is an enlarged transverse cross-sectional view of the catheter of FIG. 30A.
Figure 31:
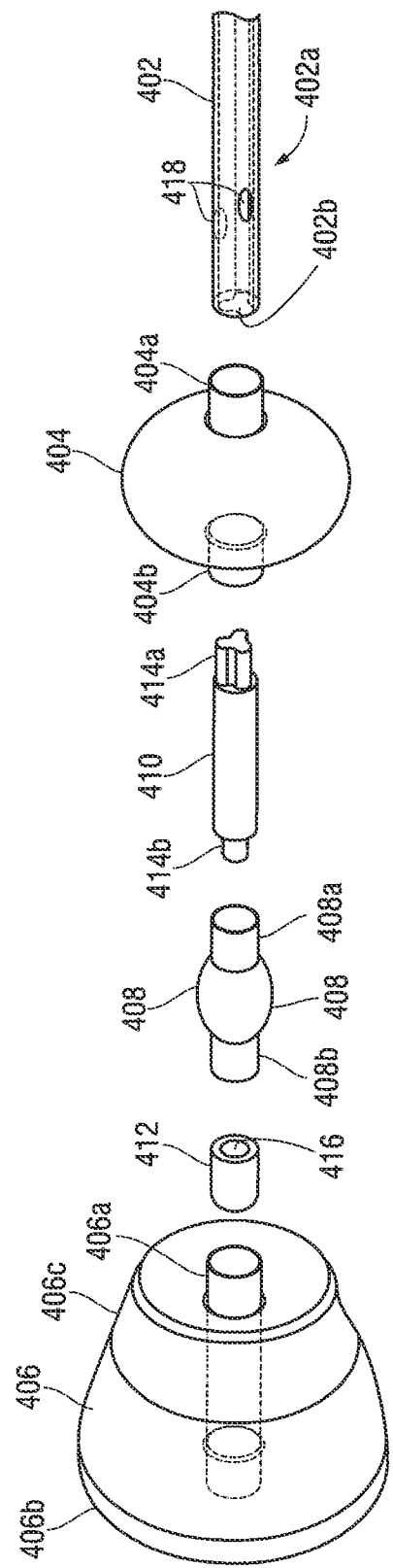
FIG. 31 is a close up exploded view of the distal end of the catheter of FIG. 30A.

As shown in the cross-sectional view of FIG. 30C, the catheter shaft 402 has four lumens: 1) lumen 438 communicating with inner balloon 408 to inflate the inner balloon 408 and forming the gas, e.g., air, filled chamber; 2) lumen 434 communicating with outer balloon 406 for inflating outer balloon 406; 3) lumen 436 communicating with the retention balloon 404 to inflate retention balloon 404; and 4) drainage lumen 432 having one or more side openings 418 (FIG. 32C) at a distal region of the catheter for drainage of the bladder. The lumens 438, 434 and 436 terminate inside of their respective balloons 402, 406 and 404. The side opening(s) 418 for drainage are positioned between the outer/inner balloon 406, 408 and the retention balloon 404 such that the outer balloon 406 and inner balloon 408 are distal of the side opening(s) 418 and the retention balloon 404 is proximal of the side opening(s) 418. Temperature sensor wires can be positioned in lumen 438, running parallel to the tubular portion (described below) of the inner balloon in embodiments where the balloon has the tubular portion, e.g., balloon 458, with the thermistor sensor located near the drainage holes 418. Alternatively, the temperature sensor wires can be positioned in the same lumen as the lumen for filling the outer balloon or the inner balloon or an additional lumen can be provided for the temperature sensor wire(s).

Catheter 400 also has three angled extensions/ports at its proximal end 420 (FIG. 30B): 1) port 428 for access to lumen 438 to inflate the inner balloon 408; 2) port 426 for access to lumen 434 to inflate outer balloon 406; and 3) port 422 for access to lumen 436 to inflate stabilizing balloon 404. Drainage lumen 432 extends linearly terminating at a distal region proximal of core pin 410 and terminating proximally at port 424. Note the location of the ports can vary from that illustrated in FIG. 30B. Also, the location of the lumens and the cross-sectional dimension and size of the lumens can vary from that shown in FIG. 30C as FIG. 30C provides just one example of the location and size, e.g., diameter, of the lumens as well as the shape/cross-sectional configuration and location.

Figure 32A:
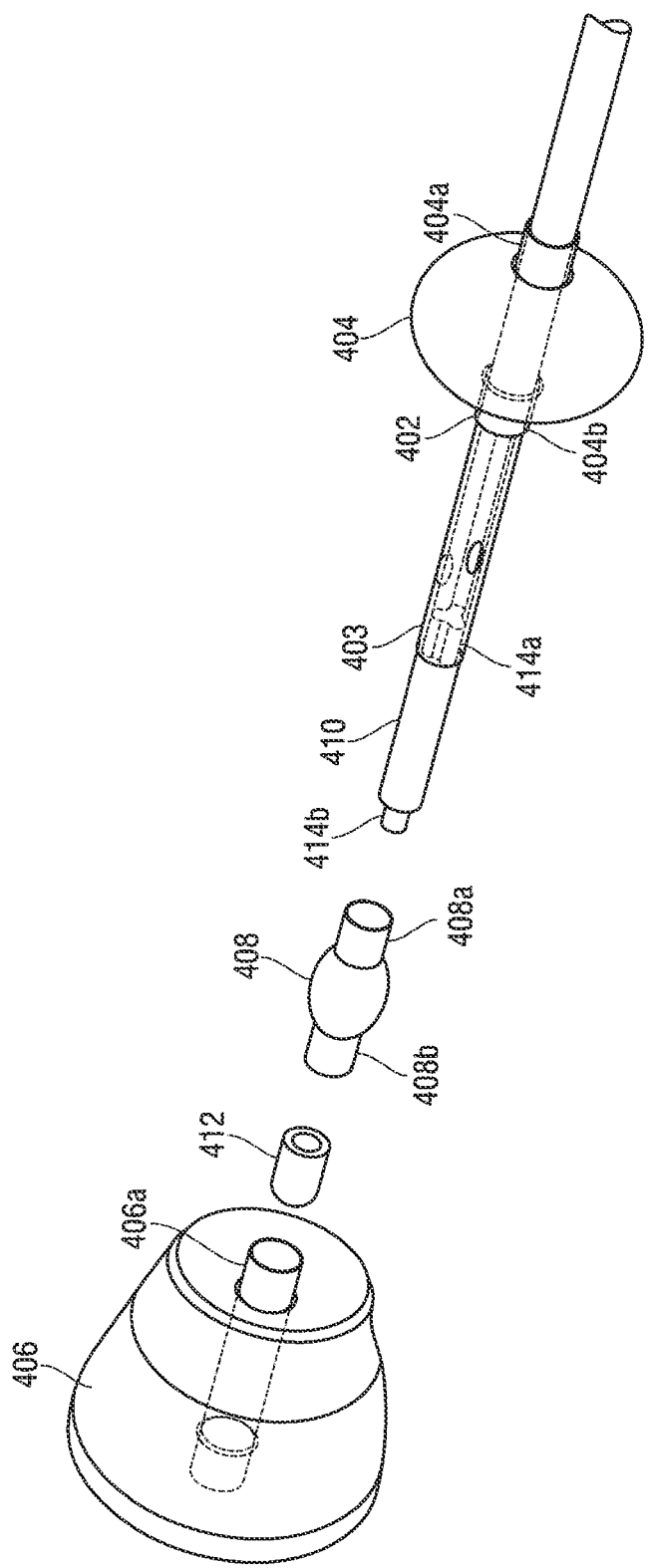

The steps of manufacture (assembly) of the balloons to the catheter will now be described with reference to FIGS. 32A-32C. The assembly steps are shown with the balloons inflated for ease of illustration but the assembly would preferably be made with the balloons deflated. In manufacture, the stabilizing balloon 404, which is identical in function and can be the same shape as the stabilizing (retention) balloons discussed above, such as a donut shape as shown, is placed over the outer shaft 402 and proximal and distal extensions 404a, 404b of balloon 404 are attached, e.g., welded to the shaft 402. In the illustrated embodiment, the stabilizing balloon 404 is composed of the same material as the distal region 402a of shaft 402. In one embodiment by way of example, the material is silicone, although other materials are also contemplated. After the stabilizing balloon 404 is placed over the shaft 402, positioned proximal of the distal end of the shaft 402, and preferably after it is also attached to the shaft 402, the bonding pin 410 is inserted into the shaft 402. More specifically, proximal extension 414a extends into distal opening 402b of shaft 402, with a portion of the pin 410 including the distal extension 414b extending distally from and exposed from the shaft 402 as shown in FIG. 32A. The bonding pin 410 is preferably mechanically fixed, such as by a press fit into the lumen of the shaft 402. The shaft 402 contains small holes overlying the inserted pin 410 and the small holes are filled with material, e.g., silicone, to secure the pin 410 to the shaft 402.

Figure 32B:
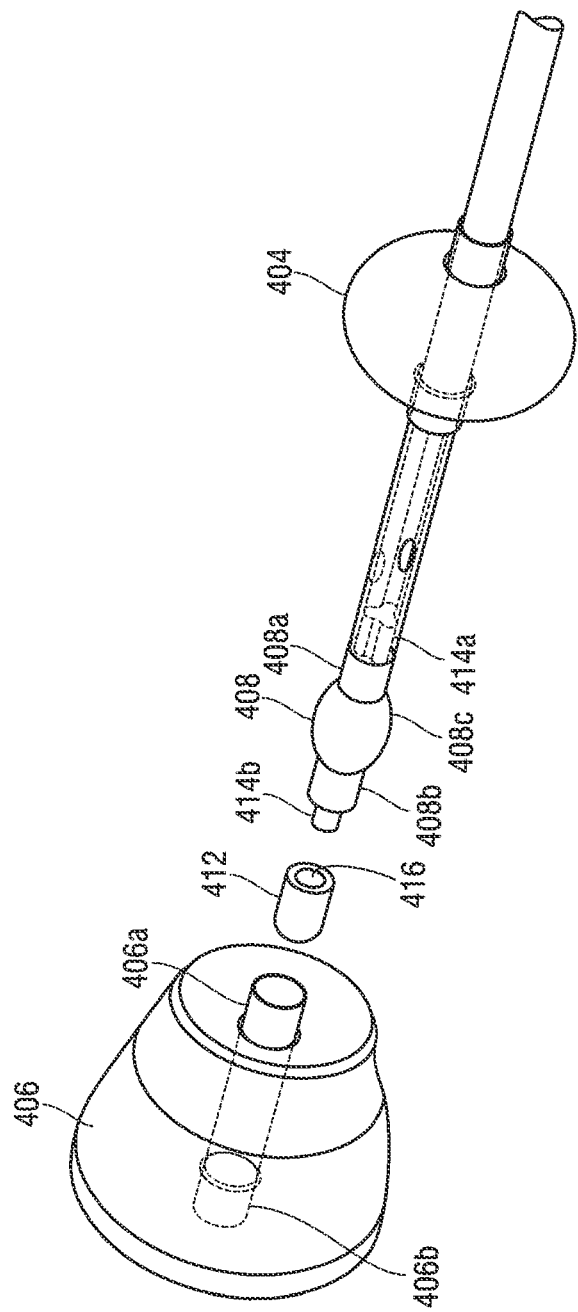
Figure 32C:
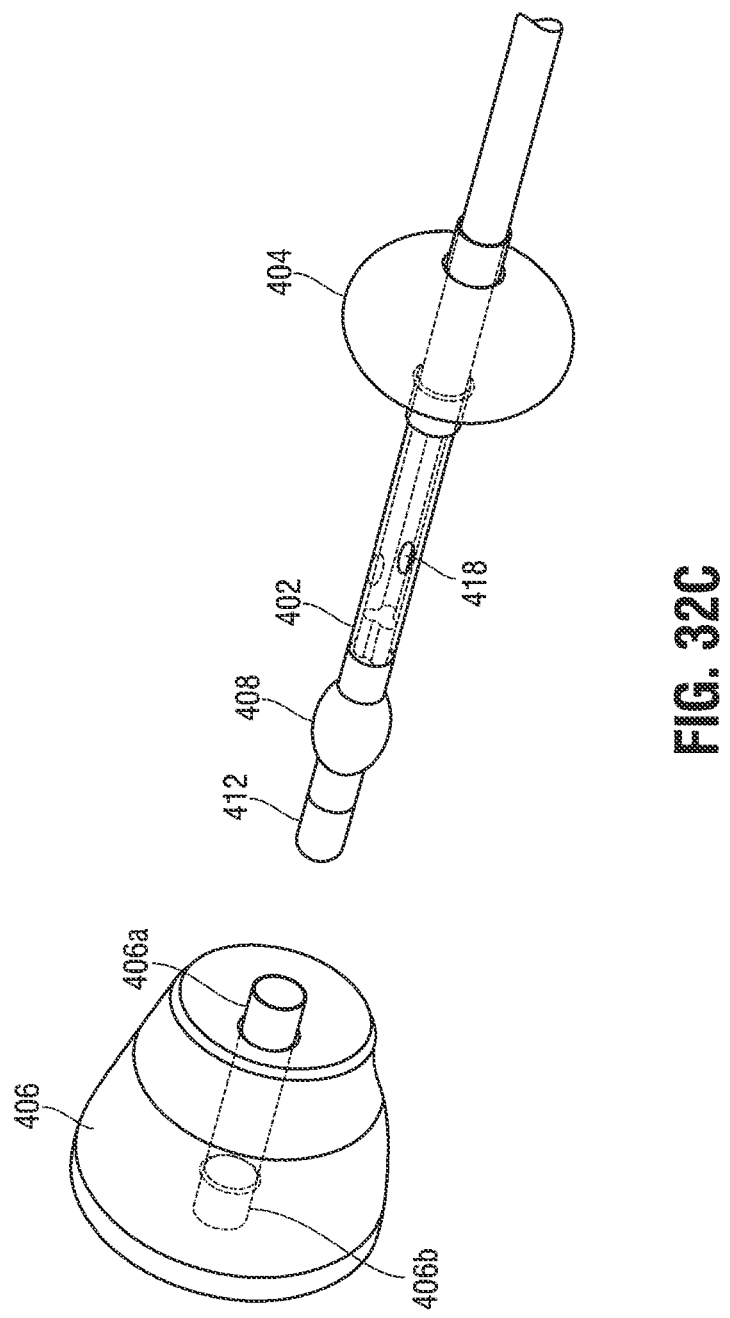
Figure 32D:
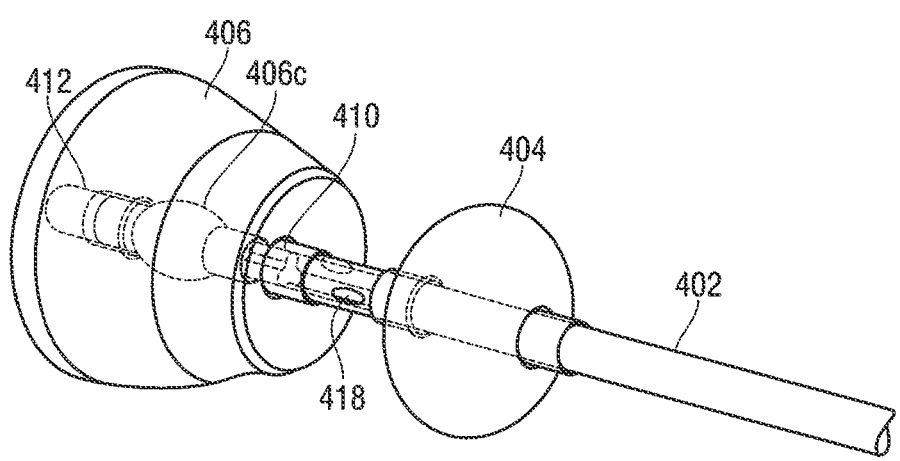
Figure 33:
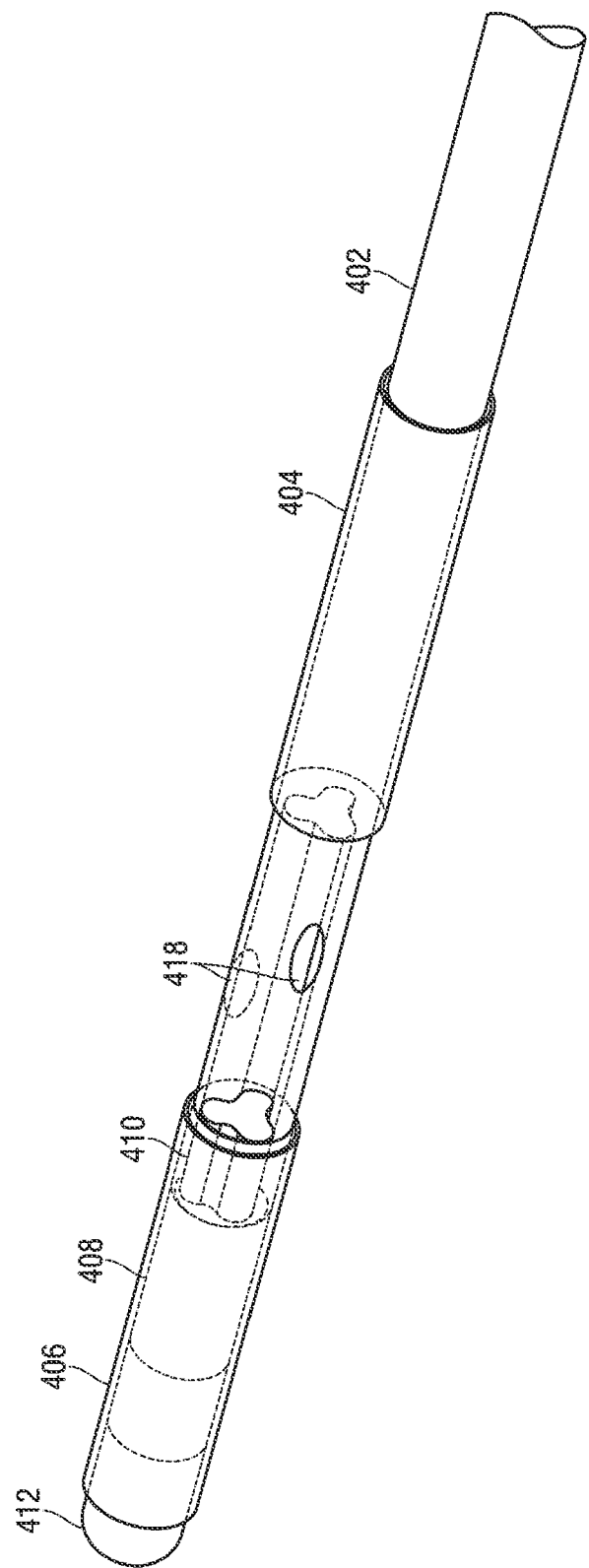
FIG. 33 is a side perspective of the distal end of the catheter of FIG. 30A showing the balloons in the deflated condition.

Next, with reference to FIG. 32B, the inner balloon 408 is placed over the bonding pin 410 and proximal and distal extensions 408a, 408b are attached, e.g., welded, to the bonding pin 410. The balloon 408 is attached to the center cylindrical region of the pin 410, leaving the proximal and distal extensions 414a, 414b exposed. In the illustrated embodiment, the inner balloon 408 is composed of the same material as the bonding pin 410 and both the bonding pin 410 and inner balloon 408 are composed of a different material than the distal region 402a of the shaft 402. (The distal region 402a can be the same material as the remainder or other portions of the shaft 402 or composed of a different material). After placement of the inner balloon 408 over the bonding pin 410, and either before or after attachment (e.g., welding) of the inner balloon 408 to the pin 410, distal tip or plug 412 is placed over distal extension 414b of pin 410 (FIG. 32C). Distal tip 412 has an opening 416 to receive extension 414b and is mechanically fixed, e.g., by a press fit, to the pin extension 414b. As shown, the tip 412 is spaced distally from the inner balloon 408. The tip 412 in some embodiments is composed of a different material than the core pin 410 and is preferably composed of the same material as the outer balloon 406, e.g., silicone, although other materials can be utilized. FIG. 32D illustrates the next step in assembly as the outer balloon 406 is inserted over the distal tip 412 and over the inner balloon 408 and bonded at a proximal extension 406a to the outer shaft 402 and at the distal extension 406b to the tip 412. Thus, as can be appreciated, in this embodiment, the outer balloon 406 is bonded at both ends to structure composed of the same material as the outer balloon 406; and the inner balloon 408 is bonded at both ends to structure composed of the same material as the inner balloon 408. Also, the retention balloon 404 is bonded at both ends to structure composed of the same material as the retention balloon 404. In other words, as can be appreciated, the embodiment of FIGS. 31-34 enables inner and outer balloons of different materials to be attached to the shaft of the catheter, e.g., materials that do not bond. Additionally, or alternatively, it enables a balloon of a different material than the shaft to be attached to the shaft. In one embodiment by way of example, the shaft is composed of silicone, the inner balloon is composed of EVA and the outer balloon is composed of silicone so EVA is bonded to EVA and silicone is bonded to silicone. In such embodiment, the core pin by way of example is composed of EVA. It should be appreciated that these materials are provided by way of example as other materials are also contemplated.

Figure 34:
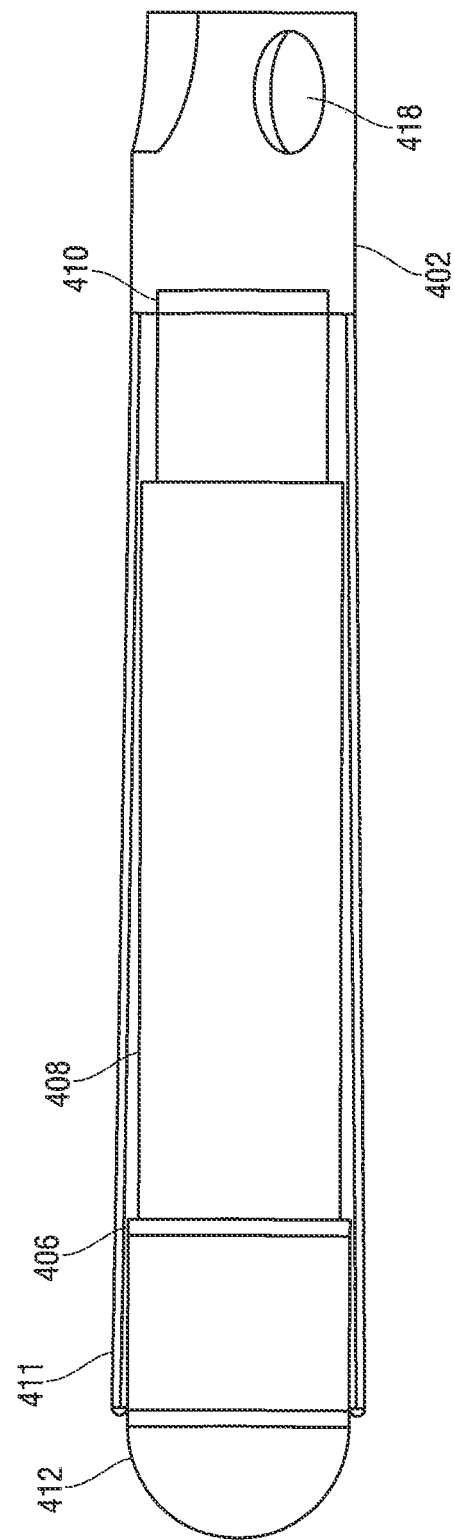
FIG. 34 is a close up view of the outer balloon of FIG. 33 in the deflated condition shown folded over itself.
Figure 35:
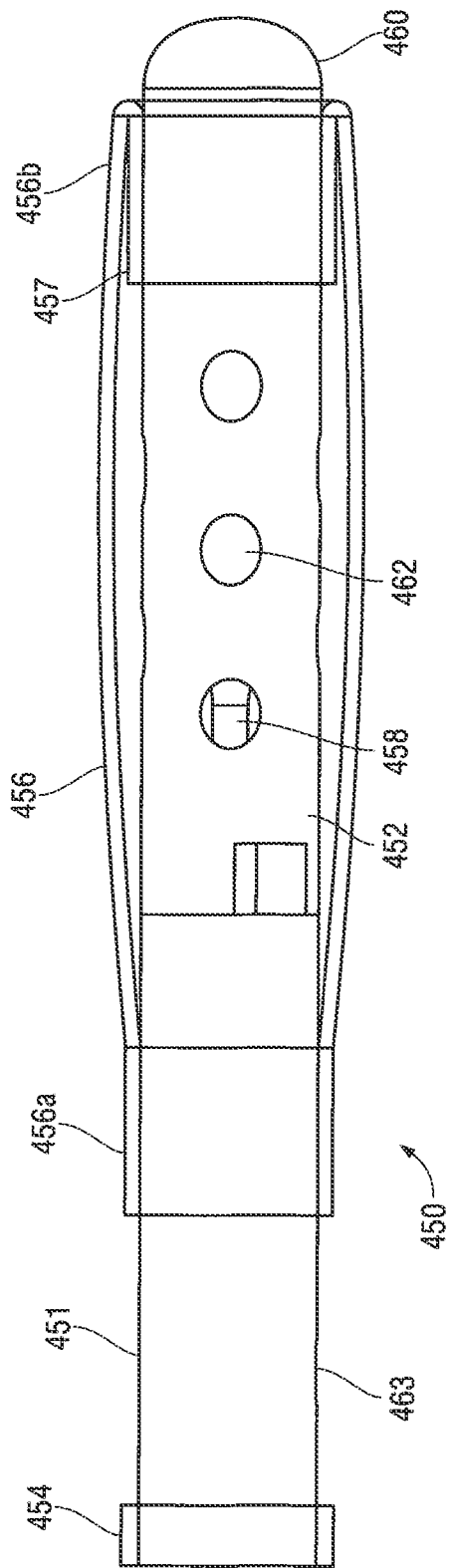
FIG. 35 is a side view of the distal region of the catheter of an alternate embodiment.
Figure 36:
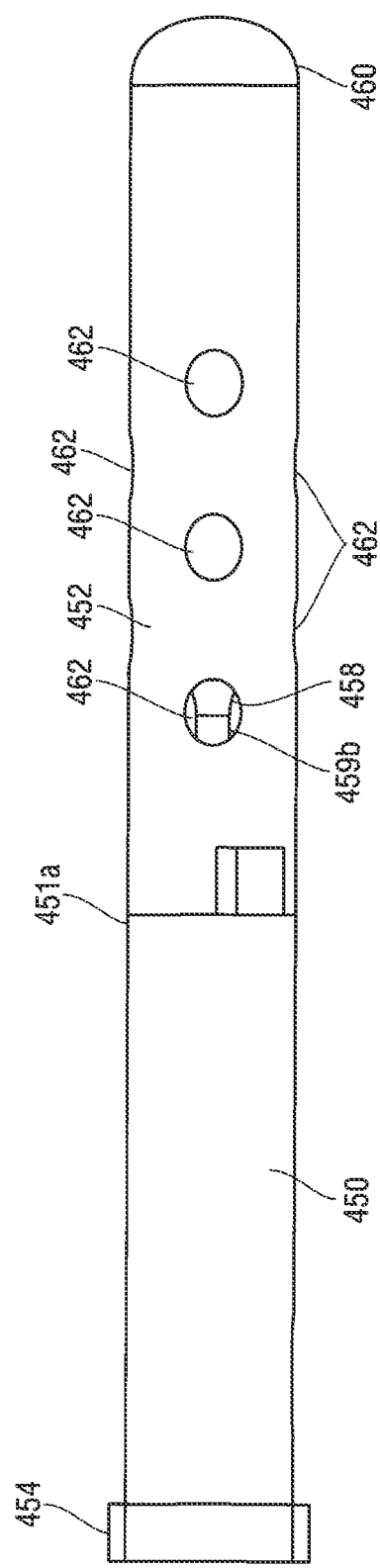
FIG. 36 is a view similar to FIG. 35 with the outer balloon removed for clarity.

In some embodiments, the outer balloon 406 is folded over itself as shown in FIG. 34 to allow the balloon 406 when inflated to extend out and fully cover the distal tip 412. Thus, the outer balloon 406 in its deflated condition has a distal cuff 411 which exposes the distal tip 412 for atraumatic insertion of the catheter 400, and expands to cover the distal tip 412 when inflated when the catheter 400 is fully inserted and placed at the target location. The balloons 404, 406 and 408 can be of the various shapes of the stabilizing, outer and inner balloons disclosed herein. In FIGS. 30A to 34 the outer balloon 406 by way of example is shown as pear shaped.

FIGS. 30A-34 illustrate the fully assembled catheter 400 which is used to measure pressure in the same manner as catheter 200 of FIG. 18A. Thus, a transducer hub 430, which can be any of the transducer hubs disclosed herein, such as hub 240 of FIG. 24A, hub 300 of FIG. 28A, etc., is attached to port 420 to advance gas, e.g., air through the lumen to inflate inner balloon 408. The lumens 438, 434 for inflation of the inner balloon 408 and outer balloon 406 are radially spaced from core pin 410 as core pin occupies the drainage lumen 432 (distal of side openings 418) and does not interfere with the balloon inflation lumens 434, 438.

Side opening(s) 418 in catheter 400 communicate with the drainage lumen 432 for draining the bladder. As shown, the drainage opening(s) 418 in this embodiment is positioned between the a) outer balloon 404/inner balloon 408 and b) retention balloon 404. More than one drainage opening can be provided. It should be appreciated that such location of the drainage opening(s) between the retention balloon and pressure balloon(s), rather than distal of the pressure balloon(s) can be utilized with any of the catheter embodiments disclosed herein.

As noted herein, the catheters of the present invention can be utilized for measuring other pressure in a patient and are not limited to intra-abdominal pressure nor limited to measuring bladder pressure.

In the foregoing embodiments, the inner balloon is positioned within the outer balloon (with its outer wall radially spaced from the outer wall of the outer balloon) and deformation of the outer balloon based on changes in pressure within the patient, e.g., within the bladder in response to abdominal pressure, causes deformation of the inner balloon as the fluid within the outer balloon (or wall) exerts a pressure against the wall of the inner balloon. This deforms the inner balloon to provide a pressure reading. In the alternate embodiment of FIGS. 35-41, the inner balloon is positioned within a chamber (or cage). This chamber forms an inner balloon encapsulating member as it encircles/encapsulates the inner balloon and is positioned between the inner balloon and outer balloon. Thus, the encapsulating member (chamber) separates the outer wall of the inner balloon from the interior of the outer balloon. However, the chamber has a series of openings so that the fluid within the outer balloon can pass through the chamber and apply a pressure against the outer wall of the inner balloon to deform the inner balloon to provide pressure readings in the same manner as the other embodiments disclosed herein. As in other outer/inner balloon embodiments, the catheter can be used is a voided cavity, e.g. a voided bladder, since fluid, e.g., water, does not need to be injected since the fluid within the outer balloon acts as a transmission medium.

With reference now to FIGS. 35-41, the catheter 450 has an elongated shaft 451. Note only the distal end of the catheter 450 is shown; the proximal end, hub, connector, etc. being the same as in the foregoing inner and outer balloon embodiments, e.g., catheter 200 of FIG. 18A. The catheter 450 has a retention balloon 454 identical to retention (stabilizing) balloon 206 of catheter 200 (or other stabilizing balloons disclosed herein), an inner balloon 458 and an outer balloon 456. In the gap (space) between the proximal end of the outer balloon 458 and the distal end of the retention balloon 454, is a drainage hole 463 (or multiple drainage holes) for draining the cavity, e.g., the bladder. A thermistor can be placed adjacent the drainage opening 463 for temperature readings, and the thermistor wire can extend through a lumen of the catheter 450, e.g., the drainage lumen, the pressure lumen or a separate lumen, for electrical connection to a temperature monitor. Catheter 450 has three lumens: 1) lumen 486 communicating with outer balloon 456 for inflating outer balloon 456; 2) a lumen communicating with the retention balloon 454 to inflate retention balloon 454; and 3) drainage lumen 484 having one or more side openings 463 at a distal region of the catheter for drainage of the bladder. In this embodiment, the tubular portion of the inner balloon 458 is positioned within the drainage lumen. In an alternate embodiment such as the embodiment of FIGS. 42-46 discussed below, a separate lumen can be provided to receive the tubular portion of the inner balloon.

The outer balloon 456 has a proximal end 456a attached to the shaft 451 and a distal end 456b attached to the chamber 452. The outer balloon 456 can include a cuff 457 like cuff 411 of outer balloon 406 of FIG. 34 wherein it is folded over itself to expose the atraumatic tip 460 of the catheter 450 (the atraumatic tip of the chamber 452) and when expanded covers the tip 460. In one embodiment, the spacing between the proximal end of the outer balloon 456 and the distal end of the retention balloon 454 is about 20 cm but other spacings/distances are also contemplated.

Figure 37:
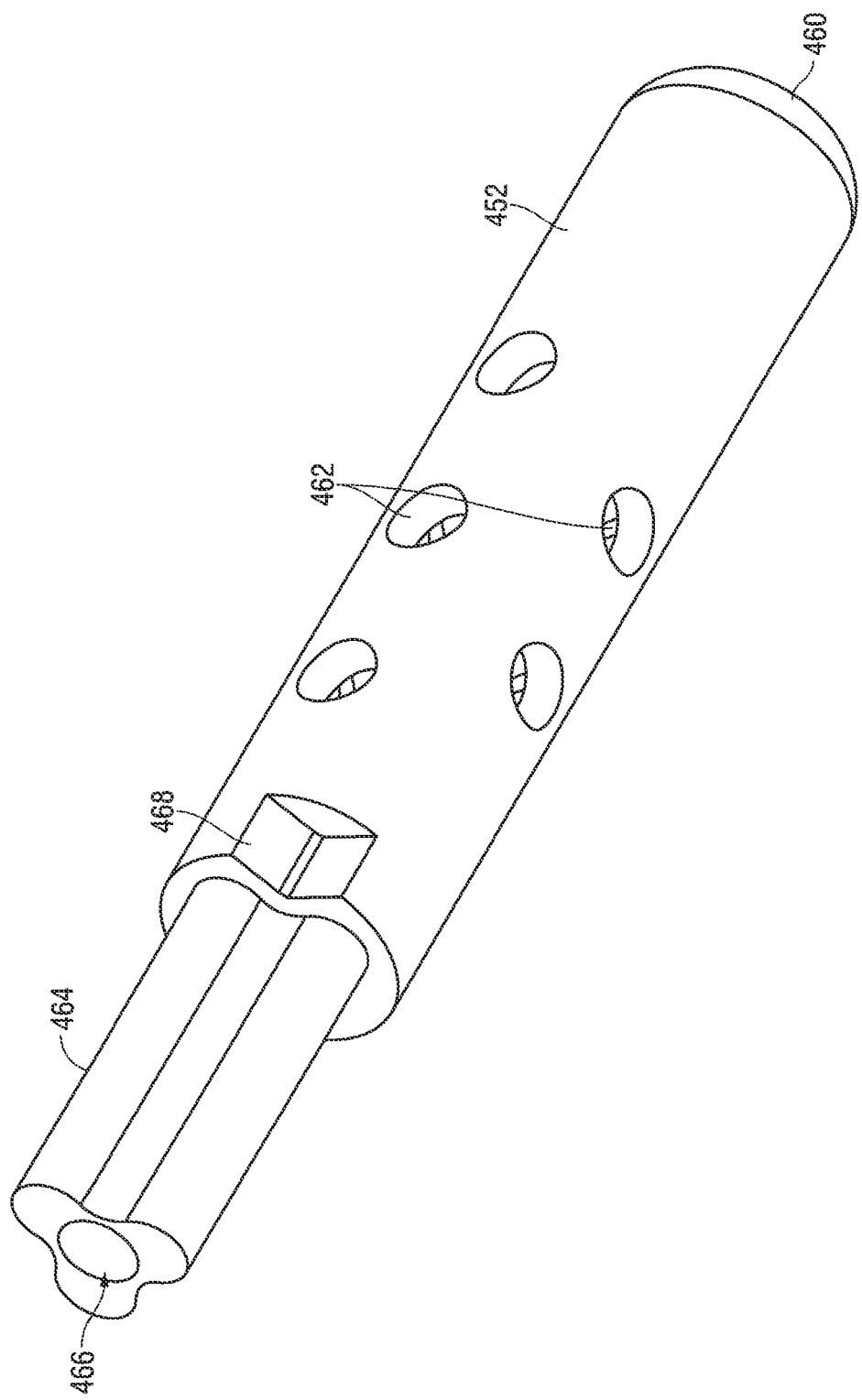
FIG. 37 is a perspective view of the inner balloon chamber of the catheter of FIG. 35.
Figure 38:
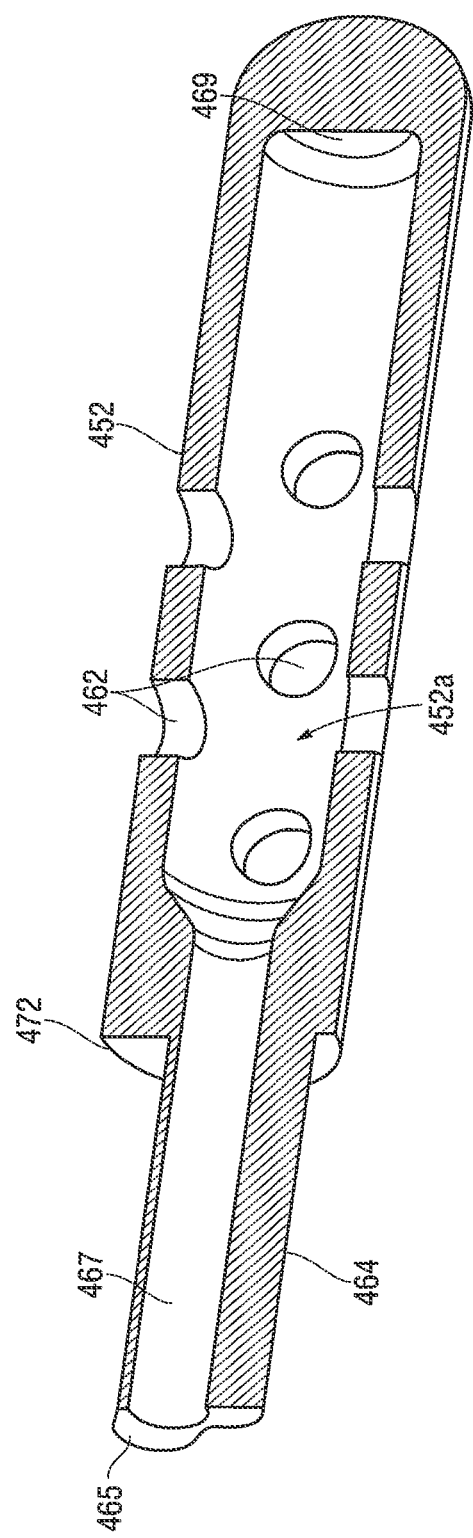
FIG. 38 is a cutaway view of the chamber of FIG. 37.
Figure 39:
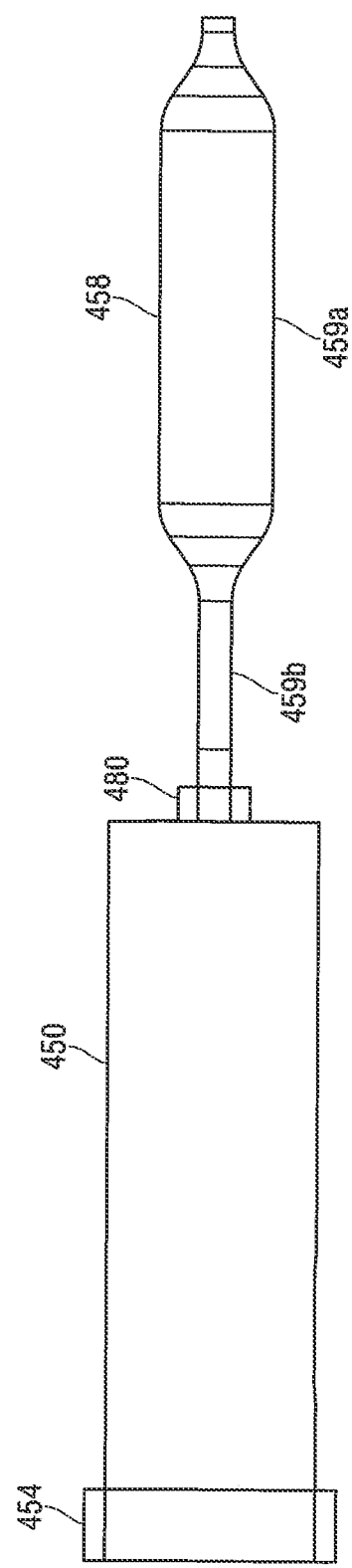
FIG. 39 is a view similar to FIG. 35 with the outer balloon and chamber removed for clarity.
Figure 40:
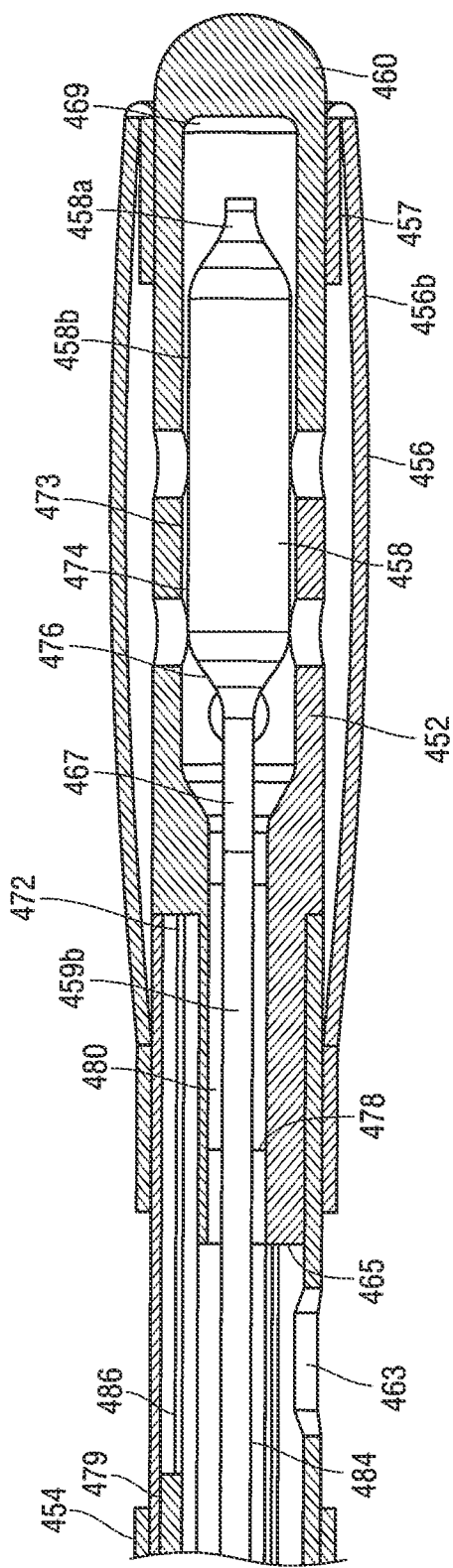
FIG. 40 is a cutaway view of the catheter of FIG. 35.
Figure 41:
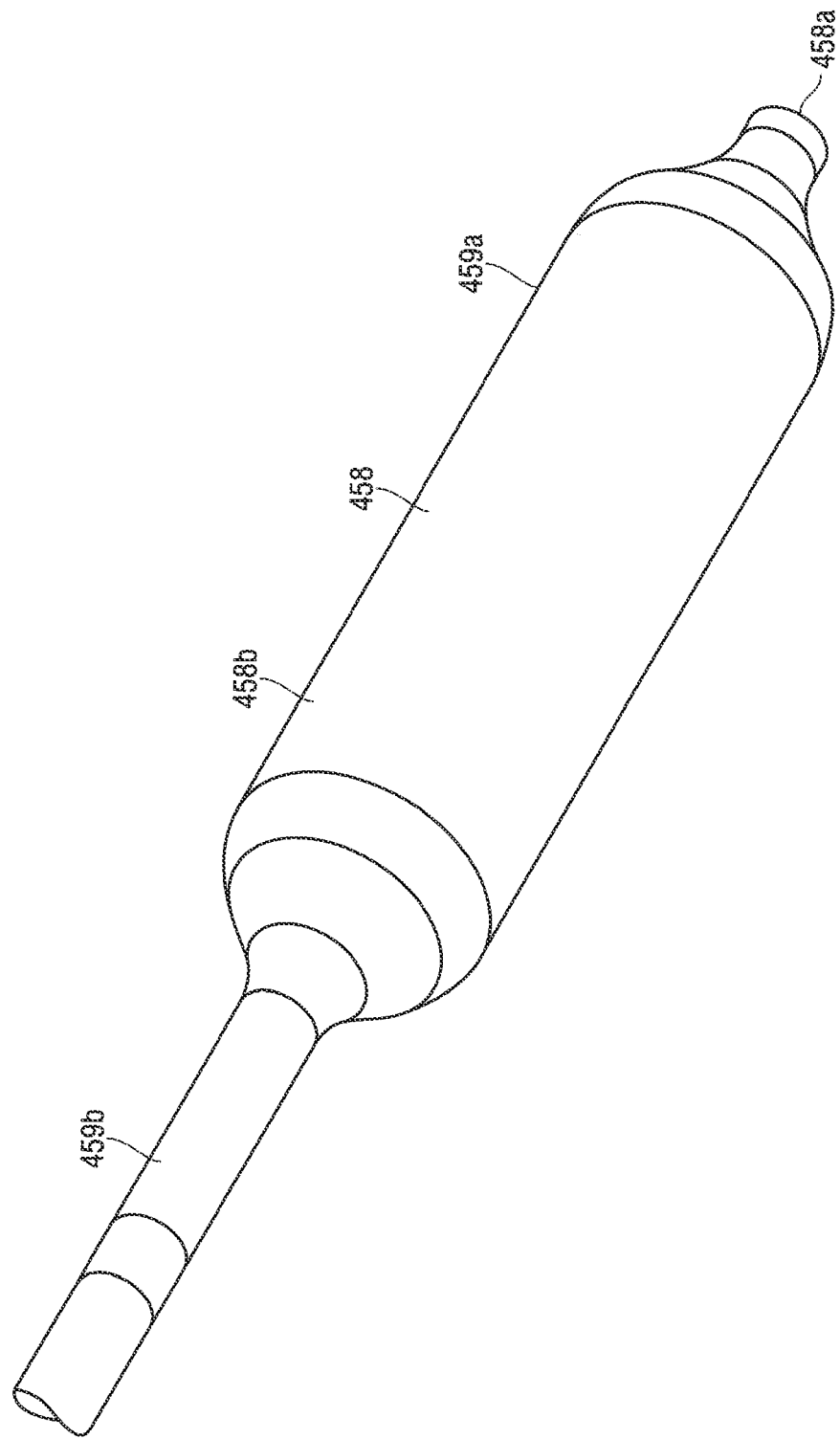
FIG. 41 is a perspective view of the inner balloon of the catheter of FIG. 35.
Figure 42:
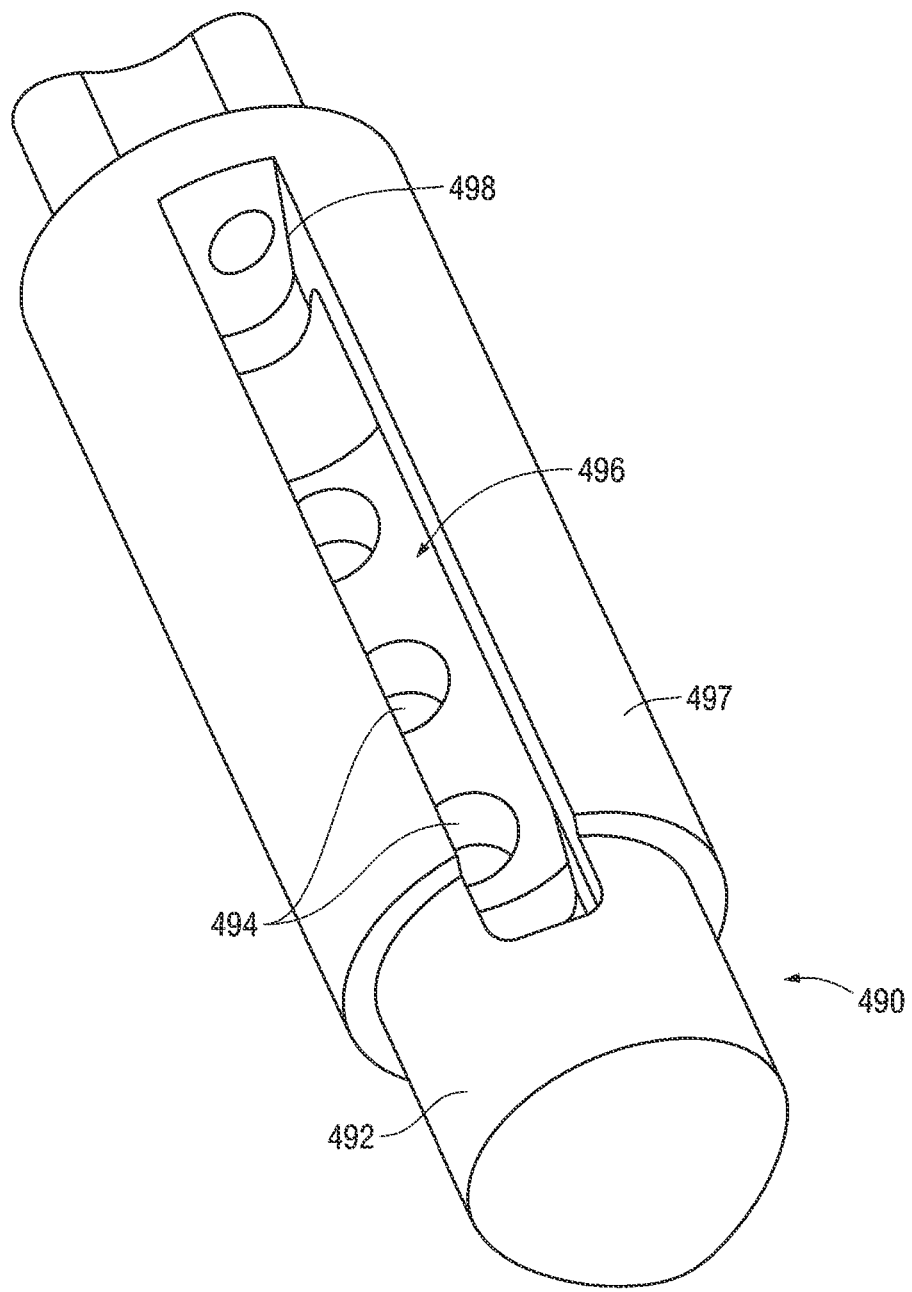
FIG. 42 is a perspective view of an alternate embodiment of the inner balloon chamber.
Figure 43:
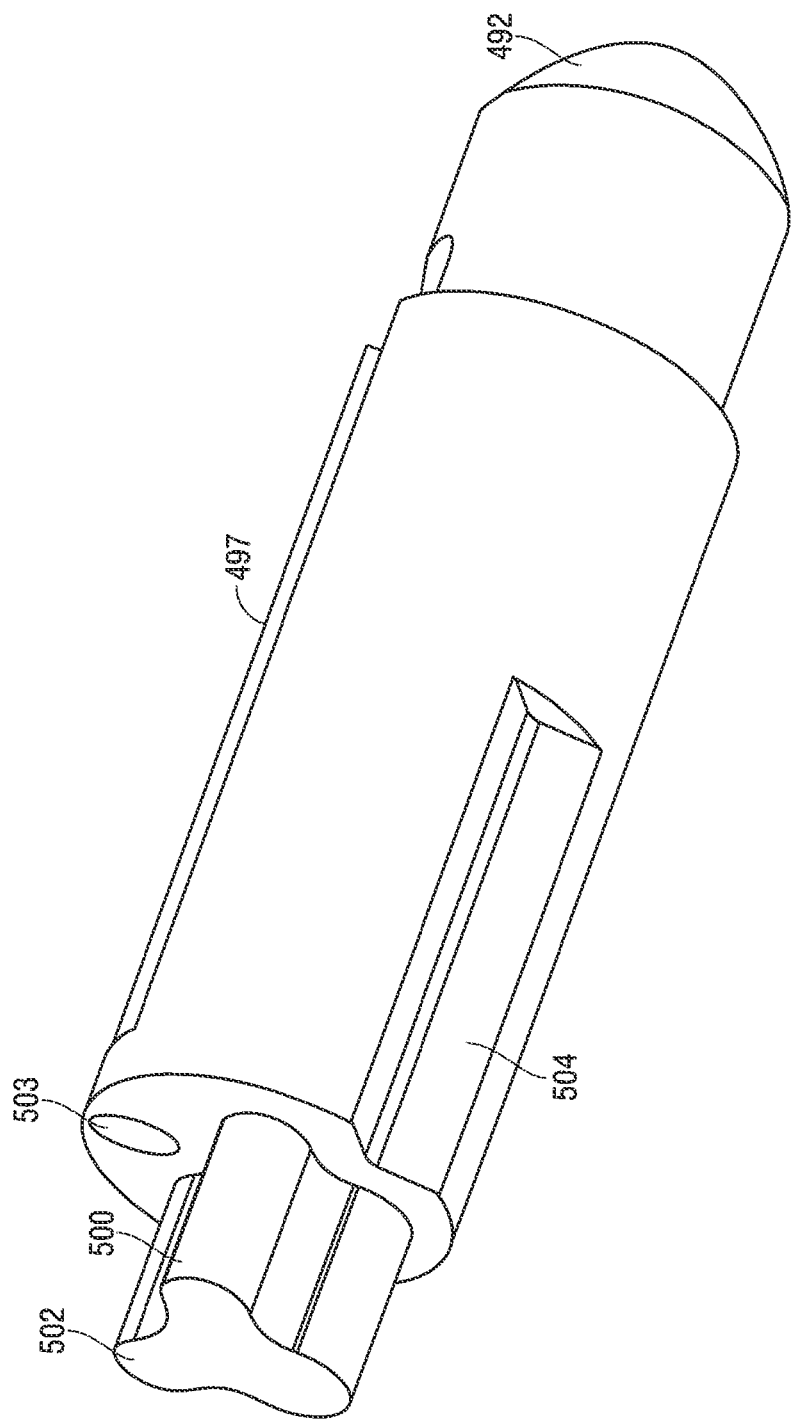
FIG. 43 is a perspective view of the chamber of FIG. 42 from the other side.
Figure 44:
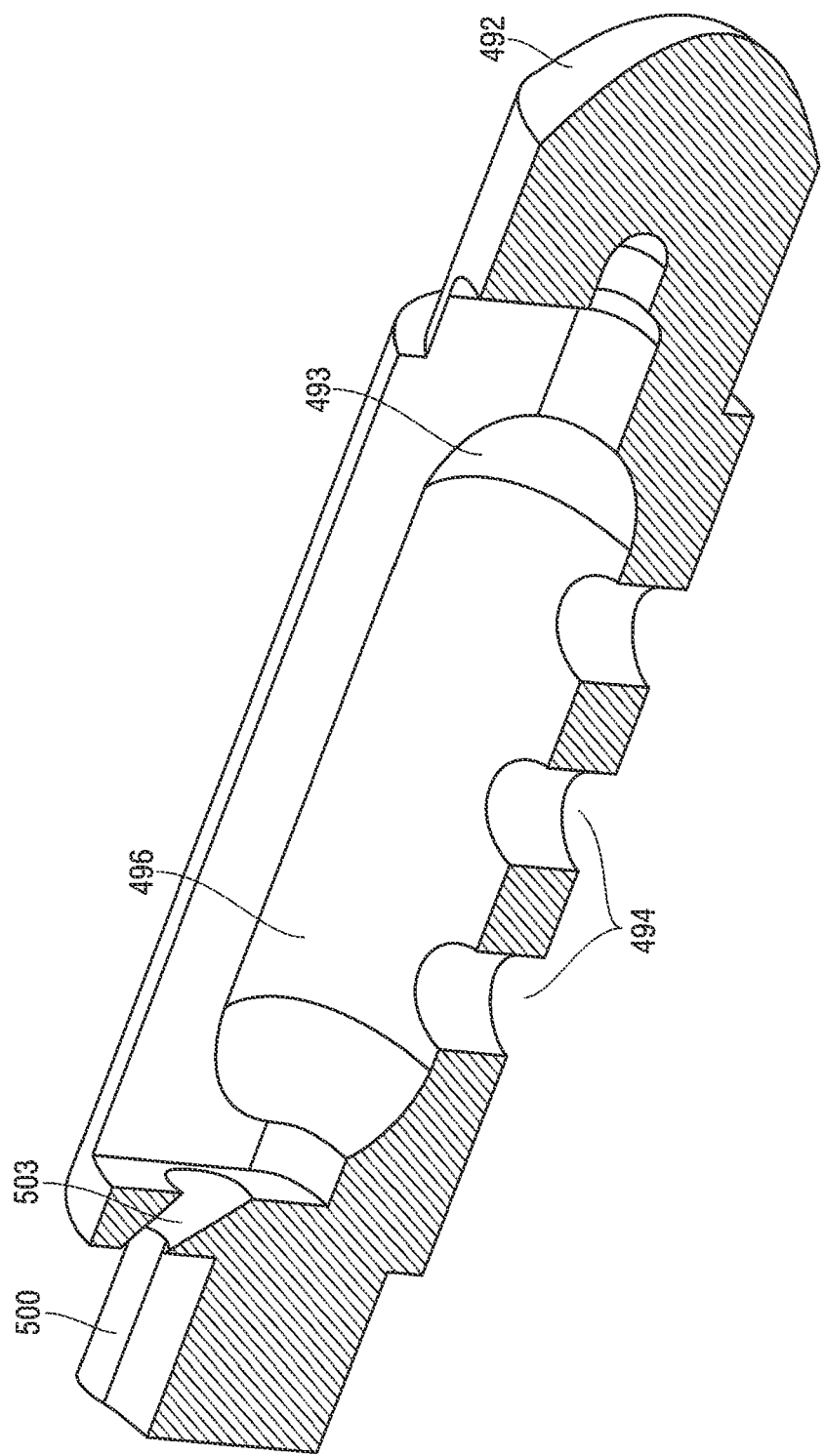
FIG. 44 is a cutaway view of the chamber of FIG. 43.
Figure 46A:
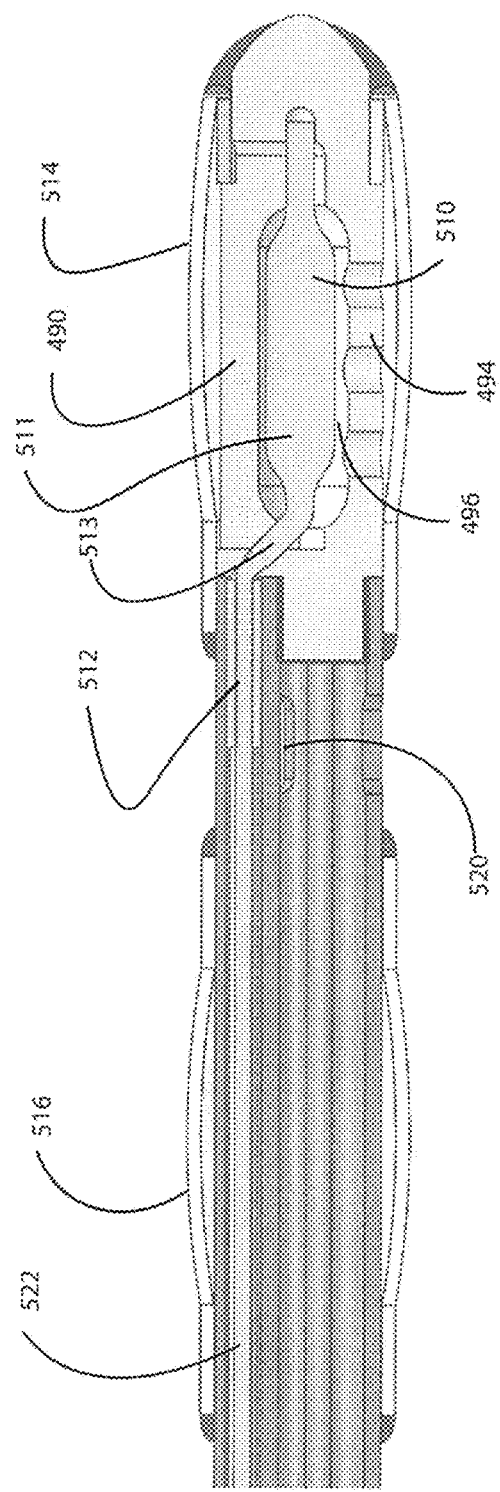
FIG. 46A is a cutaway view similar to the cross-sectional view of FIG. 45.
Figure 46B:
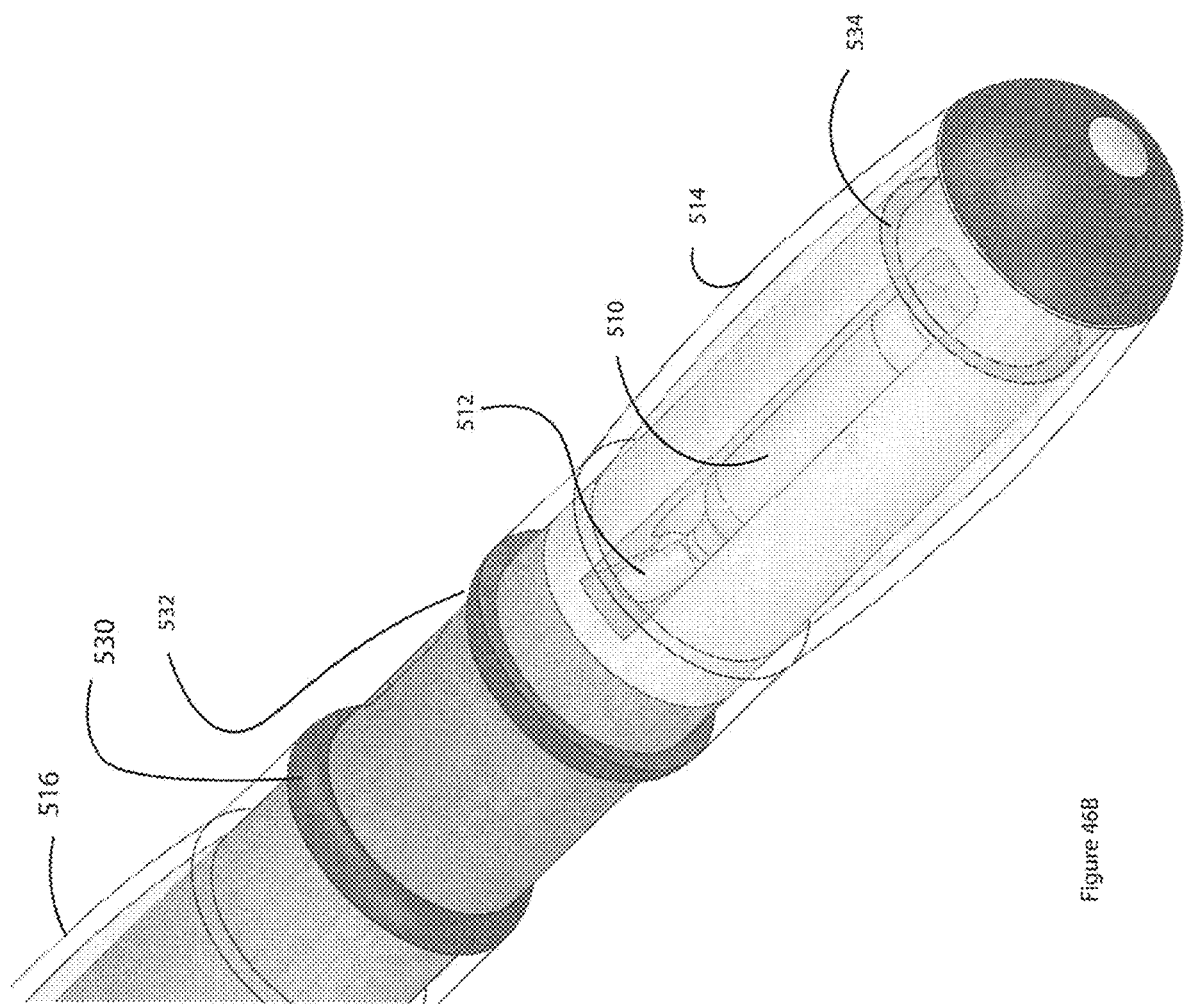
FIG. 46B is a perspective view of the distal end of the catheter of FIG. 46.

The chamber 452 forms the distal end region of the catheter 450 as it extends distally from the distal edge 451a of shaft 451. With reference to FIGS. 37 and 38, chamber 452 has a reduced diameter proximal extension 464 for press fit and attachment within the distal end of shaft 451. Opening 466 in chamber 452 communicates with lumen 467 which extends through proximal extension 464, terminating at cavity 452a of chamber 452. Opening 468 lines up with outer balloon inflation channel for inflating the outer balloon. Chamber 452 has a wall 472 forming a shoulder for abutment with distal wall 459 of shaft 451 (see FIG. 40). Cavity 452a is dimensioned to receive the inner balloon 458 in the deflated condition as well as in the inflated condition. As shown in FIG. 40, in the inflated condition, a small gap 473 exists between the outer wall 458b of the inner balloon 458 and the inner wall 474 of the chamber 452. In some embodiments, the gap is about 0.020 inches although other sized gaps (spacing) are also contemplated. Cavity 452a terminates distally at wall 469. In some embodiments, a wire can extend through the inner balloon 458 and be embedded in wall 469 (pierces the wall 469) to help stabilize and center the inner balloon 458. Such wire can extend proximally from wall 469, through cavity 452a and through lumen 467 and extend through a lumen in the catheter, extending through the entire, or alternatively, a partial, length of the catheter.

Chamber 452 also includes a plurality of openings 462 (only some of which are labeled for clarity) to provide fluid (liquid or gas) flow from the outer balloon 456 against the outer wall 458b of the inner balloon 458 retained within the chamber 452. Thus, the chamber 452 separates the outer wall 458b of the inner balloon 458 from the interior of the outer balloon, except for the communication through the openings 462 in the chamber 452. (The inner and outer balloons are sealed from each other so they are not in fluid communication with each other). One arrangement of chamber openings is shown by way of example in FIGS. 37 and 38, with two rows of three longitudinally aligned openings (holes) and two rows of two longitudinally aligned openings, each row spaced apart radially around the circumference of the chamber 452. The rows are shown equidistantly spaced but other arrangements are also contemplated. Also, a fewer or greater number of rows can be provided and a different number of holes than the number shown can be provided. Holes of different sizes than shown, as well as holes of varying size in the chamber 452, are also contemplated. The chamber 452 can be made of silicone, although other materials are also contemplated.

The inner balloon 458 has balloon portion 459a and a tube portion 459b. The tube portion 459b extends through lumen 467 of chamber 452 and through lumen 484 in the catheter shaft 451. The tube portion 459b can extend the entire length of the catheter 450 such that it terminates adjacent the inflation port; alternatively, it can terminate within the lumen 484 of the shaft 451 or within the lumen 467 of the chamber 452 in which case inflation fluid, e.g., gas such as air, would flow through the shaft lumen (and through lumen 467 in the latter embodiment) for a certain length where it would then enter an opening in the tubular portion 459b for flow into the inner balloon 458. The inner balloon 458 can be made of polyamide such as nylon, although other materials are also contemplated, such as EVA. The inner balloon 458 can be made of various dimensions, and in one embodiment by way of example the full balloon diameter is about 3.5 mm, the balloon length is about 10 mm and the wall thickness is about 0.05 mm. By way of example, the inner diameter tubular portion 459b of the inner balloon 458 could be about 0.2 mm. Other balloon dimensions are also contemplated. A wire could be provided to fill the gap to reduce the air column. The distal end of the inner balloon 458 can be welded or soldered or sealed by other methods.

Note in the embodiments wherein the inner balloon has an elongated tubular portion extending through the lumen of the catheter, the tubular portion can be integral with the enlarged region of the balloon that receives the fluid contact from the outer balloon. In alternative embodiments, the tubular portion can be a separate component attached to the balloon portion. In other embodiments, the tubular portion can be in the form of a metal tube extending through the lumen of the catheter and attached to the tail of the inner balloon. In any of these versions, the tubular portion along with the balloon portion form the gas chamber. In some embodiments, the tubular portion can extend through the entire or almost the entire length of the lumen of the catheter and terminate at the proximal end adjacent the distal end of the elongated member (rod) of the hub used to inflate the inner balloon. In other embodiments, it can terminate more distal.

A sealant or plug 480 can be provided, the plug 480 positioned around the tubular portion 459b of the inner balloon 458 which closes off the lumen 467 distal of the drainage hole 463. The plug 480 could also help maintain the centering of the tubular portion 459b. Plug 480 abuts inner wall 478 of chamber 452 as shown in FIG. 40. The plug in one embodiment is made of RTV silicone.

A thermistor can be positioned adjacent the drainage opening(s) 463 and the temperature sensor wires can be positioned in lumen 484, running parallel to the balloon tubular portion 459b. Alternatively, the temperature sensor wires can be positioned in the same lumen as the lumen for filling the outer balloon or alternatively an additional lumen can be provided for the temperature sensor wire(s).

The outer balloon 456 could include a coating such a parylene to change the modulus of the balloon. That is, such coating could stiffen the balloon so it is not to continuously expanding under pressure, which could cause a reduced pressure reading. The coating can also cover all or part of the catheter which could add lubricity.

The inner and outer balloons disclosed herein can be filled to various volumes. In one example, the inner balloon can be filled to a volume of about 0.16 cc and the outer balloon can be filed to about 10 cc.

The inner and outer balloons disclosed in the various embodiments can be coated to reduce their permeability. That is, to prevent escape of air, the balloons can be made of an impermeable material and/or the balloons can be made of a permeable material and coated with an impermeable material. As used herein, impermeability means there is no (or negligible) pressure decay in the balloon over a period of time in which the catheter remains inserted into the body. This period of time could be for example from one day to up to 30 days. This period of time of catheter insertion, due to current hospital and clinical protocols, typically does not exceed 30 days, but impermeability of the balloons of the present invention can also mean little or no leakage for a longer period of time, e.g., 45 days, depending on the protocol for duration of catheter insertion.

Various features affect pressure decay which include the density of the balloon material, the material and/or structure of the balloon, and the type and/or density of coating on the balloon. The catheters of the present invention provide pressure loss management by limiting loss of pressure resulting from escape of air (or other gas) from the system. The pressure management, affected by these parameters, also needs to be balanced with the size and patient comfort restraints, which the catheters of the present invention achieve.

Additionally, the amount of dead space in the system can affect decay because if there is more gas (e.g., air) in the system, the percentage loss will have less of an overall effect than if there is less gas in the system. However, a larger gas chamber acts as a dampening affect so there is less responsiveness. Therefore, the catheters of the present invention achieve this balance of accurate pressure reading (due to maximized responsiveness) while minimizing or eliminating pressure decay in the necessary time period.

Catheter 450 can be used in the same manner as the catheters described above, and such aforedescribed use(s) are fully applicable to catheter 450, the difference being the caged inner balloon. Thus in use, catheter 450 is inserted into the cavity, e.g., bladder, and stabilizing balloon 454 is inflated to secure the catheter 450 in place. The system is charged by inflation of the inner balloon 458, i.e., preferably partially inflated for the reasons discussed above, by insertion of air through a side port which is in fluid communication with tubular portion 459*b*, or by mounting of the transducer hub as described herein, in a closed system formed by the internal space of the inner balloon 458 and the internal lumen and/or tubular portion 459*b* communicating with the internal space of inner balloon 458. Outer balloon 456 is filled, i.e., preferably partially inflated for the reasons discussed above, via injection of fluid such as air or saline through a separate lumen. With the outer balloon 458 inflated, pressure monitoring can commence as external pressure applied to the larger circumferential outer surface of the outer balloon 458 compresses and deforms the outer balloon 456 which forces fluid within the outer balloon 458 through openings 462 in chamber 452 against the outer wall of the inner balloon 458, compressing the inner balloon 458. As the inner balloon 458 is compressed and deformed in response to compression/deformation of the outer balloon 456 based on changes to bladder pressure, the sensor provides continuous pressure readings, communicated to an external monitor. Although, the system is capable of continuous pressure and continuous temperature monitoring, as in the other embodiments disclosed herein it can also be adapted if desired for periodic monitoring so the pressure and/or temperature readings can be taken at intervals or on demand by the clinician.

An alternate embodiment of the chamber (cage) is illustrated in FIGS. 42-46B and designated by reference numeral 490. Chamber 490 differs from chamber 452 in that it has a slot 496 for ease of assembly and has an angled channel 503 for receipt of the tubular portion of the inner balloon. More specifically, elongated slot 496 extends through an outer wall of the chamber 490 and allows the inner balloon 510 to be placed, e.g. top loaded, into the cavity 496 of the chamber 490. The inner balloon 510 is identical to inner balloon 458 described above except that the tubular portion 512 extending proximally from balloon portion 511 is angled at portion 513 so that the tubular portion 512, rather than being placed in the drainage lumen as in FIG. 40, is placed in a separate lumen 522. Angled channel 503 in chamber 490 receives the angled portion 513 of balloon 510.

Like chamber 452, chamber 490 has a series of openings 494 to provide fluid (liquid or gas) flow from the outer balloon 510 against the outer wall of the inner balloon 510 retained within the chamber 490. Thus, the chamber 490, like chamber 452, separates the outer wall 458*b* of the inner balloon 458 from the interior of the outer balloon 514, except for the communication through the openings 494 in the chamber 490. One arrangement of chamber openings is shown by way of example in FIG. 42, with one row of three openings (holes), however, other arrangements are also contemplated. Also, a greater number of rows can be provided and a different number of holes than the number shown can be provided as well as holes of different sizes than shown and holes of varying size in the chamber 490. The chamber 490 can be made of silicone, although other materials are also contemplated.

Chamber 490 has a reduced diameter proximal extension 502 for press fit and attachment within the distal end of the catheter shaft. Slot 504 in chamber 490 communicates, i.e., aligns, with lumen 528 for inflating outer balloon 514. A wire can extend through the inner balloon 510 and be embedded in a wall 493 (pierces the wall 493) to help stabilize and center the inner balloon 510.

The catheter has four lumens: 1) lumen 522 receiving the tubular portion 512 of the inner balloon 510; 2) lumen 528 communicating with outer balloon 514 for inflating outer balloon 514; 3) lumen 526 communicating with the retention balloon 516 to inflate retention balloon 516; and 4) drainage lumen 524 having one or more side openings 520 at a distal region of the catheter for drainage of the bladder. In this embodiment, the tubular portion 512 of the inner balloon 510 is positioned in a separate lumen as shown. Except for the angled portion 513, the inner balloon 510 is identical to the inner balloon 458 of FIG. 41. The outer balloon 514 and retention balloon 516 function in the same manner as outer balloon 456 and retention balloon 454 of FIG. 40. The balloons can be of the various configurations described herein, or alternatives thereof. A thermistor can be positioned in lumen 522 or in another lumen. In all other respects, the catheter of FIGS. 43-47 functions in the same manner as catheter 450. Therefore, the discussion of the structure, features and function of catheter 450 is fully applicable to the catheter of FIGS. 43-47.

Figure 47C:
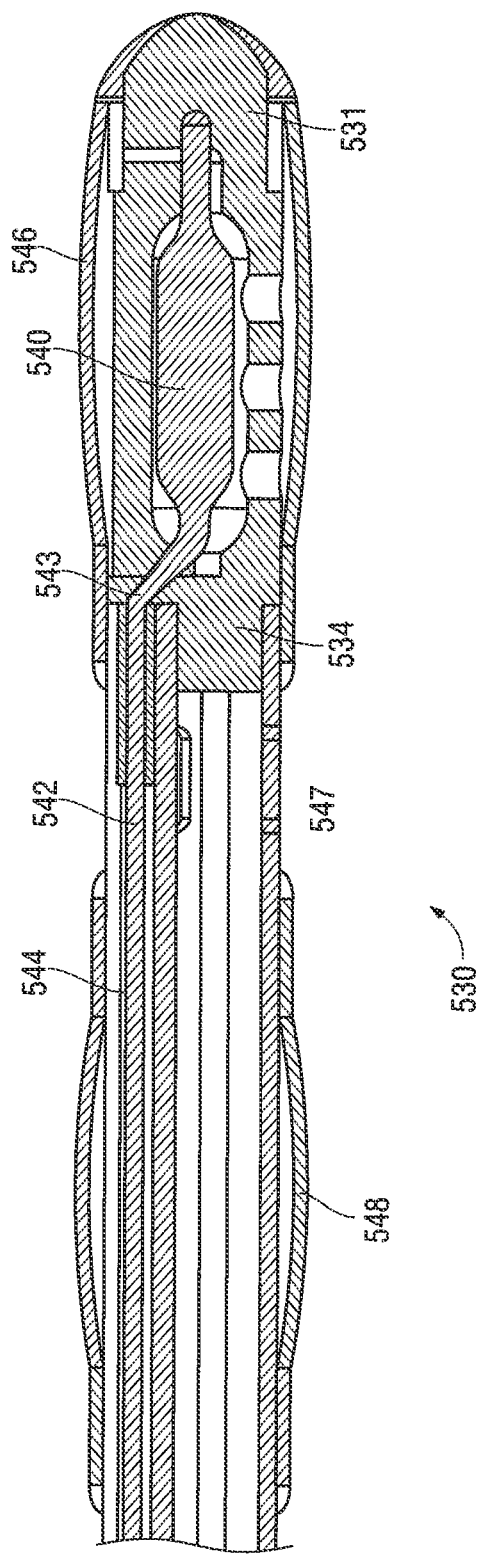
FIG. 47C is a cutaway view similar to the cross-sectional view of FIG. 47A.
Figure 48A:
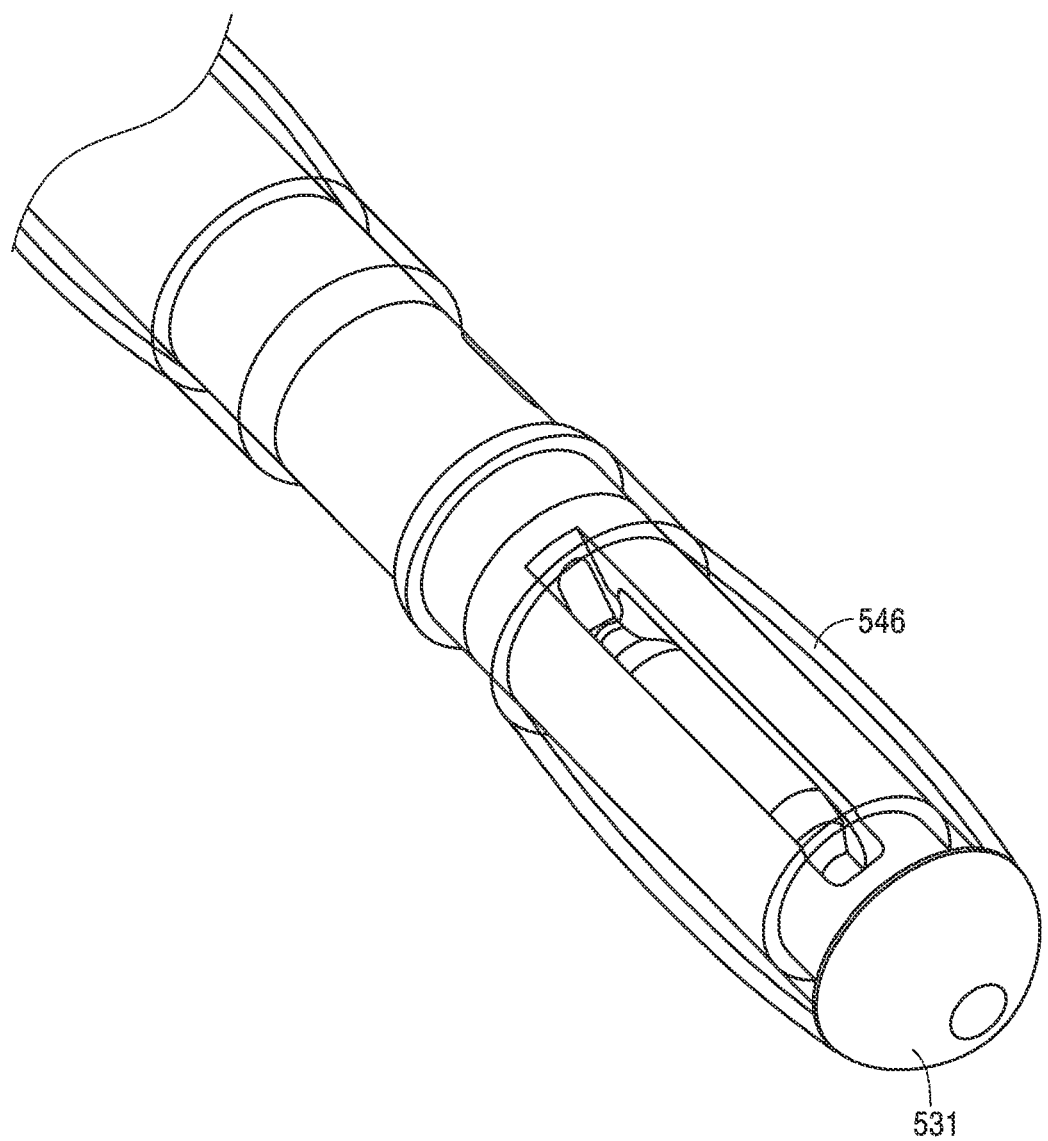
FIG. 48A is a perspective view of the distal end of the catheter of FIG. 47A.
Figure 48C:
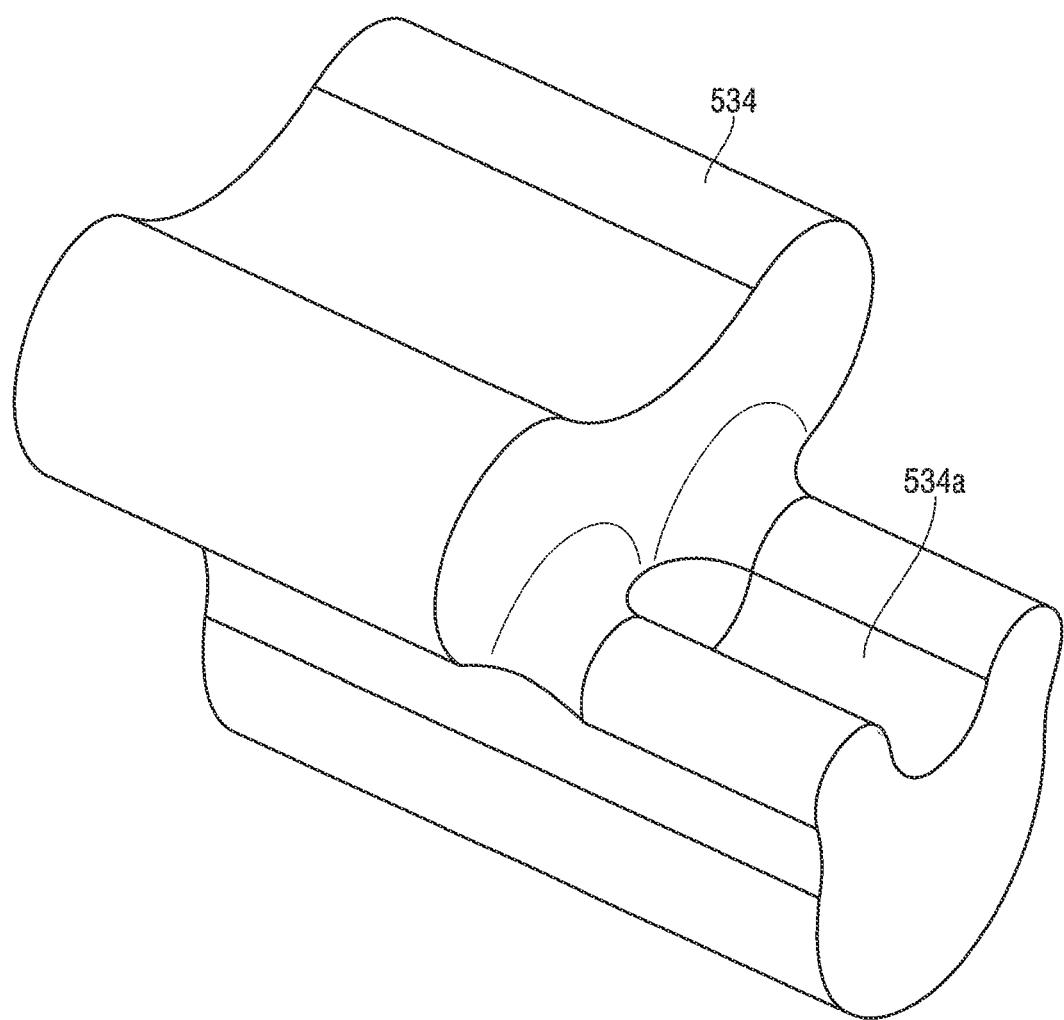
FIG. 48C is a perspective view of the plug of the catheter of FIG. 47A.
Figure 49:
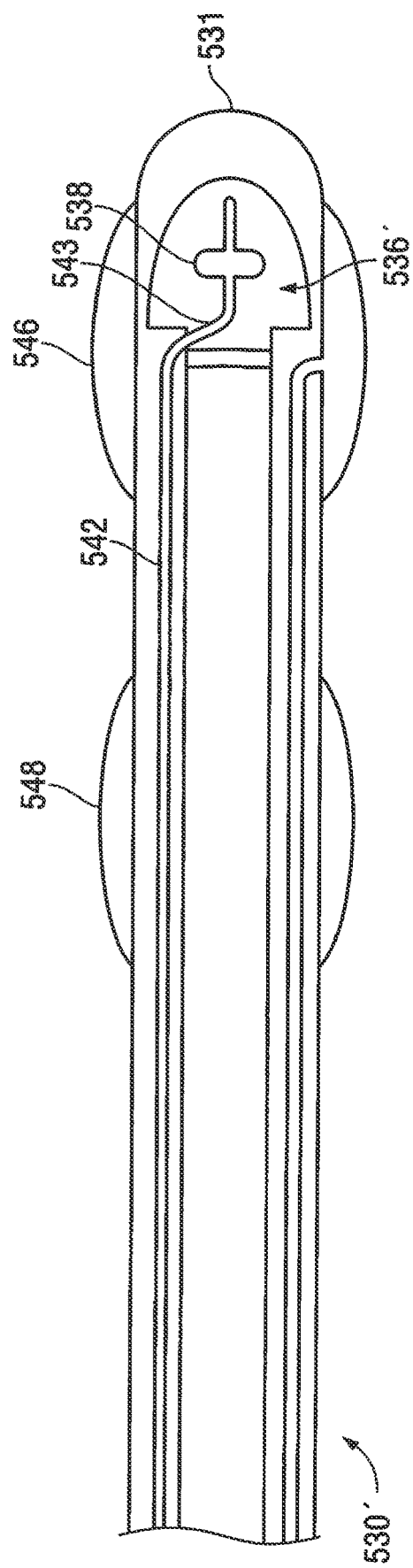
FIG. 49 is a side view of an alternate embodiment of the catheter of the present invention.

FIGS. 47A-47C illustrate an alternative embodiment of the catheter of the present invention. In these embodiments, the catheter does not include the cage. Catheter 530 has an inner drainage lumen 532 having a distal plug or seal 534 which seals the drainage lumen 532 distal of the plug 534 to form a distal region or area of 536 sealed from the drainage lumen 532. Positioned within the sealed off region 536 is inner balloon 538. Inner balloon 538 has a balloon region 540 and a tubular region 542 extending proximally therefrom. The plug 534 has a recess 534*a* (FIG. 48C) to receive tubular region 542 of the inner balloon 538. Tubular region 542 has an angled region 543 so that the tubular region 542 is positioned in a separate lumen (lumen 544) than the drainage lumen 532. The distal region 536 can be of the same diameter as the drainage lumen 532 as shown in FIG. 48A or alternatively, can be larger (wider) than the drainage lumen 532 as in the embodiment of FIG. 48B showing widened sealed region 536' of catheter 530'. In all other respects, catheter 530' is identical to catheter 530 so like reference numerals are used for like parts. A plurality of openings are provided in distal region 536 for fluid communication from the outer balloon through the openings and against the outer wall of the inner balloon 538 to deform the inner balloon 538 as in the embodiments of FIGS. 35-47. The catheter can have a cap 531 at the distal end to provide a blunt tip for the catheter. The cap 531 has a recess 531*a* (FIG. 48B) to receive a distal extension of the balloon 538.

Inner balloon 538 functions in the same manner as inner balloon 458. Catheter 530 has an outer balloon 546 and a retention (stabilizing) balloon 548 which function in the same manner as outer balloon 456 and retention balloon 454 of FIG. 40 with inflation lumens 545, 547 (FIG. 47B). The balloons can be of the various configurations described herein, or alternatives thereof. A thermistor can be positioned in lumen 544 or in another lumen. Catheter 530 of FIGS. 48*a* and 48B function in the same manner as catheter 450 and has e.g., a drainage lumen, a lumen for inflation of the outer balloon and a lumen for inflation of the retention balloon. Therefore the discussion of the structure, features and function of catheter 450 is fully applicable to the catheter 530 and 530'.

FIGS. 50A-63B illustrate an alternative embodiment of the catheter of the present invention that does not include the cage. By placement of the inner balloon within the lumen of the catheter without a cage, it reduces the stiffness of the catheter and reduces cost. This embodiment also has the advantages of keeping the inner pressure balloon centered to reduce or prevent false pressure readings. The inner balloon expands within the inner lumen of the catheter and in preferred embodiments remains within the confines of the wall of the lumen as the fluid from the outer balloon flows through the side openings in the side wall of the lumen into pressure contact with the outer wall of the inner balloon.

This embodiment of FIGS. 50A-63B also includes an intermediate balloon forming an inner liner within the outer balloon, discussed in detail below, although in an alternate embodiment of the catheter of FIGS. 50A-63B, an intermediate balloon is not provided.

Catheter 600 has a retention balloon 604 identical to retention (stabilizing) balloon 206 of catheter 200 (or other stabilizing balloons disclosed herein), an inner balloon 608 and an outer balloon 606. An intermediate balloon 614 is positioned within the outer balloon 606 and external of the inner balloon 608.

Turning to FIGS. 56-58D, catheter 600 has four lumens: 1) lumen 644 in which inner balloon 608 is positioned (the inner balloon 608 forming the gas, e.g., air filled chamber); 2) lumen 642 communicating with intermediate balloon 614 via opening 642*a* for inflating the intermediate balloon 614 and thus expanding outer balloon 606; 3) lumen 640 communicating with the stabilizing balloon 604 to inflate stabilizing balloon 604; and 4) drainage lumen 646 having one or more side openings 610 at a distal end for drainage of the bladder. The side opening(s) is positioned between the outer balloon 606 and retention balloon 604, i.e., between the expanded portions of the balloons 606, 604. The lumen 644 is also sized to receive thermistor wires for temperature sensing.

Catheter 600 also has a hub portion with three angled extensions/ports (FIGS. 50A and 50C) at its proximal end: 1) port 620 for access via opening 623 to inflate the inner balloon 608; 2) port 622 for access via opening 625 to lumen 642 to inflate intermediate balloon 614; and 3) port 626 for access to lumen 640 via opening 629 to inflate stabilizing balloon 604 via opening 629. Drainage lumen 646 extends linearly terminating at proximal region 624 in opening 627. Thermistor wires (discussed below) can exit from the catheter port 620 for connection to a temperature monitor via hub 330 (discussed below). Note the location of the catheter angled ports can vary from that illustrated in FIG. 50A. Also, the location of the lumens and the cross-sectional dimension/size of the lumens can vary from that shown in FIGS. 58B-58D as these provide just one example of the location and size, e.g., diameter, of the lumens as well as one example of the shape/cross-sectional configuration and location.

Figure 50A:
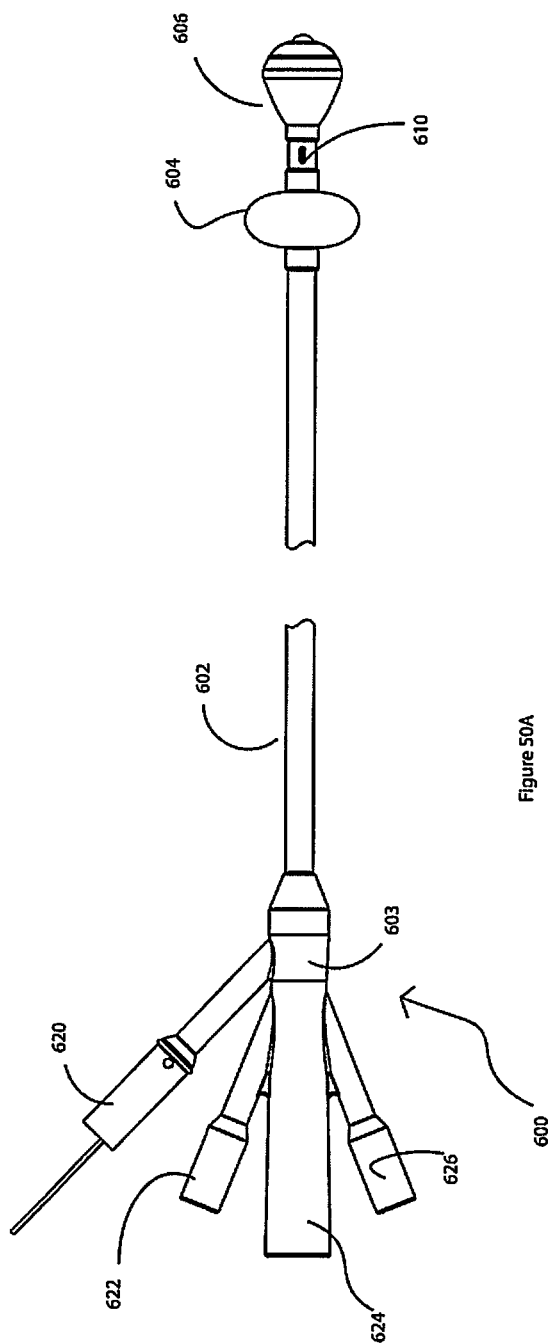
FIG. 50A is a side view of an alternate embodiment of the catheter of the present invention showing the balloons in the inflated condition.
Figure 50B:
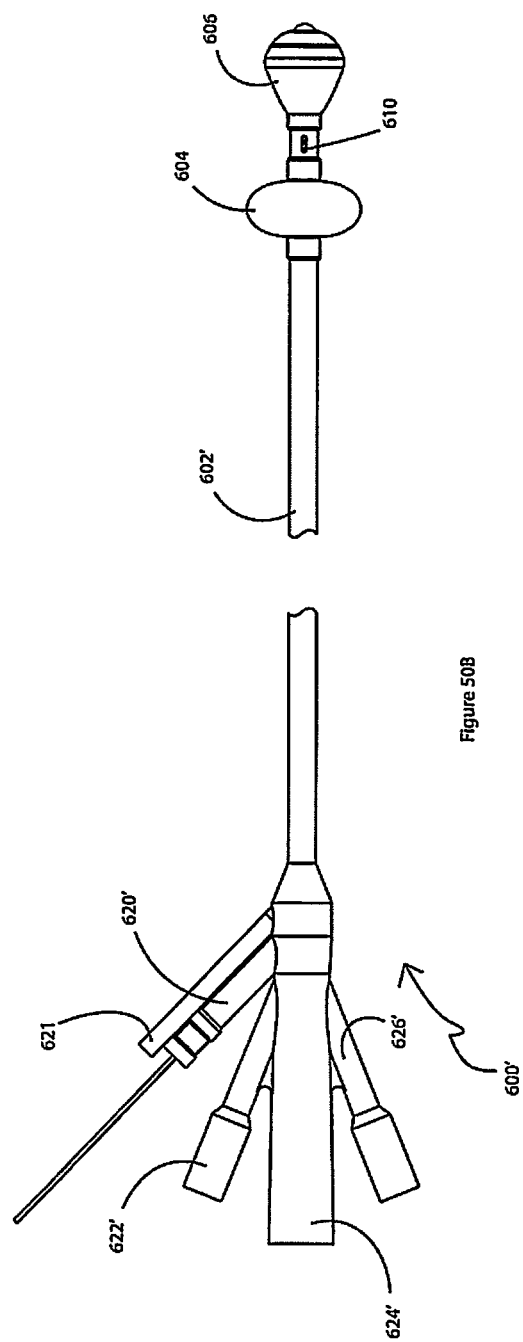
FIG. 50B is a side view of an alternate embodiment of the catheter of FIG. 50A having an additional port for the thermistor wires.
Figure 50C:
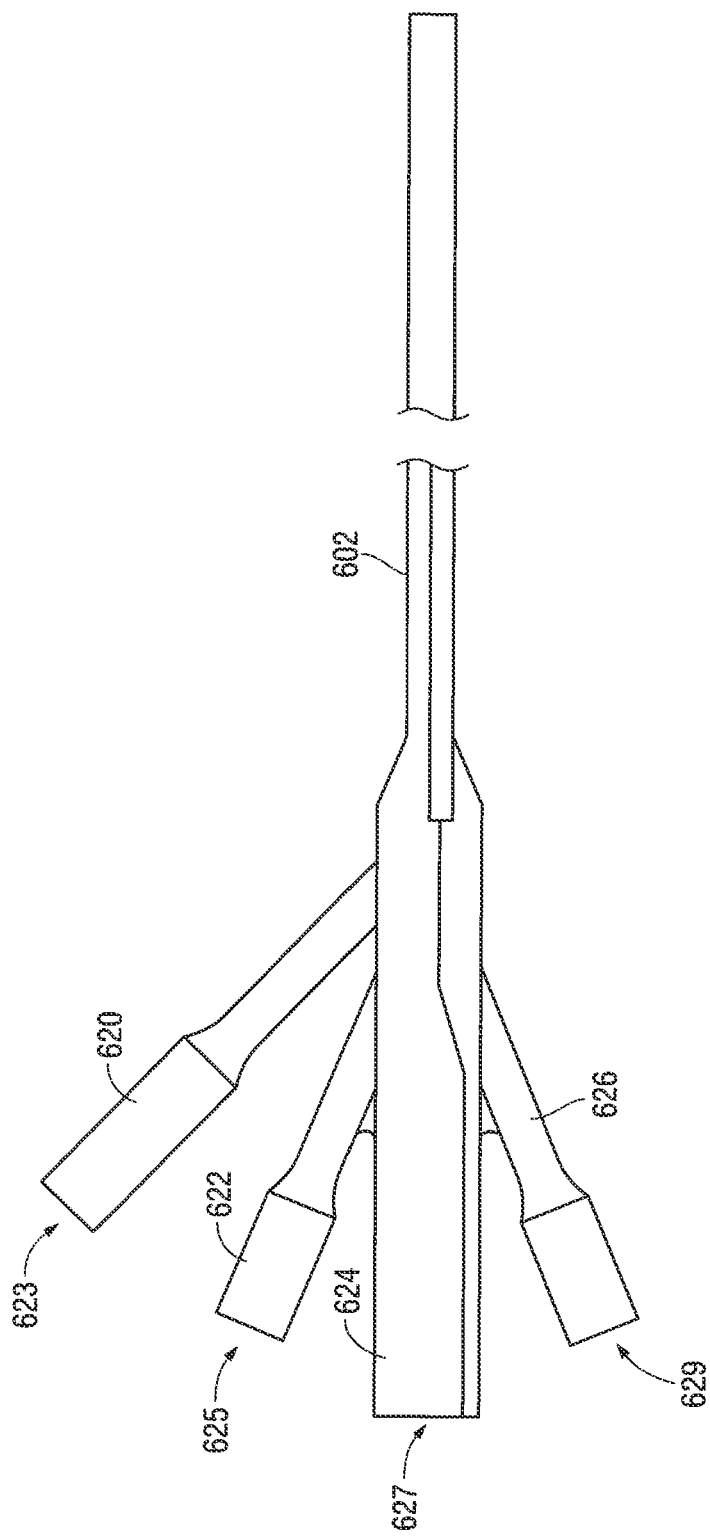
FIG. 50C is a side view of the proximal portion of the catheter of FIG. 50A.
Figure 51:
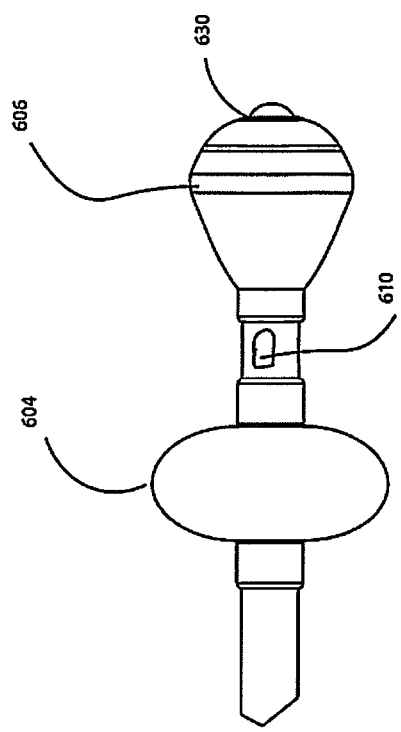
FIG. 51 is a close up view of the distal end of the catheter of FIG. 50A with the balloons in the inflated condition.
Figure 55:
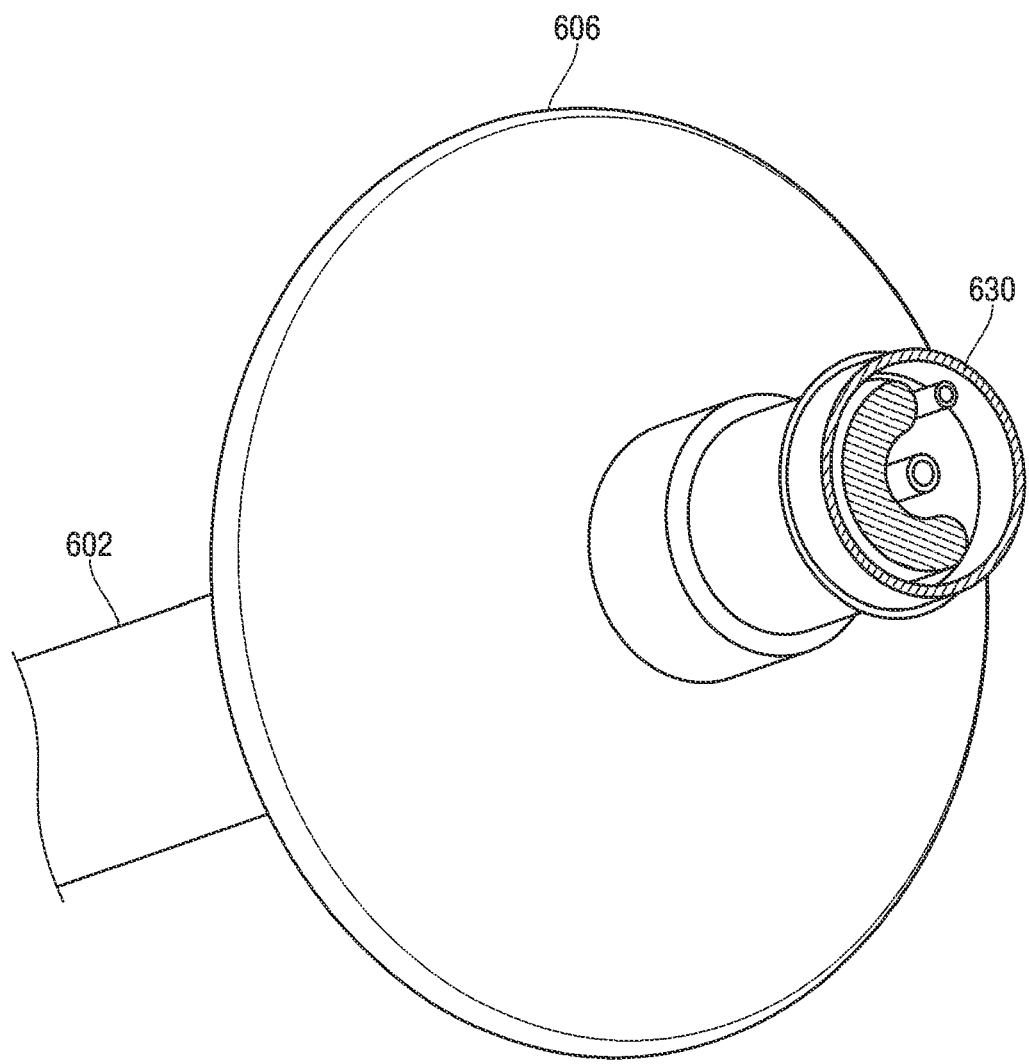
FIG. 55 is an enlarged view of the distal tip of the catheter of FIG. 50A.
Figure 59A:
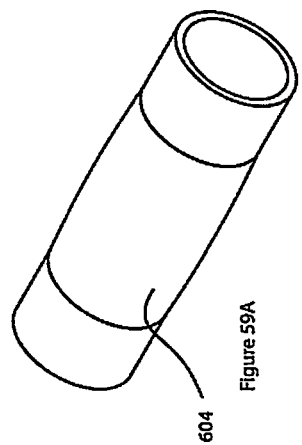
FIG. 59A is a perspective view of the retention balloon of the catheter of FIG. 50A.
Figure 59B:
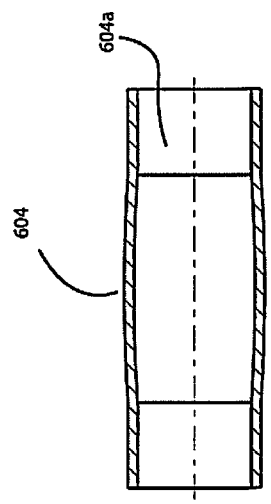
FIG. 59B is a cross-sectional view of the retention balloon of FIG. 59A.

In the alternate embodiment of FIG. 50B, catheter 600' is different from catheter 600 of FIG. 50A in that four angled ports are provided. Ports 626', 624' and 622' of catheter 600' are identical to ports 626, 624 and 622 of catheter 600 of FIG. 50A and therefore similar components are labeled with "prime" reference numerals. In this embodiment, an additional port 621 is provided for the thermistor wires as they do not extend through port 620' as they do in port 620 of FIG. 50A. Otherwise catheter 600' is identical to catheter 600, e.g., it has the retention, outer, intermediate and inner balloons. Note the thermistor wires extending through port 621 can extend through a separate lumen within catheter shaft 602', or alternatively, can extend through the same lumen as the lumen for the inner balloon, but separate at a proximal end to extend through port 621.

A thermistor can be placed adjacent the drainage opening 610 of catheter 600 for temperature readings, and the thermistor wire(s) can extend through a lumen of the catheter 600 such as lumen 644 for the inner balloon as in catheter 600 or alternatively through the drainage lumen or through a separate lumen, for electrical connection to a temperature monitor.

Catheter 600 has an inner drainage lumen 646 having a plug or seal 662 (FIG. 54) positioned therein which seals the drainage lumen 646 distal of the plug 662. A distal plug 630 is distal of the drainage side opening(s) 610 so as to not interfere with drainage of the bladder. The distal plug 630 also forms a cap at the distal end of the catheter 600 to provide a blunt tip.

Distal of plug 662 is a distal region or area 623 which forms an enlarged area of the lumen 644 which receives the inner balloon 608. Inner balloon 608 has a balloon region 608*a* and a tubular region 609 extending proximally therefrom. Tubular region 609 extends within lumen 644 which is separate (independent) from the drainage lumen 646. Thermistor wires discussed below can also extend through lumen 644. FIG. 54 shows the enlarged region 623 of lumen 644 which forms a chamber for the balloon 608. Preferably, there is a gap (space) between the outer wall of balloon 608 and the wall of the lumen forming the chamber. One or more openings 644*a* (FIGS. 56 and 58B) are provided within the catheter 600 at the distal region 623 for fluid communication from the intermediate balloon 614 through the opening(s) 644*a* and against the outer wall of the inner balloon 608 to deform the inner balloon 608. Thus, the openings 644*a* communicate with the chamber 623. The openings 644*a* can be oval shaped as in FIG. 56, or alternatively others shapes and sizes. In the illustrated embodiment, two openings are provided, however, additional openings can be provided. These openings provide a passageway for fluid, e.g., gas such as air or saline, from inside the inflated intermediate balloon 614 into contact with the outer wall of the inner balloon 608 to deform the inner balloon 608 to provide finer pressure measurements.

The inner balloon 608 has an elongated shape (FIGS. 54 and 60A) with tubular portion 609 extending proximally from the expanded larger diameter portion 608*a*. As noted herein, the elongated tubular portion 609 can extend along the length of the lumen 644 and through the side port 620, terminating at a proximal end in the catheter connector, and attached thereto, as discussed below. For example, the tubular portion 609 in some embodiments can have a length of about 600 mm and the expandable portion 608a can have a length of about 10 mm, although other dimensions are also contemplated. As discussed above, the tubular portion in alternate embodiments can terminate in the lumen distal of the connector. Inner balloon 608 has a distal extension 611 attached within opening 631a (FIG. 61B) in distal extension 631 of distal plug 630 via sealing material 632 (FIG. 54), such as silicone. A proximal plug 662 is positioned within the lumen 644, adjacent to but proximal of the expandable portion 608a of inner balloon 608 to attach the tubular portion 609 of balloon 608 within opening 644 via sealing material 634 such as silicone. Thus, distal and proximal plugs 630 and 662 securely retain the inner balloon 608 at different sides so it is maintained within the enlarged region 623 centered within the region. That is, in preferred embodiments, the inner balloon 608 is kept spaced from the wall of the distal region 623 so as not to interfere with flow through the openings 644a which could cause false pressure readings. Inner balloon 608 can be composed of a thermoplastic material, such as PET, which is impermeable to air and not water soluble, but has relative stiffness. Other materials are also contemplated such as EVA.

In an alternate embodiment, the inner balloon can include an inner component 639 placed within the inside diameter. The inner component 639 (FIG. 60D) is a bead-mandrel which is utilized to decrease the amount of air charge in the inner sensing balloon 608. Such inner component can increase the sensitivity of the sensor capabilities. That is, if there is less air in the inner balloon 608, the balloon is more responsive to changes in pressure. Thus, by eliminating dead space, it makes it more sensitive. The component 639 can extend the length of the balloon, i.e., starting at the proximal end of the tubular portion 609 and extending to the distal tip of balloon 608, or alternatively can extend only along a partial length of the inner balloon 608, e.g., extending only in a portion of the tubular portion 609 and/or the expanding portion 608. In some embodiments, the inner component 639 can have for example a length of about 19 to about 20 inches and an outer dimeter of about 0.02 inches, although other lengths and diameters are also contemplated. The inner component to decrease the amount of air in the system can be used with the other catheters disclosed herein.

Figure 60A:
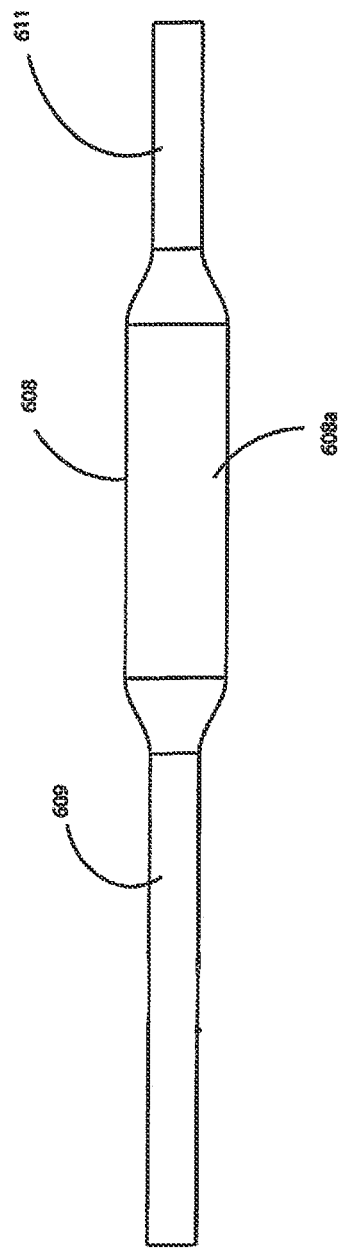
FIG. 60A is a side view of the inner balloon of the catheter of FIG. 50A.
Figure 60C:
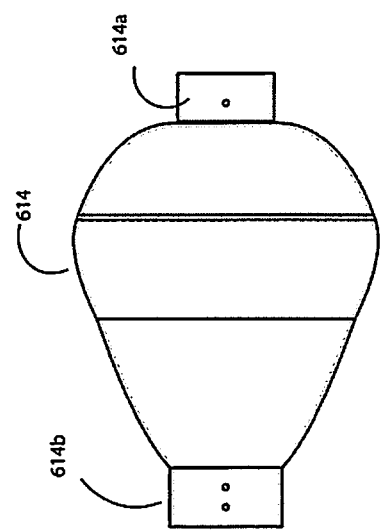
FIG. 60C is a side view of the intermediate balloon (inner liner) of the catheter of FIG. 50A.
Figure 61B:
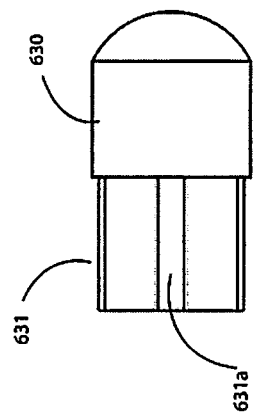
FIGS. 61A and 61B are side views of the distal tip of the catheter of FIG. 50A.
Figure 60B:
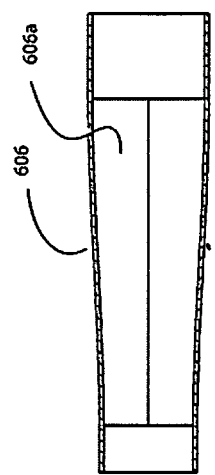
FIG. 60B is a side view of the distal outer balloon of the catheter of FIG. 50A.
Figure 61A:
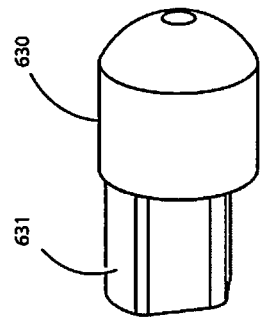
Figure 60D:
FIG. 60D is a side view of an insert for the inner balloon in accordance with an alternate embodiment.
Figure 63A:
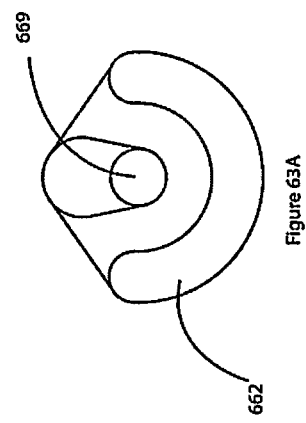
FIG. 63A is a front view of the proximal plug of the catheter of FIG. 50A.
Figure 63B:
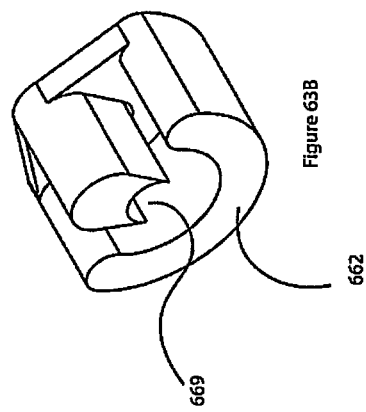
FIG. 63B is a perspective view of the proximal plug of FIG. 63A.
Figure 62:
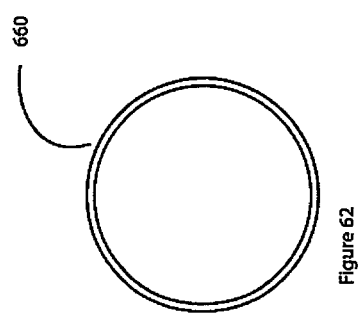
FIG. 62 is a front view of the distal inner sleeve of the catheter of FIG. 50A.
Figure 64:
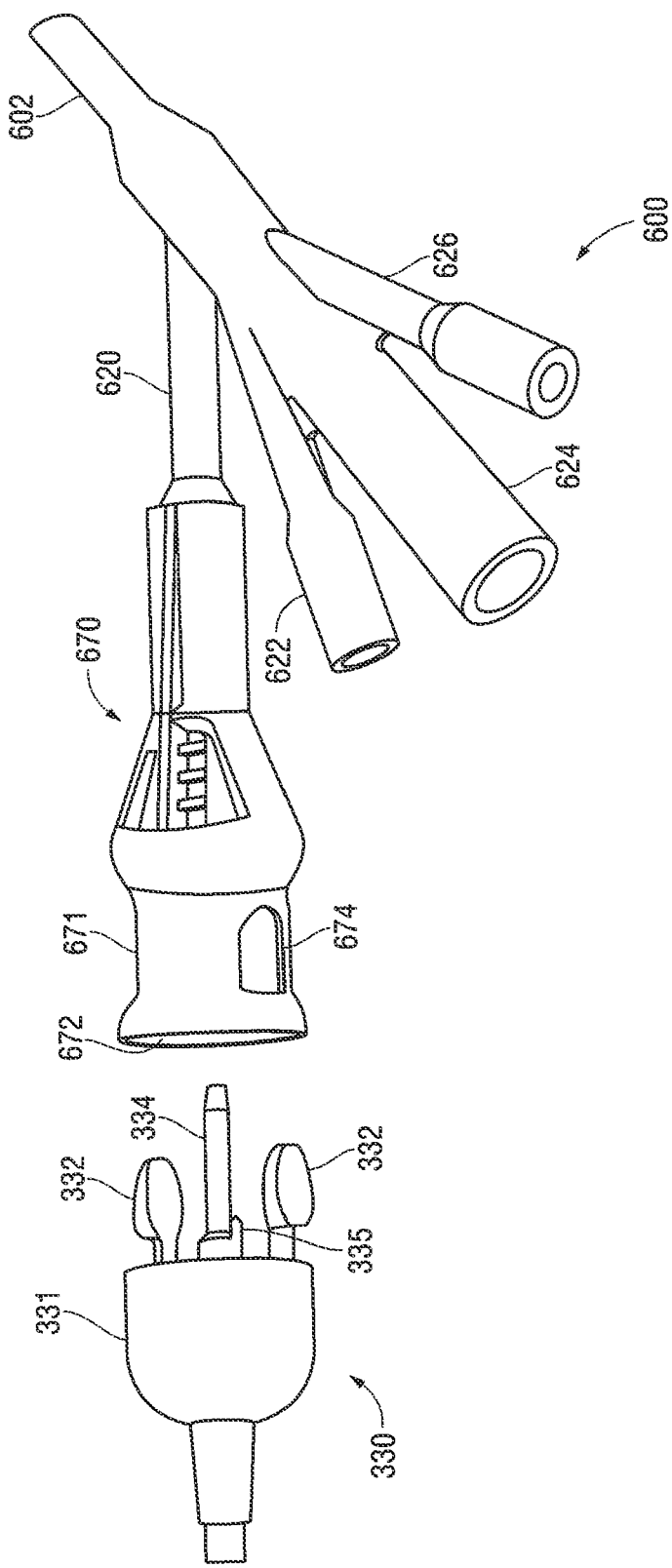
FIG. 64 is a perspective view of an alternate embodiment of the hub and connector of the present invention.
Figure 65:
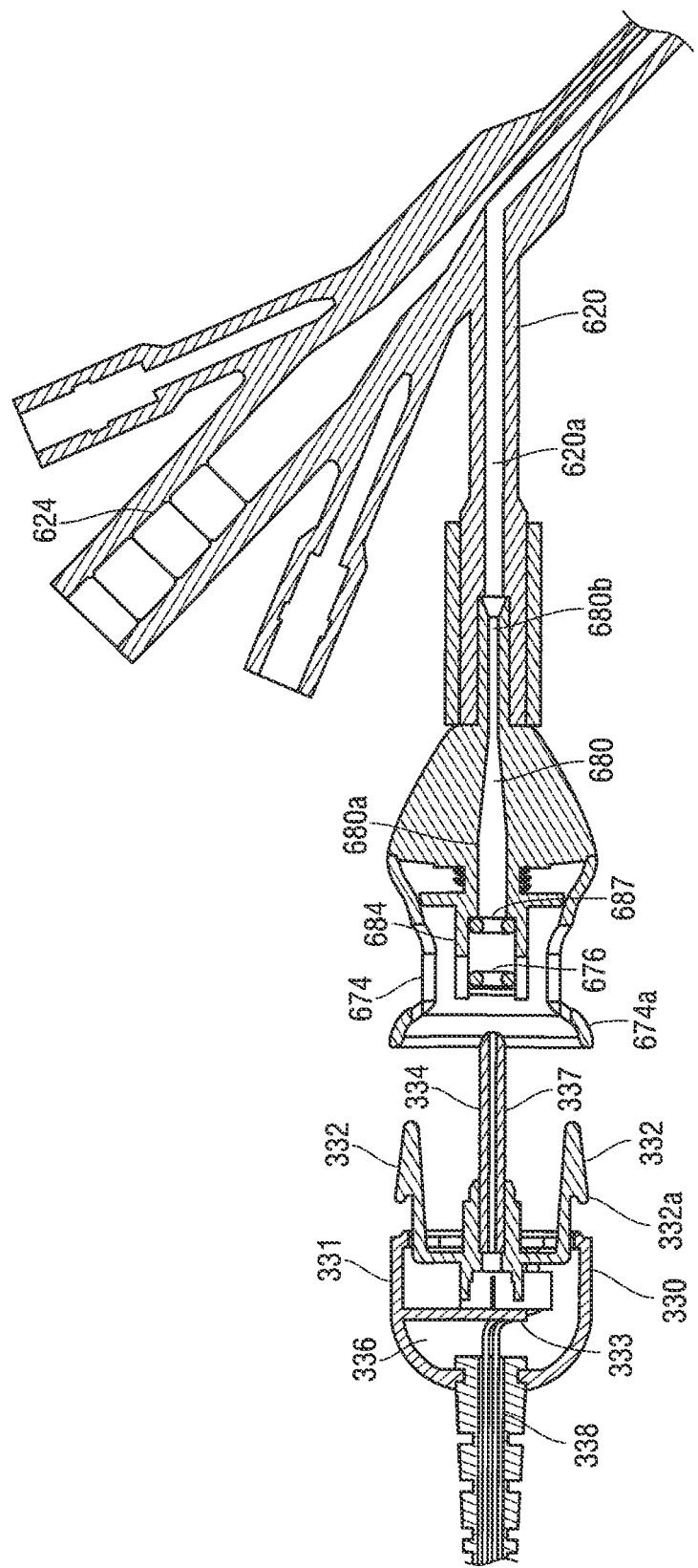
FIG. 65 is a cutaway side view of the hub and connector of FIG. 64.
Figure 66A:
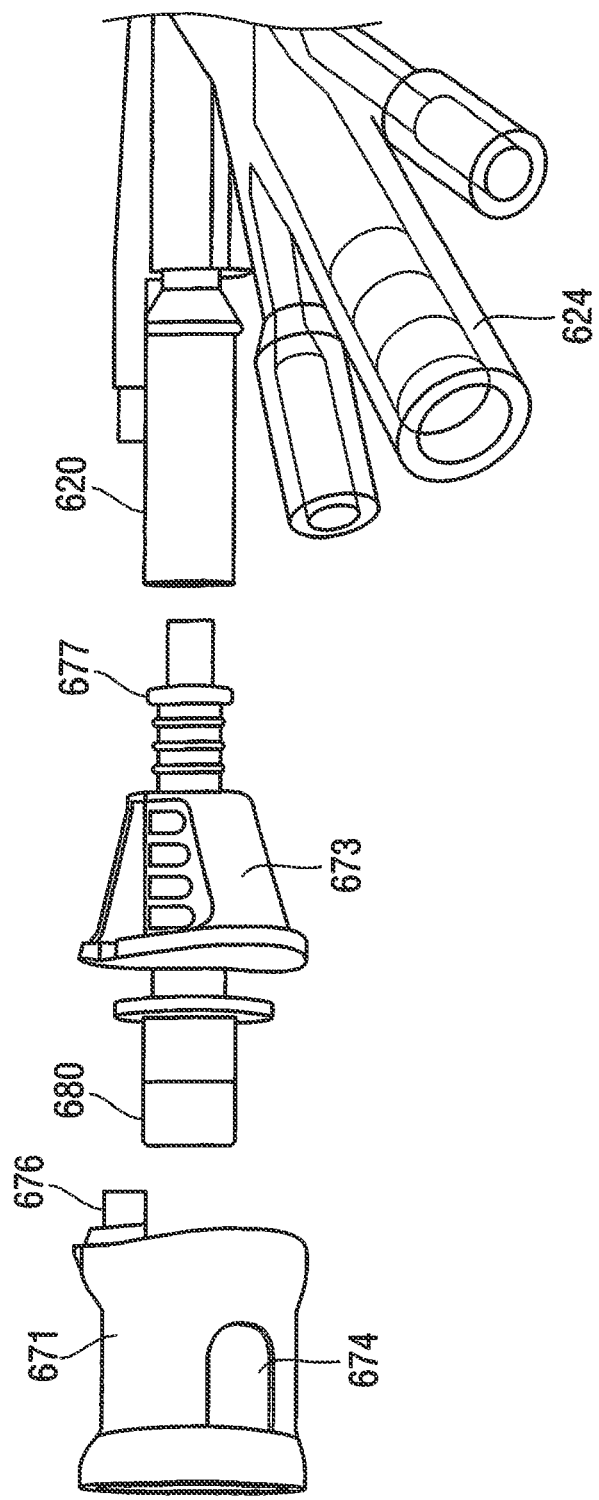
FIG. 66A is an exploded perspective view of a hub and connector of FIG. 64.
Figure 66B:
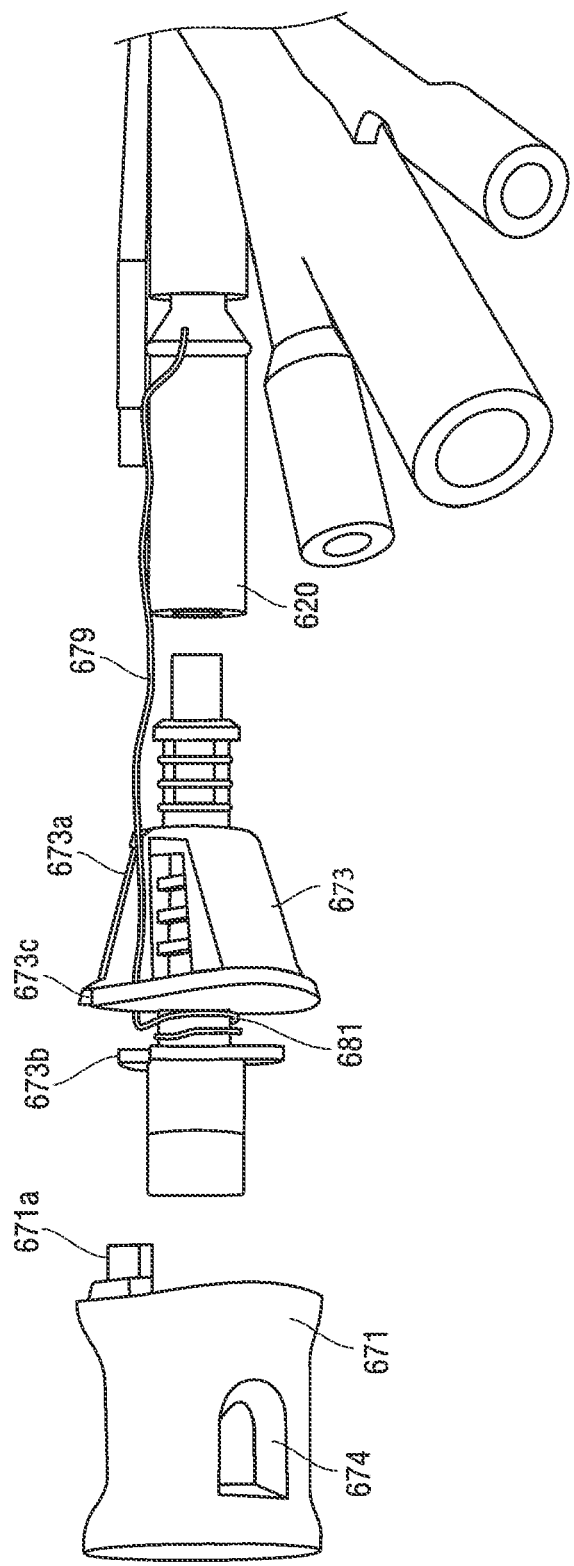
FIG. 66B is an exploded perspective view of the connector showing the thermistor wires.
Figure 67:
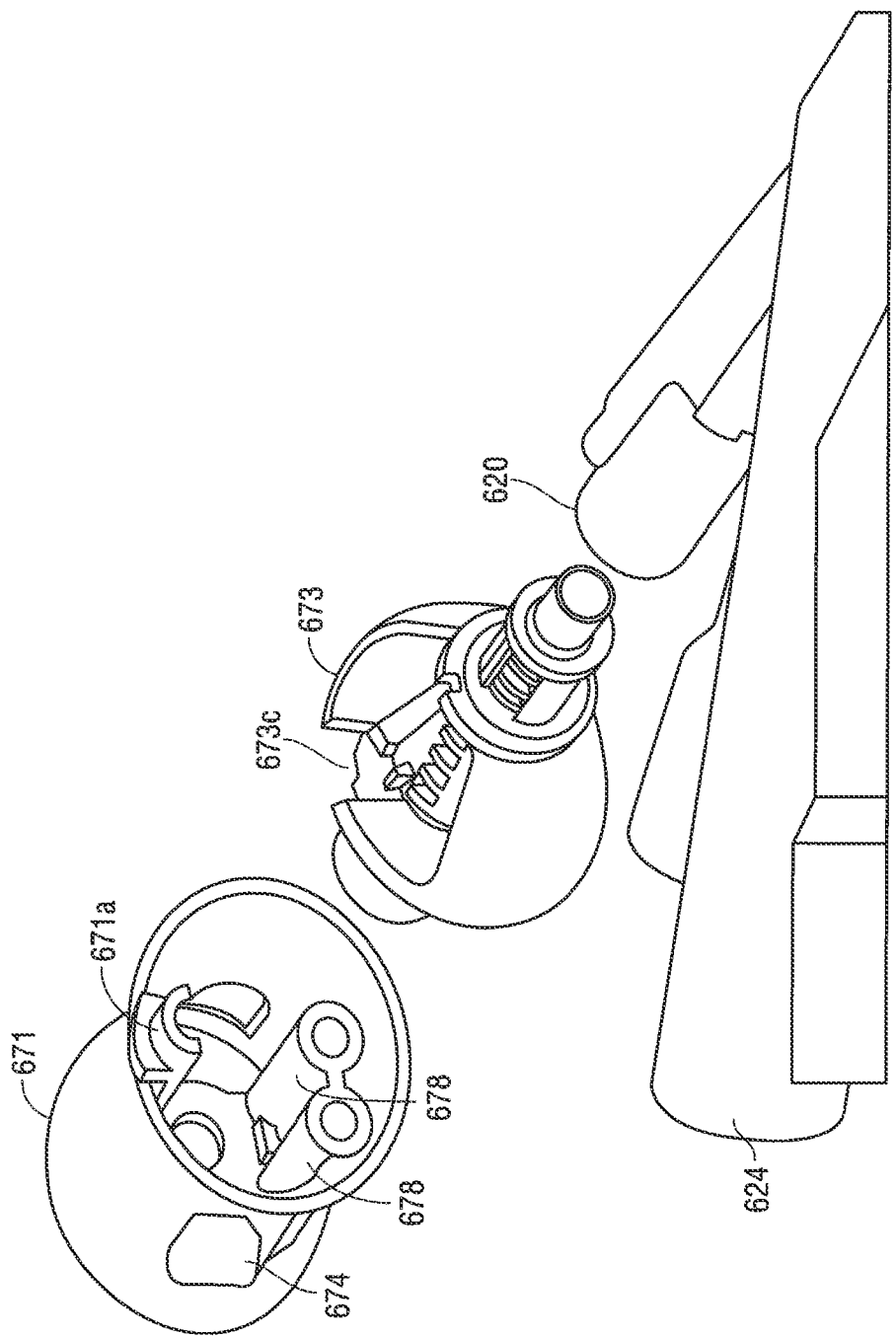
FIGS. 67 and 68 are exploded perspective views of the hub and connector of FIG. 64.
Figure 68:
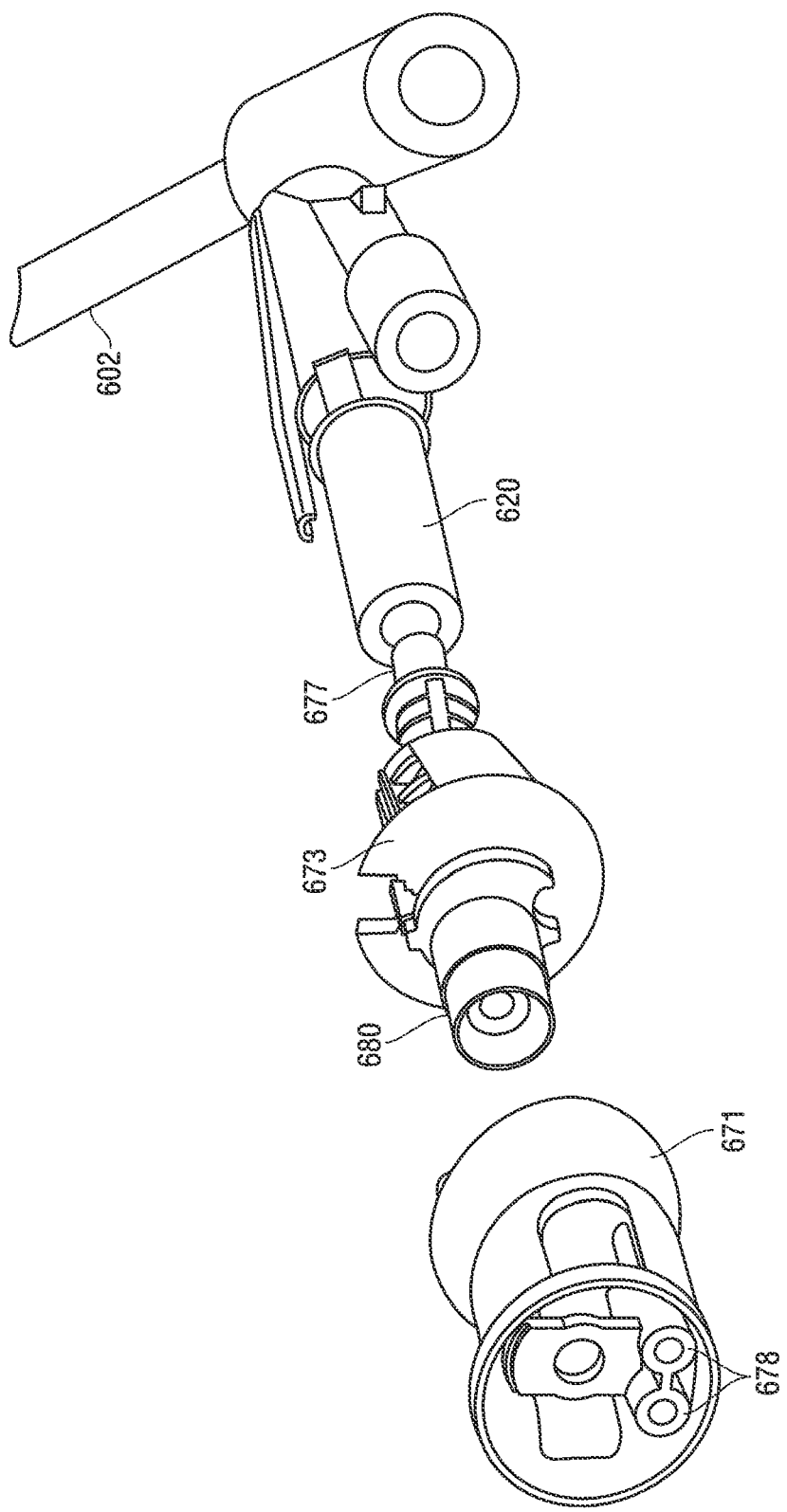
Figure 69:
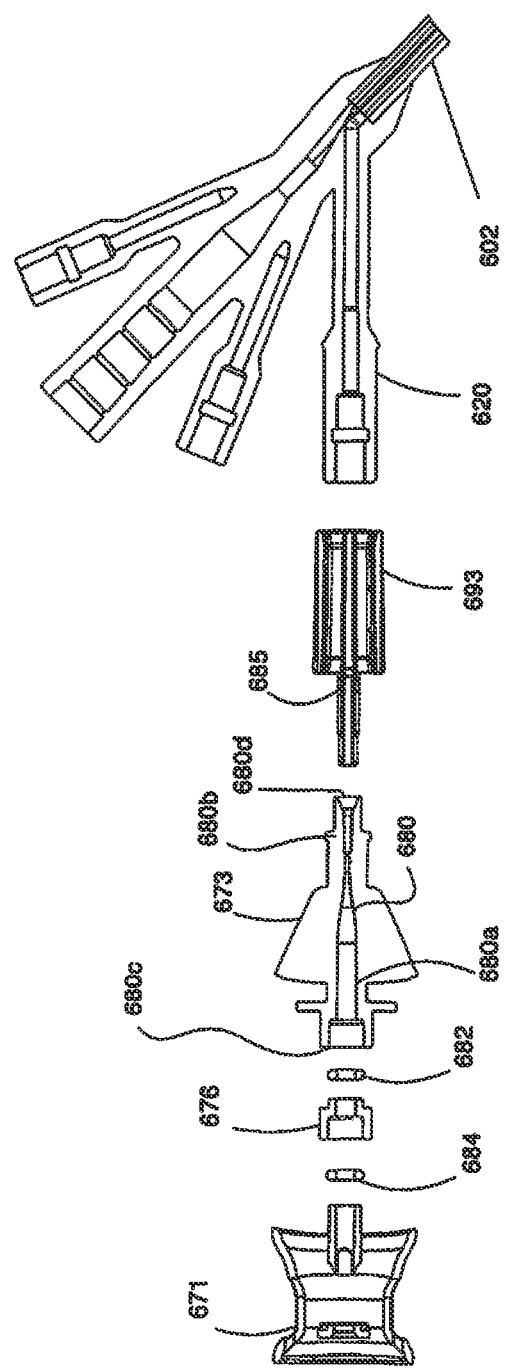
FIG. 69 is an exploded side view of the hub and connector of FIG. 64.

The intermediate balloon 614 can be "pear shaped" or "liberty bell shaped" as shown in FIGS. 54 and 60C. Proximal extension 614b is attached to an outer surface of catheter 600 at region 617 and distal extension 614a is attached to an outer surface of catheter 600 at region 619. The intermediate balloon 614 is positioned within outer balloon 606. In the embodiment of FIG. 54, the intermediate balloon 614 is shaped to form a gap 615 at a distal region between the outer wall of the balloon 614 and inner wall of the outer balloon 606, however, in alternate embodiments, the intermediate balloon 614 could more closely follow the full contour of the outer balloon 606 so that no gap or a smaller gap would be provided. The distal end of the outer balloon 606 can wrap underneath the end of the intermediate balloon 614 for attachment to the catheter outer surface as shown in FIG. 54, with a distal sleeve 660 positioned over the two ends of the balloons. Alternatively, the outer balloon distal end can remain atop the intermediate balloon distal end in the same manner it does at the proximal attachment at region 617 shown in FIG. 54. In alternate embodiments, the intermediate balloon 614 can also wrap in the same manner as the outer balloon 606 of FIG. 54. In an alternate embodiment, the outer balloon 606 can have one side larger so it inverts on itself such that it would not stick out of the distal end of the catheter shaft.

The intermediate balloon 614 forms an inner liner of the outer balloon 606 to therefore act a like a coating to stiffen the outer balloon 606. The intermediate balloon 614 is composed of a material, e.g., a thermoplastic material, that is less compliant than the outer balloon 606. For example, the intermediate balloon 614 can be composed of EVA which would counteract expansion of the more compliant outer balloon 606. The outer balloon 606 is composed of a more compliant material such as silicone. With a compliant balloon, it would continue to expand (stretch) so the pressure would drop. The inner liner prevents this. Note that outer balloon 606 preferably has a smoother surface to shield the thermoplastic intermediate balloon 614 during insertion and use to reduce patient discomfort. The intermediate balloon 614 in some embodiments has a wall thickness less than the wall thickness of the outer balloon 606. Note that other compliant/non-compliant materials are also contemplated.

In an alternate embodiment, upon inflation of the intermediate balloon 614, the outer balloon 606 would peel back. Therefore, the outer balloon 606 would act as a sheath.

In use, the intermediate balloon 614 is expanded via injection of fluid, e.g. air saline, etc. through the port 622. Expansion of the intermediate balloon 614 causes expansion of the outer balloon 606. Deformation of the outer balloon 606 based on changes in pressure within the patient, e.g., within the bladder in response to abdominal pressure, causes deformation of the intermediate balloon 614. As the intermediate balloon 614 is deformed, fluid within the intermediate balloon 614 passes through the opening(s) 644a within the catheter to apply a pressure against the outer wall of the inner balloon 606 to deform the inner balloon 606 to provide pressure readings in the same manner as the other embodiments disclosed herein.

Figure 26:
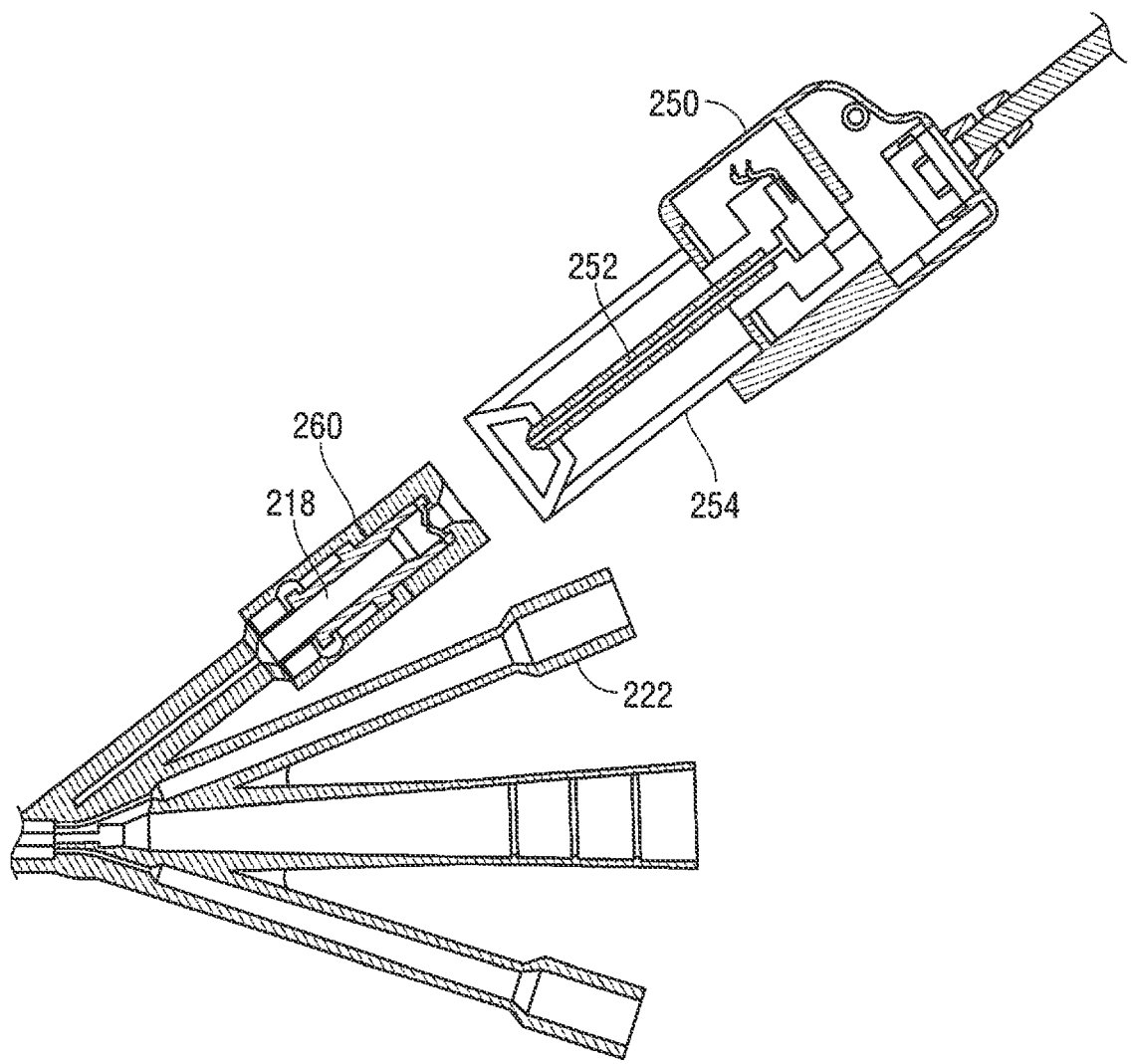
FIG. 26 is a side view of alternate embodiment of the pressure transducer hub having a shroud over the elongated member for snap fitting onto the catheter.

Turning back to the transducer hubs mountable to the catheter, FIG. 26 illustrates an alternate embodiment of the pressure transducer hub. In this embodiment, hub 250 has a shroud 254 (shown schematically) positioned over elongated member 252. This helps protect/shield the elongated member 252. When the transducer 240 is mounted to the port 260 of the catheter, the shroud 254 fits over cover 260 of port 218 and is retained by a snap fit or by other methods of securement.

Figure 27:
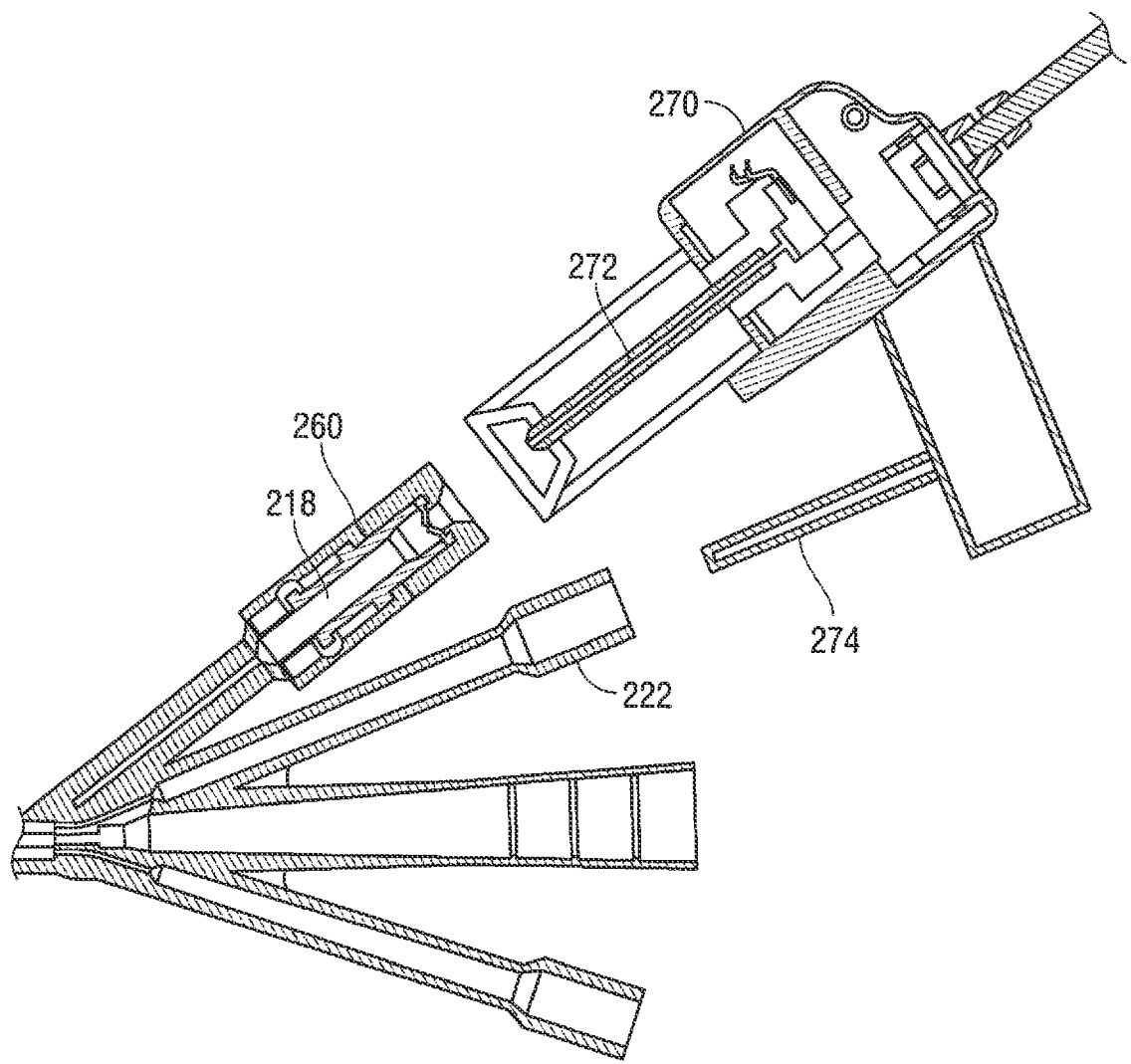
FIG. 27 is a schematic view of an alternate embodiment of the pressure transducer hub extendable into two side ports of the catheter.

In the aforedescribed embodiments, mounting of the transducer hub a) automatically connects the temperature sensor to a connector for communication with a temperature monitor cable; and b) automatically advances air through the first lumen to expand the inner balloon. In the embodiment of FIG. 27, the pressure transducer hub 270 has a second elongated member 274 extending therefrom. When transducer hub 270 is mounted to the catheter, e.g., port 218, elongated member 272 enters the air lumen in the same manner as elongated member 242 of FIG. 24A. Additionally, elongated member 274 automatically enters the lumen 210 at port 222 which communicates with the outer balloon 202. Therefore, in this embodiment, mounting of the transducer hub 270 a) automatically connects the temperature sensor to a connector for communication with temperature monitor cable as in the embodiment of FIGS. 18-25B; b) automatically advances air through the first lumen to expand the inner balloon as in the embodiment of FIGS. 18-25B; and c) automatically advances air through lumen 210 communicating with the outer balloon 202 to inflate (expand) the outer balloon 202. The catheter of FIG. 27 (and FIG. 26) is otherwise identical to catheter 200 of FIG. 18A so for brevity further discussion is not provided since the description of the function and elements of catheter 200 are fully applicable to the catheter of FIG. 27 (and to the catheter of FIG. 26).

FIGS. 28A-28D show an alternate embodiment of the hub/connector. The pressure transducer is external to catheter 280 and mounted to port 282 at the proximal end 281 of catheter 280 via connector (housing) 290. Catheter 280 is identical to catheter 200 of FIG. 18A except for the connector and transducer hub temperature sensor connection.

Figure 28A:
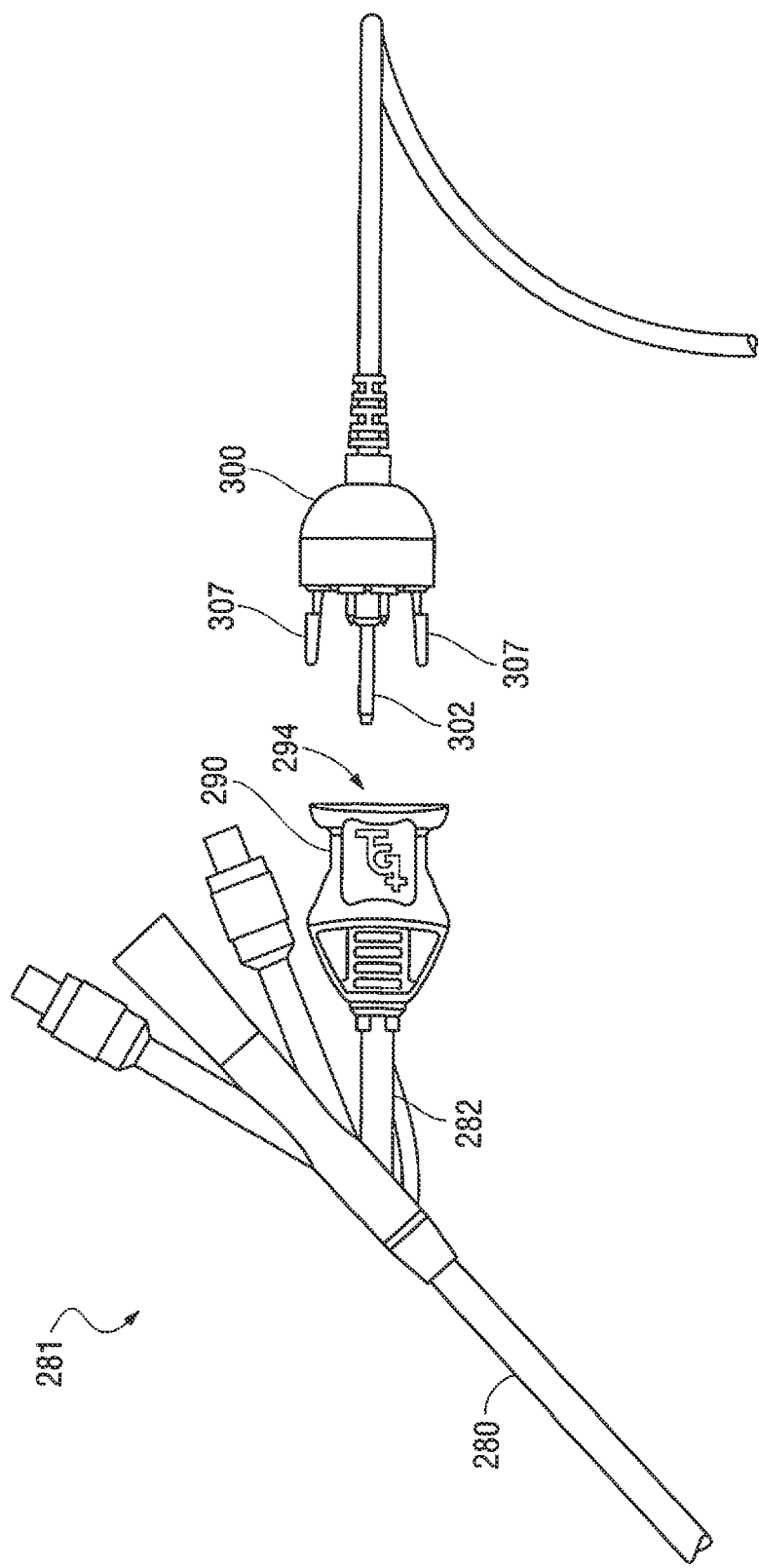
FIG. 28A is a perspective view of an alternate embodiment of the transducer hub and connector.
Figure 28B:
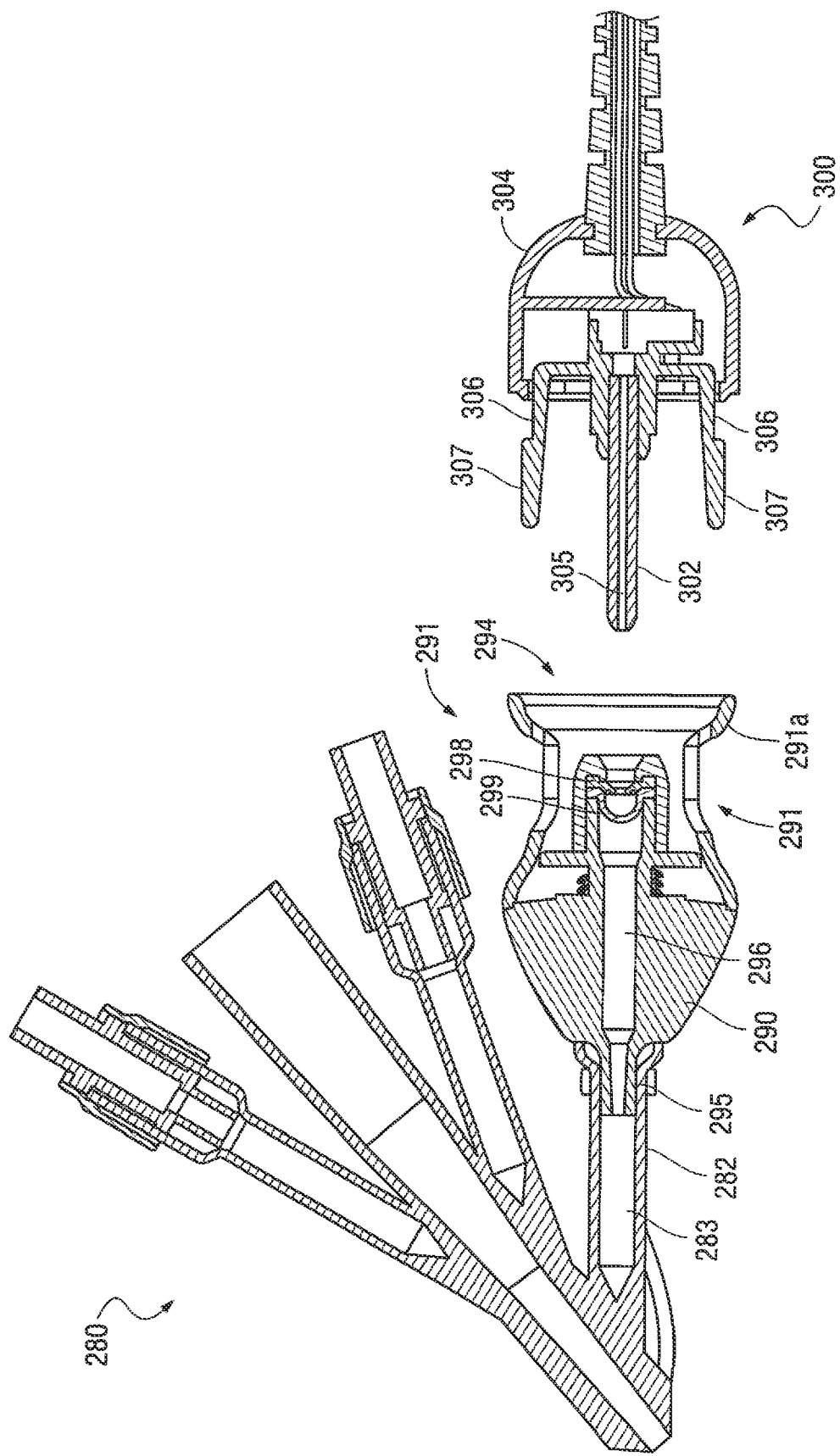
FIG. 28B is a cutaway side view of the hub and connector of FIG. 28A showing the pressure transducer prior to connection to the catheter of FIG. 18A, a portion of the hub wall and connector removed to show internal components.
Figure 28C:
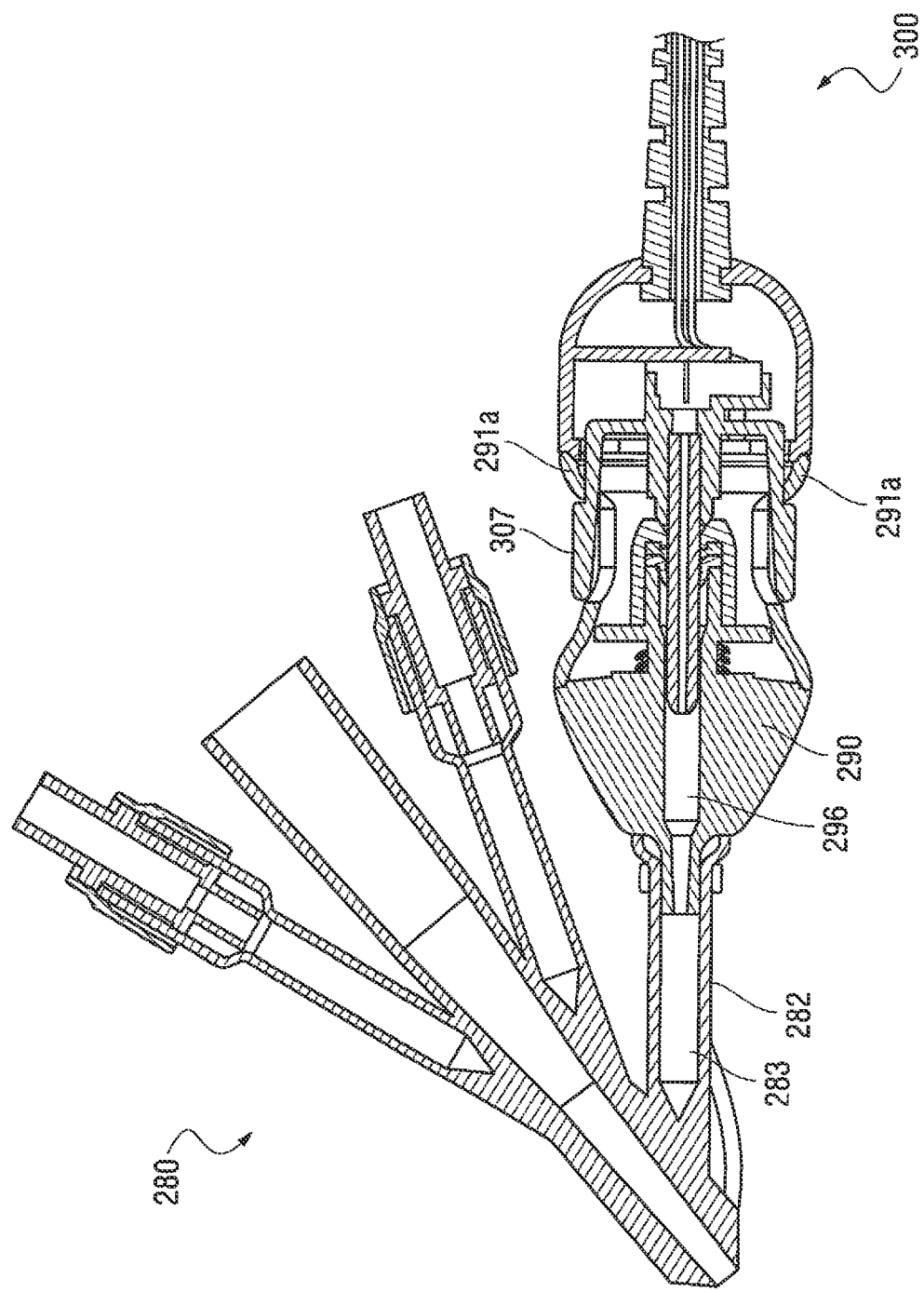
FIG. 28C is a cutaway side view similar to FIG. 28B showing the hub attached to the catheter.

More specifically, transducer hub or housing, designated generally by reference numeral 300, contains the pressure transducer and sensor 309 and is mounted to the angled side port 282. In the embodiment of FIG. 28A, the hub 300 is mounted to the catheter 280 by connection to housing 290. Housing 290 is connected to port 282 via a barbed fitting 295 providing an interference fit with the port 282. The hub 300 is locked or secured to connector 290 such as by a snap fit provided by the latch arms discussed below, although other attachments are also contemplated such as a friction fit, threaded attachment, other form of latch, etc., as well as other types of snap fits to provide an attachment that maintains an airtight seal so the air is contained within the air lumen and balloon 202 of the catheter 280. (As noted above catheter 280 is identical to catheter 200 except for its connector so catheter 280 includes (not shown) the inner and outer pressure balloons, stabilizing balloon, temperature sensor, etc. The catheter 280 can also have a single pressure balloon as in the aforementioned embodiments.

The housing 290 attached to catheter 280 has a proximal opening 294 and a channel (lumen) 296 to receive an elongated (rod-like) member or nose 302 extending distally from transducer hub 300. As shown channel 296 has a first diameter region 296a to match with the lumen 283 of the port 282, a second larger diameter region 296b proximal of region 296a to receive the male rod 302 of the hub 300, and a still larger diameter region 296c proximal of region 296b to receive the valve 299 and valve 298 and allow expansion thereof. As shown, valve 298 is dome shaped and is distal of valve 299. Conical cap 293, proximal of valve 299, provides a lead in to the valve 299 for the rod 302. Thermistor pins 292 receive thermistor connectors 308. Note valves 288, 299 are one example of valves that can be provided as other valves to provide an airtight seal are also contemplated. A single valve is also contemplated.

Hub 300 is mounted to connector 290 and includes a housing 304 from which a pair of distally extending snap fit connector arms 306 extend. The latch arms 306 are sufficiently flexible to enable attachment and have an enlarged distal portion 307, illustratively shown as arrow shaped although other enlarged shapes could be provided. The elongated member 302 extends between the latch arms 306. When the hub 300 is mounted to the connector 290, the elongated member 302 extends into the channel 296 to advance air to inflate the inner balloon. The enlarged ends 307 of latch arms 306 enter recesses 291 and engage shoulders 291a to retain the hub 300. Note to release (disconnect) the hub 300, the ends 307 are pressed radially inwardly to disengage from shoulder 291a and the hub 300 is pulled proximally. Note that alternatively a different number of latch arms could be provided.

The housing (connector) 290 has a lumen 296 for communication with the lumen 283 in the side port 282 of catheter 280 which communicates with the air lumen and inner balloon of the catheter 280. As noted above, the lumen 296 is dimensioned to receive the elongated rod 302 of transducer hub 300. The wire for the sensor extends in housing 300. When transducer hub 300 is attached to connector 290, such attachment inserts the elongated rod 302 into lumen 296 to advance air though the air lumen in the catheter and into the balloon 204. (Note the air lumen extends into its angled side port 282). The elongated member 302 also has a channel or lumen 305 extending therethrough to allow the pressure wave to travel through to the pressure sensor. Although in preferred embodiments no additional air needs to be injected into balloon 204 after attachment of hub 300, it is also contemplated that a port or opening can be provided in hub 300 to receive an injection device for injection of additional air. Such additional air can communicate with and flow through channel 305 of elongated member 302, into the air lumen and balloon 204 for inflation, or alternatively, a side port or opening in the angled port downstream (distal) of the elongated member 302 could be provided. Attachment of hub 300 to housing 290 also automatically connects thermistor connectors 308 to thermistor pins 292 to automatically connect the temperature sensor to the hub 300 for communication via a cable to a temperature monitor.

To charge the system, when the hub 300 is mounted to the side port 282 via attachment to connector 290, the elongated member 302 extends into lumen 296 to advance air through the air lumen into balloon 204 (or the pressure balloon in the embodiments with a single pressure balloon) to expand the balloon 204. That is, connection of the transducer hub 300 to the catheter 280 (port 282) automatically advances air through the connector lumen 296, the port lumen 283 and the first lumen 214 to expand the balloon 204. (Such connection also automatically connects the temperature sensor to the hub 300). In some embodiments, 0.2 cc of air can be displaced/advanced by the member 102, although other volumes are also contemplated. Thus, as can be appreciated, mounting of the hub 300 to the catheter 280 automatically pressurizes the air lumen/chamber and expands the balloon. Note the balloon can be partially or fully inflated (expanded), dependent on the amount of air advanced into the balloon. Further note that preferably the lumen is not vented to atmosphere when the transducer hub 300 is attached and air is advanced through the air lumen. The port 282 includes a closable seal, e.g., valves 298 and 299, through which the elongated member 302 is inserted but maintains the seal when the elongated member 302 remains in the lumen 296. Note that catheter 280 is identical in all other respects to catheter 200 so that the description of catheter 200 and its components and function (and alternatives) are fully applicable to catheter 280, the difference being the connector 290 of catheter 292 to receive transducer hub 300. The transducer hub is also different, e.g., has latch arms and a different configuration.

Figure 29A:
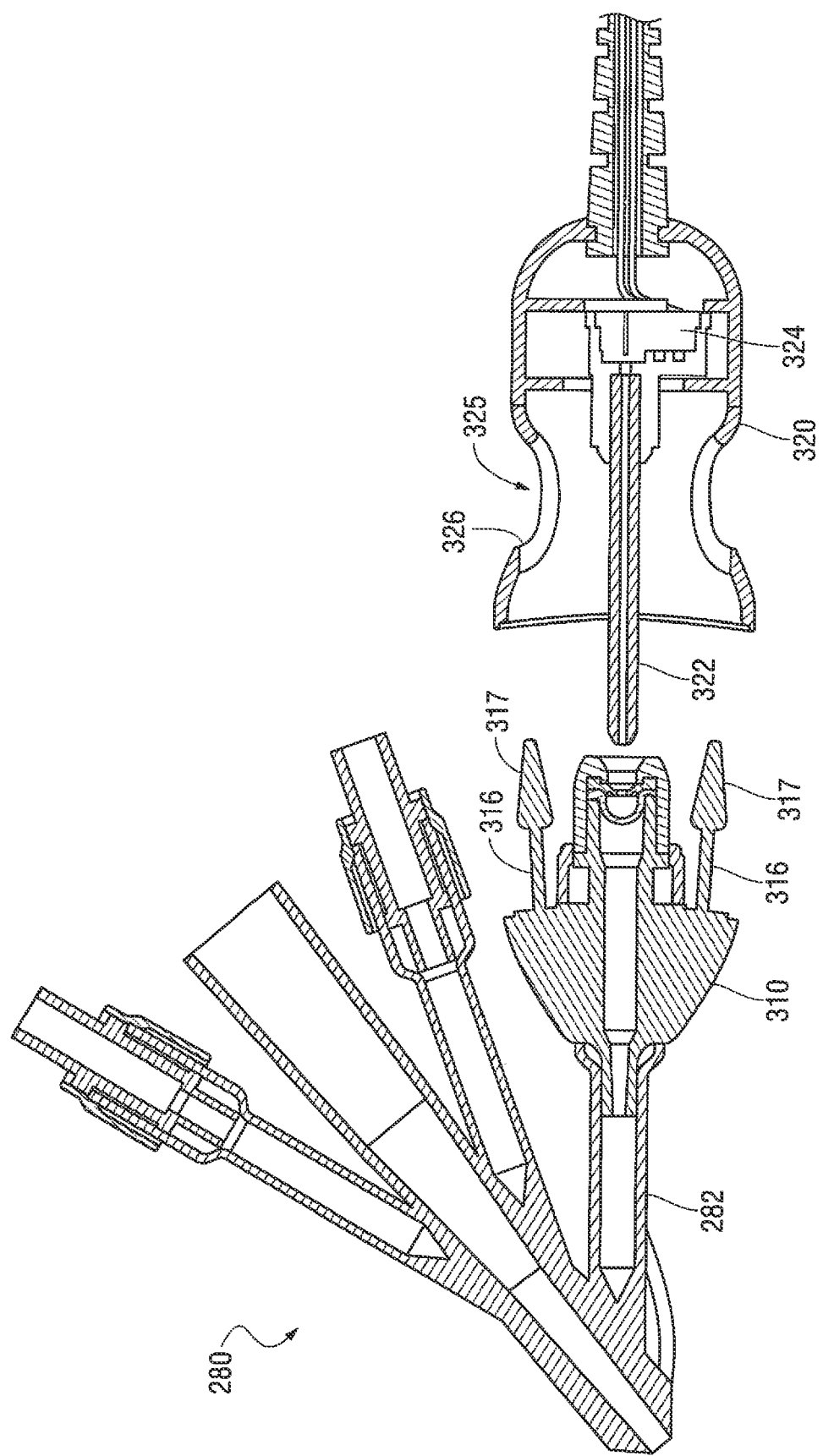
FIG. 29A is a cutaway side view of the hub and connector of an alternate embodiment showing the pressure transducer prior to connection to the catheter of FIG. 18A, a portion of the hub wall and catheter connector removed to show internal components
Figure 29B:
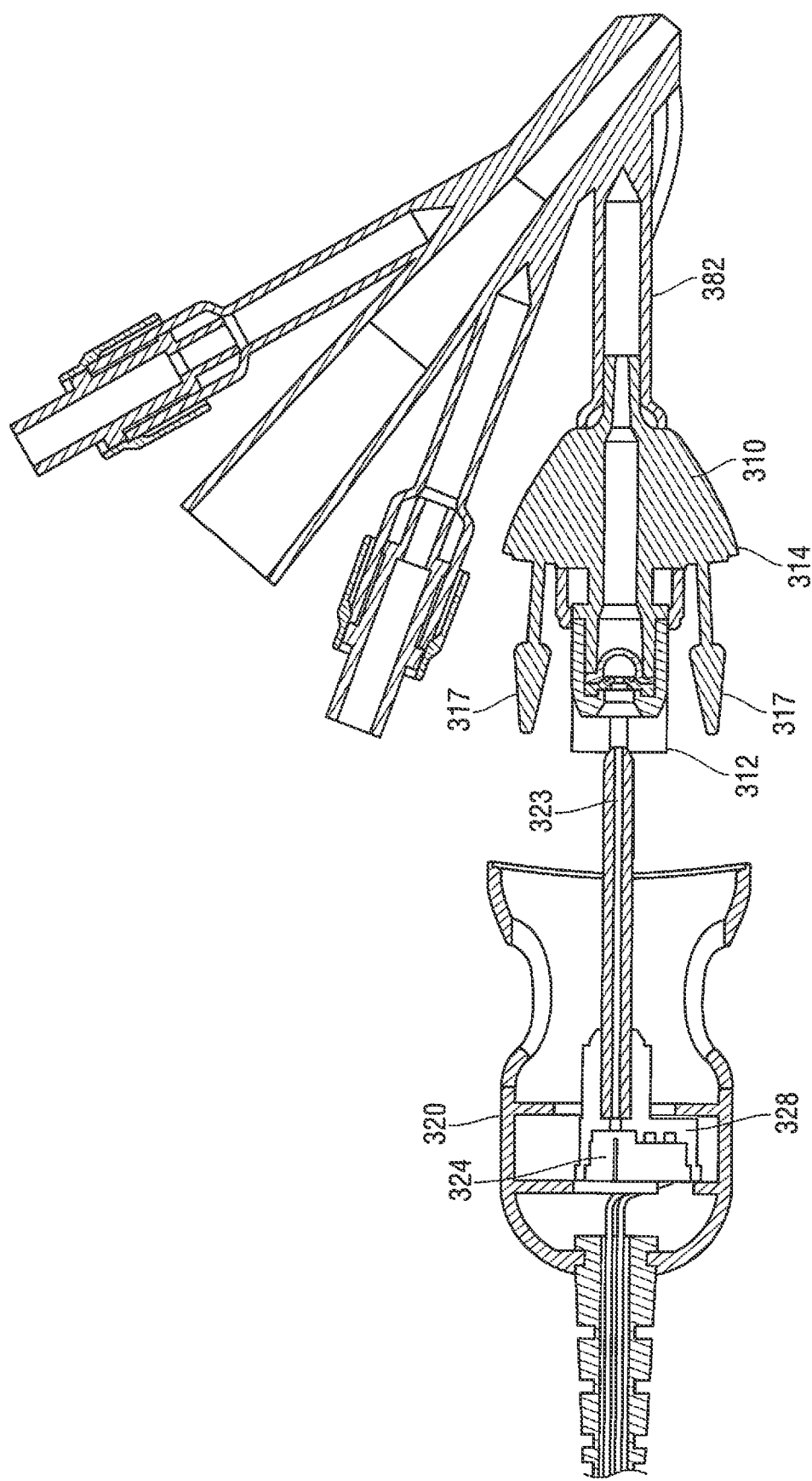
FIG. 29B is a cutaway side view of the hub and connector of FIG. 29A.
Figure 29C:
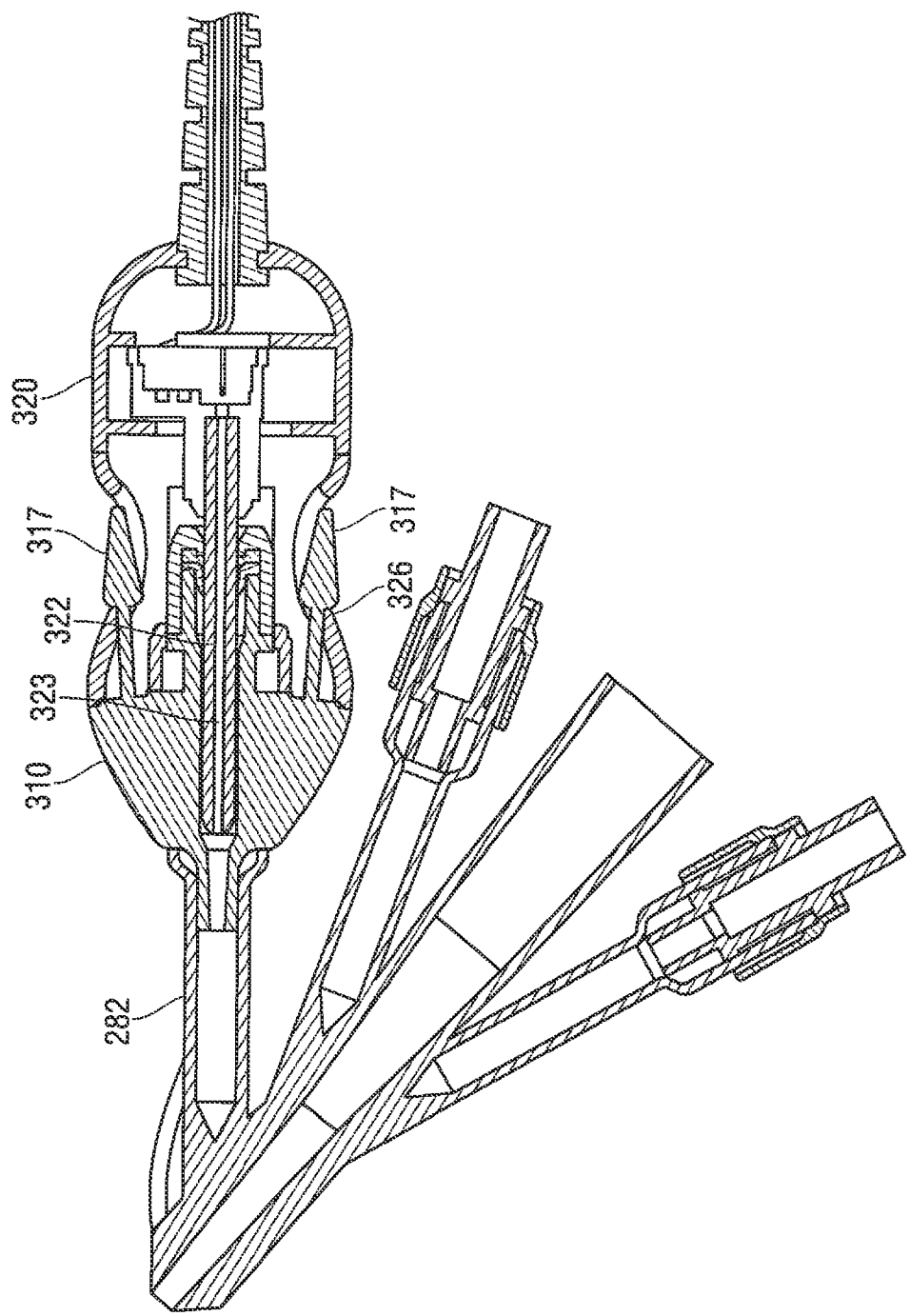
FIG. 29C is a cutaway view similar to FIG. 29B showing the hub attached to the connector of FIG. 29A when attached.

In the alternative embodiment of FIGS. 29A-29C, the latch arms are reversed so that they are located on the connector rather than on the transducer hub as in FIG. 28A. More specifically, transducer hub (housing), designated by reference numeral 320, has an elongated member 322 with a channel 323 and is identical to elongated member 302 of FIG. 28A for advancing air through the lumen and into the pressure balloon. Pressure transducer 324 is contained within the housing 320. Recesses 325 are dimensioned to receive the latch arms 317 of the connector or housing 310 which is connected to the side port 282 of catheter 280. (Catheter 280 is the same as catheter 280 of FIG. 28A except for connector 310). Extending proximally from housing 310 are two latch arms 16 with enlarged region 317 which engage the shoulders 326 formed by recesses 325 in hub 320 in a similar manner as latch arms 306 of FIG. 28A engage in recesses 291 and shoulder 291a. Connectors 328 in hub 320 engage thermistor pins 312 of connector 310 for connection of the temperature sensor. Connection of the hub 320, like hub 300, automatically advances air to inflate the pressure balloon and automatically connects the temperature sensor.

To disconnect (release) the hub 320, ends 317 of latch arms 316 are pressed radially inwardly to disengage from shoulder 326 so hub 320 can be pulled proximally out of connector 310.

In the alternative embodiment of FIGS. 29A-29C, the latch arms are reversed so that they are located on the connector rather than on the transducer hub as in FIG. 28A. More specifically, transducer hub (housing), designated by reference numeral 320, has an elongated member 322 with a channel 323 and is identical to elongated member 302 of FIG. 28A for advancing air through the lumen and into the pressure balloon. Pressure transducer 324 is contained within the housing 320. Recesses 325 are dimensioned to receive the latch arms 317 of the connector or housing 310 which is connected to the side port 282 of catheter 280. (Catheter 280 is the same as catheter 280 of FIG. 28A except for connector 310). Extending proximally from housing 310 are two latch arms 16 with enlarged region 317 which engage the shoulders 326 formed by recesses 325 in hub 320 in a similar manner as latch arms 306 of FIG. 28A engage in recesses 291 and shoulder 291a. Connectors 328 in hub 320 engage thermistor pins 312 of connector 310 for connection of the temperature sensor. Connection of the hub 320, like hub 300, automatically advances air to inflate the pressure balloon and automatically connects the temperature sensor.

To disconnect (release) the hub 320, ends 317 of latch arms 316 are pressed radially inwardly to disengage from shoulder 326 so hub 320 can be pulled proximally out of connector 310.

In the alternate embodiment of FIGS. 64-69, the transducer hub or housing, designated generally by reference numeral 330, contains the sensor (pressure transducer) and is mounted to the angled side port 620 of catheter 600. The hub 330 is mounted to the catheter 600 by connection to housing (connector) 670. Housing 670 is connected to port 620 via a barbed fitting 677 (FIG. 66A) providing an interference fit within the port 620. The hub 330 is locked or secured to connector 670 such as by a snap fit provided by the latch arms 332 discussed below, although other attachments are also contemplated such as a friction fit, threaded attachment, other forms of latch, etc., as well as other types of snap fits to provide an attachment that maintains an airtight seal so the air is contained within the air lumen and balloon of the catheter 600.

The housing (connector) 670 attached to catheter 600 has a proximal opening 672 and an internal channel (lumen) 680 (FIG. 65) to receive an elongated (rod-like) member or nose 334 extending distally from transducer hub 330. As shown, channel 680, which communicates with lumen 620a of port 620 has a first diameter region 680b, a second larger diameter region 680a proximal of region 680b to receive the male rod 334 of the hub 330, and a still larger diameter region 680c (FIG. 69) proximal of region 680a to form a receptacle for O-ring 682. This configuration of channel 680 provides a region larger than the OD of the rod 334 so it is not a one-one ratio. In a one-one ratio, a small pressure drop in the balloon would result in a large pressure drop in the system. Thus, the channel 680 is configured/sized to provide extra volume to act as a capacitor to slow down the percentage pressure loss and stabilize the pressure readings due to loss of air when compressed. The channel 680 has a distal larger diameter region 680d extending from narrowed region 680b to form a funnel for entry of the tubular portion 609 of the inner pressure balloon 608. The tubular portion 609 of the inner balloon 608 in manufacture is slid into/pressed into the funnel 680d until it cannot go in any further due to the reduced channel portion 680b. The tubular portion 609 of balloon 608 can be glued into place within region 680d. Note that in the illustrated embodiment, the tubular portion 609 of inner balloon 608 would extend into and through side port 620 into connector 680d. However, in alternate embodiments, the tubular portion 609 of balloon 608 could terminate further distally within angled port 620, and in some embodiments could terminate even further distally, i.e., within catheter lumen 644 so that air would be advanced by rod 334 through lumen 644 and then into the tubular portion 609 through a proximal opening in tubular portion 609 communicating with lumen 644.

Figure 28D:
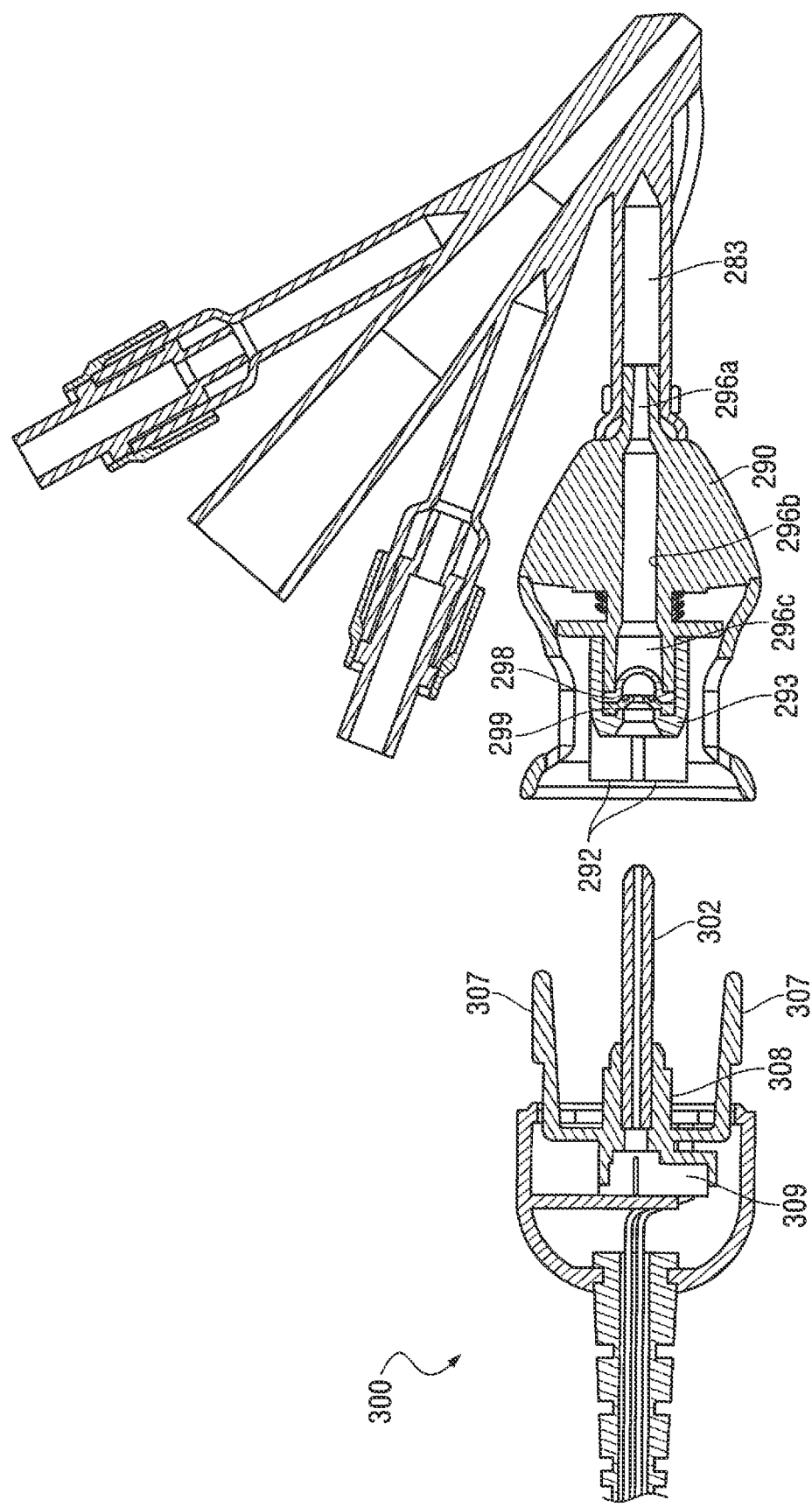
FIG. 28D is a cutaway side view similar to FIG. 28B from the other side.

Instead of valves as in the embodiment of FIG. 28D, two O-rings 684, 682 are seated within connector 670 with O-ring 682 positioned in support or cup 676 and O-ring 684 positioned distal of support 676 in a recess in connector 670. Thermistor barrel shape receptacles 678 (FIGS. 66C, 67 and 68) receive thermistor connectors or pins 335 (FIG. 64), and a metal piece (receptacle) is positioned within each plastic barrel 678, each forming a female receptacle for the male pin(s) 335. The thermistor wires 679, shown in FIGS. 66B and 66C, extend from the thermistor, positioned in the catheter 600 adjacent the drainage lumen, through lumen 644 and through side port 620. (Alternatively, the wires can extend through a separate lumen in the catheter). The two wires 679 extend through an elongated groove 673a and slot 673c in conical connector part 673, and are then wrapped (spooled) around shaft 681 and retained by flange 673b. The wires 679 extend through the flange 673b and are split to each electrically connect with a metal piece (receptacle) in one of the female connector barrels 678. C-shaped extension 671a of cover 671 is inserted into slot 673c covering the wires 679. When cover 671 is placed over holder 673, the wires 679 are hidden to protect the wires. Thus, as can be appreciated in the view of FIG. 64, once assembled, the wires 679 are not visible.

Hub 330 is mounted to connector 670 and includes a housing 331 from which a pair of distally extending snap fit connector arms 332 extend. The latch arms 332 are sufficiently flexible to enable attachment and have an enlarged distal portion 332a, illustratively shown as arrow shaped although other enlarged shapes could be provided. The elongated member (rod or nose) 334 extends between the latch arms 332. When the hub 330 is mounted to the connector 670, the elongated member 334 extends into the channel 680 of connector 670 to advance air though inner balloon tubular portion 609 to inflate the inner balloon 608. The enlarged ends 332a of latch arms 332 enter recesses 674 and engage shoulders 674a to retain the hub 330. The arrowhead tips of the latch arms 332 are at an acute angle to create a positive lock so that once engaged with the shoulder 674a, the hub 330 cannot be pulled proximally unless the latch arms 332 are released. To release (disconnect) the hub 330, the ends 332a are pressed radially inwardly to disengage from shoulder 674a and the hub 330 is pulled proximally. Note that alternatively a different number of latch arms could be provided. The distally extending thermistor pins 335 engage thermistor connectors within barrels 678 of connector 670 which have an interior stop to limit insertion of hub 330. This connection of the hub 330 and connector 670 limit lateral and longitudinal movement to ensure accurate pressure readings as lateral movement, for example, could change the pressure. The longitudinal movement is restricted in a proximal direction by the latch arms/shoulder engagement and in a distal direction by the full insertion of the thermistor pins 335 or alternatively by engagement of the hub 330 and housing 670 distal and proximal surfaces. The O-ring engagement of the elongated rod 334 limits lateral movement of the rod 334 and therefore restricts lateral movement of the hub 330.

Printed circuit board 336 containing the pressure sensor is mounted within hub 330. It can be bonded to a support within the hub. Note a digital pressure sensor can be used instead of an analog sensor in this embodiment as well as the other embodiments disclosed herein.

When transducer hub 330 is attached to connector 670, such attachment inserts the elongated rod 334 into lumen 680 to advance air though the tubular portion 609 of the inner balloon 608 and into the inner balloon 608 to inflate the balloon 608. The elongated member 334 also has a channel or lumen 337 (FIG. 65) extending therethrough to allow the pressure wave to travel through to the pressure sensor of PCB 336. Although in preferred embodiments no additional air needs to be injected into balloon 608 after attachment of hub 330, it is also contemplated that a port or opening can be provided in hub 330 to receive an injection device for injection of additional air. Such additional air can communicate with and flow through channel 337 of elongated member 334, into the tubular portion 609 and inner balloon 608 for inflation, or alternatively, a side port or opening in the angled port downstream (distal) of the elongated member 334 could be provided. Attachment of hub 330 to housing 670 also automatically connects thermistor connectors (within barrels 678) to thermistor pins 335 to automatically connect the temperature sensor (within the catheter) to the hub 330 for communication via a cable to a temperature monitor.

In use, to charge the system, when the hub 330 is mounted to the catheter side port 620 via attachment to connector (housing) 670, the elongated member 334 extends into lumen 680 to advance air through the lumen into balloon 608 to expand the balloon 608. That is, connection of the transducer hub 330 to the catheter 600 (port 620) automatically advances air through the connector lumen 680 and tubular portion 609 to expand the inner balloon 608. Such connection also automatically connects the temperature sensor to the hub 330. In some embodiments, 0.2 cc of air can be displaced/advanced by the elongated member 334, although other volumes are also contemplated. Thus, as can be appreciated, mounting of the hub 330 to the catheter 600 automatically pressurizes the air lumen/chamber and expands the balloon. Note the balloon can be partially or fully inflated (expanded), dependent on the amount of air advanced into the balloon. Further note that preferably the lumen is not vented to atmosphere when the transducer hub 330 is attached and air is advanced through the air lumen.

Note the lumen which is used to inflate the pressure balloon and create the air column has an opening at a distal region to communicate with the interior of the pressure balloon. If an outer balloon is provided, an additional lumen can be provided in the catheter to communicate with the outer balloon to fill the outer balloon and an additional angled port (extension) at the proximal end of the catheter would receive an inflation device to inflate, either fully or partially, the outer balloon.

Note in each of the embodiments disclosed herein, air is described as the preferred gas for creating the column and expanding the balloon, however, other gasses are also contemplated for each of the embodiments.

The pressure balloons of the embodiments herein can be symmetrically shaped as shown or alternatively shaped such that a distal region has an outer transverse cross-sectional dimension, e.g., diameter, greater than an outer transverse cross-sectional dimension, e.g., diameter, of the proximal region. A smooth transition (taper) can be provided between the distal region and proximal region, although other configurations are also contemplated. The inner (and outer) balloon can by way of example be made of urethane, although other materials are also contemplated.

The wire connector of the foregoing embodiments can plug into the openings of a connector positioned on or in the hub. The wire connector can be internal of the hub with an opening in the wall of the hub to enable access for the wire connector. Also note that alternatively the wire can include a female connector and the hub can have a male connector. Other types of connectors/connections are also contemplated.

In alternate embodiments, any of the catheters disclosed here can include a pulse oximetry sensor to measure oxygen saturation in the urethral or bladder tissue. The sensor can be located either proximal or distal to the pressure balloon and/or stabilizing balloon. It could also alternatively be mounted within one of the balloons.

Figure 14A:
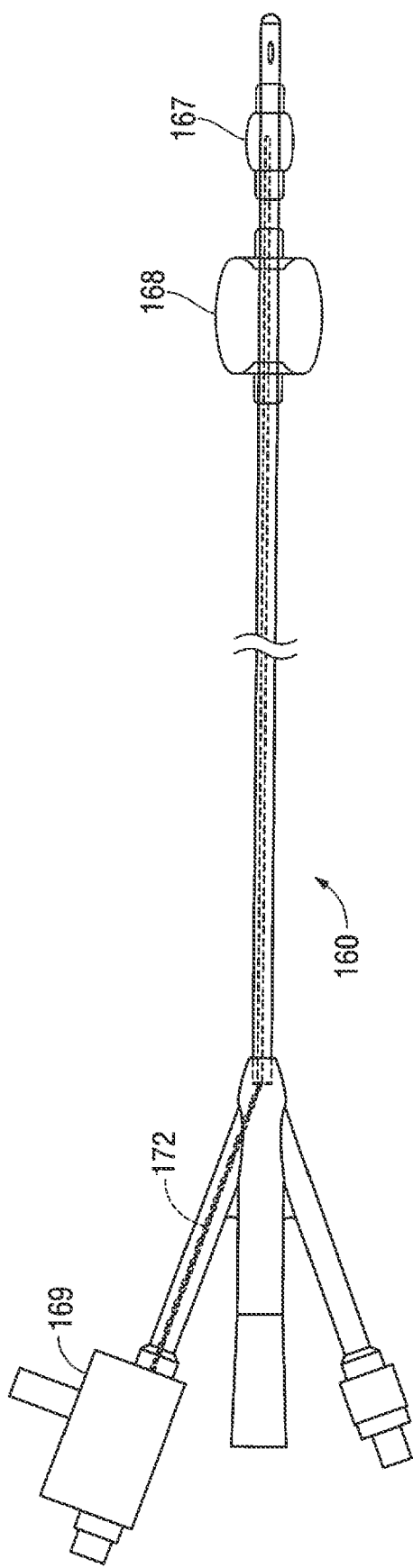
FIG. 14A is a side view of another alternate embodiment of the catheter of the present invention having dual pressure sensors, the first sensor positioned within the air lumen and the second sensor positioned external of the catheter, the two balloons shown in the inflated condition.
Figure 14B:
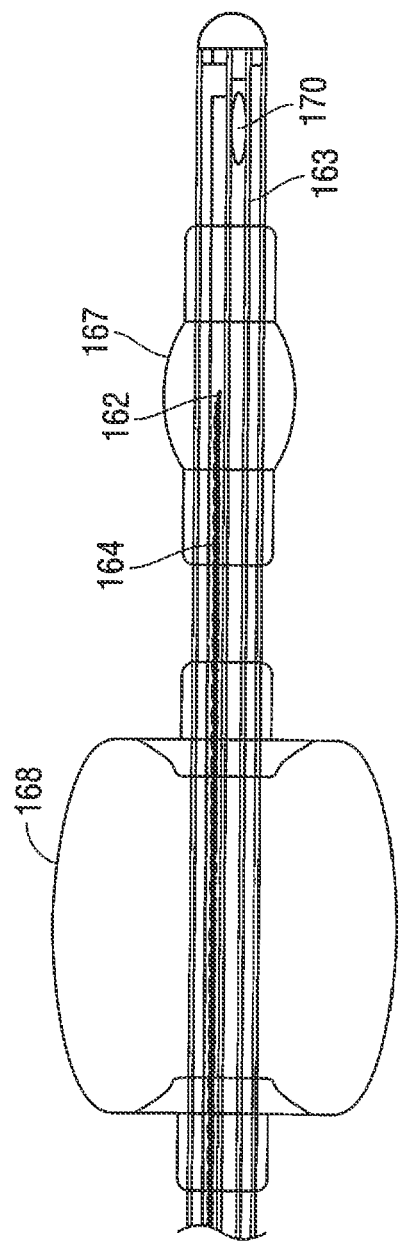
FIG. 14B is an enlarged view of the distal portion of the catheter of FIG. 14A.

It is also contemplated that in some embodiments a backup system be provided to determine pressure. The backup system can provide a double check of pressure readings to enhance accuracy. Such backup system can be used with any of the embodiments disclosed herein to provide a second pressure reading system. One example of such backup system is disclosed in FIGS. 14A and 14B. In this embodiment, catheter 160 has the pressure transducer/pressure sensor 162 like sensor 30 of FIG. 1 within the air (or other gas) lumen 164 communicating with pressure balloon 167, forming a "first system", plus a pressure transducer/pressure sensor 169 at a proximal end of the catheter as in FIG. 12 or external of the catheter forming a "second system". Thus, the pressure sensor 162 is at a distal end of the air charged lumen 164 and pressure sensor 169 is at proximal end of the air charged lumen 164. Both sensors 162 and 169 are electrically connected to a monitor which provides a graphic display of pressure readings. The catheter 160 also includes a temperature sensor either as part of the sensor 162 or a separate component that can be positioned for example in the lumen 164 distal of sensor 162 as in the embodiment of FIG. 8. A stabilizing balloon 168 and an inflation lumen to inflate balloon 168 can also be provided. Lumen 163, having a side opening 170 at its distal end, is configured to drain the bladder similar to lumen 20 and side opening 22 of the embodiment of FIG. 1.

In use, catheter 160 is inserted into the bladder and stabilizing balloon 168 is inflated to secure the catheter 160 in place. The system is charged by inflation of the balloon 167, i.e., preferably partially inflated for the reasons discussed above, by insertion of air through side port 172 which is in fluid communication with the air lumen in a closed system formed by the internal space of the balloon 167 and the internal lumen 164 communicating with the internal space of balloon 167. With the balloon 167 inflated, pressure monitoring can commence as external pressure applied to an outer surface of the balloon 167 compresses the air (or other gas) within the chamber. The sensor 162 at the distal end of lumen 64 provides continuous pressure readings, converted to an electrical signal by the transducer within the distal end of lumen, and then electrically communicates through its transmission wires extending through the air lumen to an external monitor either directly or via a converter. Additionally, pressure within the air charged column is measured at a proximal region by sensor 169 within side port 172 of catheter 160. The sensor 162 at the distal end of lumen 164 provides continuous pressure readings, and such pressure readings can be confirmed by the proximal sensor. Such pressure readings can be performed continuously (along with continuous temperature monitoring) or alternatively can also be adapted if desired for periodic monitoring so the pressure and/or temperature readings can be taken at intervals or on demand by the clinician. Thus, air pressure readings at a proximal end plus microtip pressure readings at the distal end are provided. The sensors 162 and 169 can electrically communicate with an external monitor to display both pressure readings from sensors 162, 169, or alternatively, if the pressure readings are different, they can be averaged to display a single measurement. Clearly, other displays of information can be provided to display the information from the two sensors 162, 169.

The sensors disclosed herein can be microtip sensors within the air (or other gas) lumen or balloon. In alternative embodiments, fiber optic sensors within the air (or other gas) lumen or balloon can by utilized to transmit circumferential/area pressure. The pressure transducers can be housed within the catheter or alternatively external to the catheter. Additionally, core temperature sensors can be part of the pressure sensor or a separate axially spaced component.

The multi-lumen or single lumen catheters disclosed herein provide an air (or other gas) charged balloon (air containing chamber) giving precise readings of intra-abdominal pressure (or for other pressure measurements) and the systems are charged via insertion of air through a side port. The multi-lumen catheters are easily inserted into the bladder in the same manner as standard bladder drainage catheters and enable continuous drainage of urine while continuously recording IAP without interrupting urine flow and without requiring retrograde filling of the bladder with water. Thus, these catheters provide a closed system. The catheters also have a balloon providing a large reservoir (large capacity) and large circumferential area/interface for obtaining more information from the bladder over multiple reference points (rather than a single point sensor) that provides an average pressure to provide a more accurate assessment of the surrounding environment as pressure measurement is not limited to one side of the bladder but can determine measurements on the opposing side as well. The balloon can have a sufficiently large circumferential area so that it is in contact with the bladder wall, and in some embodiments, could distend the bladder wall, thus enabling pressure measurement without insertion of fluid into the bladder. When used in other body cavities for other pressure measurements, the pressure balloon of the multi-lumen or single lumen catheters disclosed herein can be of sufficiently large to contact or in some embodiments, distend the cavity wall, thus enabling pressure measurement without insertion of fluid into the cavity. The balloon, as noted above, of the multi-lumen or single lumen catheters disclosed herein can be impermeable or have an impermeable membrane (as defined herein) to prevent escape of gas to prevent loss of accurate pressure readings.

As noted above the catheters in some embodiments can be connected to a bedside monitor through either a wire or Bluetooth® wireless connection. The system can also in some embodiments include an indicator or alarm system to alert the staff at the site as well as remote staff through wired or wireless connections to external apparatus, e.g., hand held phones or remote monitors.

As noted above, an alarm or indicator can be provided in some embodiments to alert the staff. The indicator can be a visual indicator such as a light, LED, color change, etc. Alternatively, or additionally, the indicator can be an audible indicator which emits some type of sound or alarm to alert the staff. The indicator can be at the proximal region of the catheter or at other portions of the catheter, e.g., at a distal end portion, where known imaging techniques would enable the user to discern when the indicator is turned on. It is also contemplated that in addition to providing an alert to the user in some embodiments, the pressure monitoring system can be tied into a system to directly reduce abdominal pressure so that if the pressure exceeds a threshold level (value), the abdominal pressure can automatically be reduced. In such systems, an indicator can be provided on the proximal portion of the catheter, e.g., at a proximal end outside the patient's body, or separate from the catheter. The sensor can be in communication with the indicator, either via connecting wires extending through a lumen of the catheter or a wireless connection. The sensor can be part of a system that includes a comparator so that a comparison of the measured pressure to a predetermined threshold pressure value is performed and a signal is sent to the indicator to activate (actuate) the indicator if the measured pressure exceeds the threshold pressure to alert the clinician or staff that pressure within the abdomen is too high and a signal is also sent to a device or system to automatically actuate the device or system to reduce the abdominal pressure. If the measured temperature is below the threshold, the indicator is not activated. A similar system can be used for temperature measurement and indication.

It is also contemplated that a micro-air charged sensor could be provided in the retention (stabilizing) balloon.

It is also contemplated that microtip sensors and/or fiber optic sensors can be utilized to measure pressure, and these sensors can be utilized instead of or in addition to the air pressure readings utilizing the aforedescribed balloon(s) for measuring pressure.

Pulse oximeters for measuring oxygen levels (oxygen saturation) in the urethral and/or bladder tissue could also be provided. In some embodiments, the pulse oximetry sensors can be positioned on the catheter proximal to the retention balloon. Alternatively, the sensors can be positioned within the retention balloon, on the catheter distal to the pressure balloon or on other regions of the catheter. Another channel in the catheter can be provided for the sensor and its connector to external devices, e.g. readers.

The catheters disclosed herein are designed for insertion into the bladder. However, it is also contemplated that they can be adapted for insertion into the rectum, colostomy pouch, stomach, supra-pubic bladder drain, or other orifice directly connected with the abdominal cavity. They can also be inserted into other areas connected with other cavities. Uses include by way of example, cardiac use, labor and delivery use, rectal placement for abdominal cavity, use for gastric pressure, esophageal motility, endocranial pressures ERCP, gall bladder, etc.

Pre-Eclampsia Clinical Application

Pre-eclampsia is a disorder that occurs during pregnancy that affects both the mother and unborn baby, and is a rapidly progressive condition that is characterized by high blood pressure. As noted above, globally, pre-eclampsia and other hypertension disorders of pregnancy are a leading cause of maternal and infant illness and death and the second most common cause of preterm birth and infant mortality.

The present invention advantageously provides a system and method for diagnostic testing of pregnant women to reduce adverse outcomes specifically attributable to preeclampsia. The present invention utilizes the abdominal pressure measuring catheters described herein to measure abdominal pressure in the pregnant woman to determine if preeclampsia is occurring, or is likely to occur, so steps can be taken by the clinician to address pre-eclampsia and eliminate or reduce the impact of preeclampsia on the mother and baby. That is, the measurements will enable the clinician to determine when intervention and delivery should occur to prevent morbidity and mortality of the mother and baby. As the pressures start to rise, the clinician might be able to intervene with conservative management to buy more time before delivery giving less premature deliveries and better fetal outcomes.

It is currently believed that the placenta mediates the systemic inflammatory response characteristic of pre-eclampsia but the etiology and exact pathways remain an enigma. Intra-abdominal hypertension (IAH) (pressure>12 mmHg) is well published in the areas of critical care and surgery, but not in pregnancy. It is currently believed that delivery of the placenta is what cures pre-eclampsia, and abdominal decompression at birth has not to date been considered a potential mechanism.

Despite decades of research, the specific etiology of preeclampsia and its complete pathogenesis remain unknown. Poor identification of the progression of preeclampsia and the risks of adverse outcomes can lead to unnecessary intervention (e.g. preterm delivery). Moreover, the delay of diagnosis and management has the potential to negatively affect pregnancy outcomes.

Currently, doctors believe that pre-eclampsia is caused from the afterbirth (placenta) because when the mother gives birth, she gets better within a few days. Most research around pre-eclampsia today is done to try to understand how and why the placenta causes pre-eclampsia, but to date no one has been able to figure this out. It is known that high fluid pressure in the abdomen causes damage to the cells and organs, however, to date, the focus has not been on the cause/effect. The present invention provides a novel approach for diagnosing pre-eclampsia by measuring the abdominal pressure, and using such pressure measurements to determine the presence and/or likelihood of pre-eclampsia. With this novel approach, pre-eclampsia can be tracked and necessary steps taken to avoid the complications and adverse affects on the mother and infant resulting from pre-eclampsia. Such steps (interventions) are discussed below.

When the pressure in the abdomen gets too great in critical care, the patient needs abdominal surgery to lower the pressure. While most doctors today believe that women get better from pre-eclampsia after the baby delivers because the placenta has delivered, it is likely that the pressure in the mother's abdomen has been lowered because the baby no longer occupies space or creates pressure in the mother's abdomen. There are many laws of physics that apply to fluid pressure, force and gravity. The uterus applies a magnitude of "force" to the mother's tissues and organs and sometimes that force is excessive and causes damage to her organs—known as pre-eclampsia. As damage happens to some organs, the pressure inside the mother's abdomen continues to build up because the baby keeps growing and the mother's stomach muscles just cannot stretch any further. Now the pressure is forced to spill over, or "offloads" higher up into her body to her chest (because it has nowhere else to go and laws of fluid pressure allow this), causing problems with her lungs. If the pressure in her abdomen gets really high, the pressure further offloads from her chest into her head, causing seizures. Thus, high abdominal pressure is associated with pre-eclampsia.

Consequently, the catheters described above can be used to measure abdominal pressure in the pregnant mother. IAP continuous measurement is provided by these catheters. The measurement can be performed at different stages in pregnancy as the catheter is easily inserted into the bladder as described above. If abdominal pressure is found to be high, steps can be taken to reduce the pressure and thereby reduce the risk and associated adverse affects of pre-eclampsia. In some embodiments, by way of example if the abdominal pressure is over 25 mmHg, this could be used as a threshold to indicate an increased risk of mortality to trigger intervention. Other pressure measurements thresholds are also contemplated.

If the pressure exceeds a predetermined value, one step (intervention) to be taken, for example, can be to alter the mother's position from lying down, to her left side, to knee-chest position to alter (lower) the "force" that the pregnant abdomen applies on the mother's internal organs. Other possible steps (interventions) include for example decreasing fluid intake, limiting IV fluids, administering medications or delivery of the baby. Thus, if the measured values are less than a selected (predetermined) pressure value, the likelihood of eclampsia is low and the pregnancy can be safely continued, therefore, decreasing premature delivery complications. Conversely, if safe pressure readings are exceeded (e.g. >25-30 mmHg), i.e., pressure reading exceeds a predetermined value, delivery needs to be imminent to save the mother and child. Also, alternative interventions for severe pre-eclampsia preterm may warrant consideration of other actions such as prenatal laparoscopic separation of the rectus abdominis muscle to relieve IAP and permit continuation of the pregnancy. Other steps are also contemplated to treat pre-eclampsia as a result of the pressure measurement of the catheters of the present invention.

It should be appreciated that various embodiments of catheters are described herein, e.g., single pressure balloon, inner and outer pressure balloon, pressure sensor(s) in the lumen, different lumen arrangements/configurations, etc. Each of these catheters can be utilized for the pre-eclampsia diagnosis, i.e., assessment of occurrence (presence) or likelihood of pre-eclampsia. For example, a catheter that can be utilized can include an 18 French catheter with a temperature sensor and a micro air-charged pressure balloon column to an external pressure sensor with urine drainage channel to a separate bag for urine output. The cable connects into existing monitor systems for ICU, anesthesia and labor and delivery suites. The data from IAP (intra-abdominal pressure) are evaluated by electronically recording end expiratory pressures. Alternatively, other catheters insertable into the bladder with abdominal pressure measurement capabilities can be utilized for such diagnosis.

Note intra-abdominal hypertension and compartment syndrome are likely associated with, and may actually cause pre-eclampsia. The relationship between mean arterial pressure (MAP mmHg), intra-abdominal pressure (IAP mmHg), and abdominal perfusion pressure (APP mmHg) in women preterm to term can be calculated, and the calculation of APP requires the IAP value (APP=MAP−IAP).

IAH is recognized to have devastating effects on all organ systems. Unabated, it results in abdominal compartment syndrome, poly-compartment syndrome (transfer of IAP to the thoracic and intra-cranial cavities), multi-organ dysfunction, and imminent death. Concurrently, due to ischemia reperfusion injury in the maternal bowel, bacterial translocation of lipopolysaccharide (LPS) endotoxin from the intestinal lumen to the mesenteric lymph nodes, portal vein and liver can occur triggering a cytotoxic immune response. This is recognized as a life-threatening complication of increased IAH. Intra-abdominal hypertension and ACS are recognized as conditions associated with injury or disease in the abdomino-pelvic region, and the definitive treatment is surgical abdominal decompression. Intra-abdominal hypertension in pregnancy is caused by intra-abdominal pressure in pregnancy >12 mmHg, that when sustained or increasing, leads to hemodynamic shifts, intestinal ischemia reperfusion injury, translocation of lipopolysaccharide endotoxin to the liver, systemic cytotoxic immune response, multi-organ dysfunction, and poly-compartment syndrome.

Although the apparatus and methods of the subject invention throughout the entire application have been described with respect to preferred embodiments, those skilled in the art will readily appreciate that changes and modifications may be made thereto without departing from the spirit and scope of the present invention as defined by the appended claims.

What is claimed is:

1. A method for measuring intra-abdominal pressure in a pregnant woman to assess occurrence or likelihood of pre-eclampsia via insertion of a pressure measuring catheter into the woman, the method comprising the steps of:
   providing a catheter having a first lumen and a balloon;
   inserting the catheter into the woman;
   injecting gas into the first lumen of the catheter to expand the balloon from a deflated condition to a more inflated condition;
   after expanding the balloon, continuously monitoring pressure to obtain multiple pressure readings based on deformation of the partially inflated balloon to thereby monitor pressure within an abdomen of the woman to assess if pre-eclampsia is occurring or likely to occur, and
   transmitting the multiple pressure readings continuously to an external monitor connected to the catheter for a display of the multiple pressure readings, a pressure reading of the multiple pressure readings indicative of a presence and/or risk of pre-eclampsia based on intra-abdominal pressure to determine when intervention should occur to prevent morbidity and mortality of the woman and baby;
   wherein the catheter includes an additional lumen and a stabilizing balloon, the additional lumen communicating with the stabilizing balloon to inflate the stabilizing balloon to stabilize a position of the catheter, the stabilizing balloon positioned proximal of the balloon and axially spaced from the balloon such that a distalmost end of the stabilizing balloon is spaced proximally from a proximalmost end of the balloon.

2. The method of claim 1, wherein multiple pressure readings are taken and if one of the multiple pressure readings exceeds 25 mmHg, the intervention is implemented.

3. The method of claim 1, further comprising the step of placing a distal region of the balloon against a wall of the rectum.

4. The method of claim 1, wherein after initial advancement of gas into the first lumen by connection of a pressure transducer, additional air does not need to be inserted during a duration of insertion of the catheter in a body of the woman.

5. The method of claim 1, further comprising the step of altering a position of the woman if one of the multiple pressure readings exceeds a predetermined pressure to reduce the risk of pre-eclampsia.

6. The method of claim 1, further comprising the step of reducing fluid intake to the woman if one of the multiple pressure readings exceeds a predetermined pressure to reduce the risk of pre-eclampsia.

7. The method of claim 1, further comprising the step of delivering the baby if one of the multiple pressure readings exceeds a predetermined pressure to reduce the risk of pre-eclampsia.

8. The method of claim 1, wherein connection of a hub automatically connects a temperature sensor of the catheter to a connector within the hub.

9. The method of claim 1, wherein the catheter includes an outer balloon positioned over the balloon, the outer balloon inflatable through a separate second lumen of the catheter independent of the first lumen and radially spaced from and external of the first lumen, and the outer balloon while inflated is deformable based on pressure to deform the balloon within the outer balloon to provide finer measurements of pressure, the balloon within the outer balloon having a transverse dimension in an expanded condition less than a transverse dimension of the outer balloon in an expanded condition along an entire circumference.

10. The method of claim 1, wherein the catheter is inserted into a rectum of the woman to obtain the pressure readings.

11. The method of claim 1, wherein the catheter is inserted into an esophagus of the woman to obtain the pressure readings.

12. The method of claim 1, wherein a pressure sensor is positioned within the balloon.

13. The method of claim 12, wherein pressure is measured in response to deformation of the balloon in response to pressure exerted on an outer wall of the balloon.

14. The method of claim 12, further comprising a side opening in the catheter communicating with the bladder for drainage.

15. A method for measuring intra-abdominal pressure in a pregnant woman to assess occurrence or likelihood of pre-eclampsia via insertion of a pressure measuring catheter into a rectum of a woman, the method comprising the steps of:
   providing a catheter having a first lumen and a pressure sensor,
   inserting the catheter into the rectum of the woman;
   inflating a balloon to provide continuity to a wall of the rectum, wherein a predetermined amount of air is advanced into the balloon prior to use of the pressure sensor,
   after inflation of the balloon, continuously monitoring pressure via obtaining multiple pressure readings of the continuous pressure monitoring based on the pressure sensor to thereby monitor pressure within an abdomen of the woman to assess if pre-eclampsia is occurring or likely to occur; and
   transmitting the pressure readings continuously to an external monitor connected to the catheter for a display of the pressure readings, a pressure reading of the multiple pressure readings indicative of a presence and/or risk of pre-eclampsia based on intra-abdominal pressure to determine when intervention should occur to prevent morbidity and mortality of the woman and baby;
   wherein the catheter includes an additional lumen and a stabilizing balloon, the additional lumen communicating with the stabilizing balloon to inflate the stabilizing balloon to stabilize a position of the catheter, the stabilizing balloon positioned proximal of the balloon and axially spaced from the balloon such that a distal-most end of the stabilizing balloon is spaced proximally from a proximalmost end of the balloon.

16. The method of claim 15, wherein the balloon is partially inflated and the step of obtaining pressure measurements obtains pressure readings based on deformation of the partially inflated balloon.

17. The method of claim 15, wherein a hub contains the pressure sensor and is attachable to the first lumen, and attachment of the hub automatically connects a temperature sensor of the catheter to a connector within the hub.

18. The method of claim 15, wherein a pressure sensor is positioned within the balloon.

19. The method of claim 18, wherein pressure is measured in response to deformation of the balloon in response to pressure exerted on an outer wall of the balloon.

20. The method of claim 18, further comprising a side opening in the catheter communicating with the bladder for drainage.

* * * * *